(12) United States Patent
Ali et al.

(10) Patent No.: US 10,561,689 B1
(45) Date of Patent: Feb. 18, 2020

(54) METHOD OF TREATING NERVE DAMAGE

(71) Applicants: Jassim M. Hassan M. Ali, Safat (KW); Waleed Renno, Safat (KW)

(72) Inventors: Jassim M. Hassan M. Ali, Safat (KW); Waleed Renno, Safat (KW)

( * ) Notice: Subject to any disclaimer, the term of this patent is extended or adjusted under 35 U.S.C. 154(b) by 39 days.

(21) Appl. No.: 16/292,976

(22) Filed: Mar. 5, 2019

(51) Int. Cl.
*A61K 35/60* (2006.01)
*A61K 9/00* (2006.01)
*A61K 9/06* (2006.01)

(52) U.S. Cl.
CPC ............ *A61K 35/60* (2013.01); *A61K 9/0014* (2013.01); *A61K 9/06* (2013.01)

(58) Field of Classification Search
None
See application file for complete search history.

(56) References Cited

U.S. PATENT DOCUMENTS

| | | | |
|---|---|---|---|
| 5,658,594 A | 8/1997 | Al-Hassan | |
| 5,912,018 A | 6/1999 | Al-Hassan | |
| 8,551,532 B2 | 10/2013 | Al-Hassan | |
| 2013/0108705 A1* | 5/2013 | Al-Hassan | A61K 35/60 424/537 |

OTHER PUBLICATIONS

Al-Hassan et al. (2005). "Novel action of the preparations from the skin of the Arabian Gulf catfish (*Arius bilineatus val.*) on back pain and other neurological problems," Conference Paper, Congress on Interdisciplinary neurological aspects, Kuwait. (Year: 2005).*
Al-Hassan et al., "Skin Preparations from Catfish (*Arius bilineatus, val.*) Contain a Lipid Which Inhibits Cancer Cell Survival In Vitro," The FASEB Journal, vol. 30, No. 1 supplement, Apr. 1, 2016.
Yang et al., "Abstract 2246: Anti-proliferative activities of lipid fraction of extract from the skin of the catfish *Arius bilineatus, valenciennes*," AACR Annual Meeting 2017; Apr. 1-5, 2017; Washington, DC.
Yang et al., "Anti-proliferative and anti-invasiveness of the lipid fraction of the skin extract from the catfish *Arius bilineatus, valenciennes* in human pancreatic cancer is associated with regulation of lipid metabolism," Cancer Research 77, (13 Supplement):2246-2246, Jul. 2017.

* cited by examiner

*Primary Examiner* — Christina Bradley
(74) *Attorney, Agent, or Firm* — Richard C. Litman; Nath, Goldberg & Meyer

(57) ABSTRACT

A method of treating damaged nerves can include administering a therapeutically effective amount of a composition comprising a soluble protein fraction obtained by fractionating epidermal gel secretions of catfish to a patient in need thereof. The soluble protein fraction can include about 87% soluble proteins and about 13% lipids. The composition can be administered by intraperitoneal (IP) or sub-cutaneous (SC) injection.

10 Claims, 39 Drawing Sheets

FIG. 1B
FIG. 1C
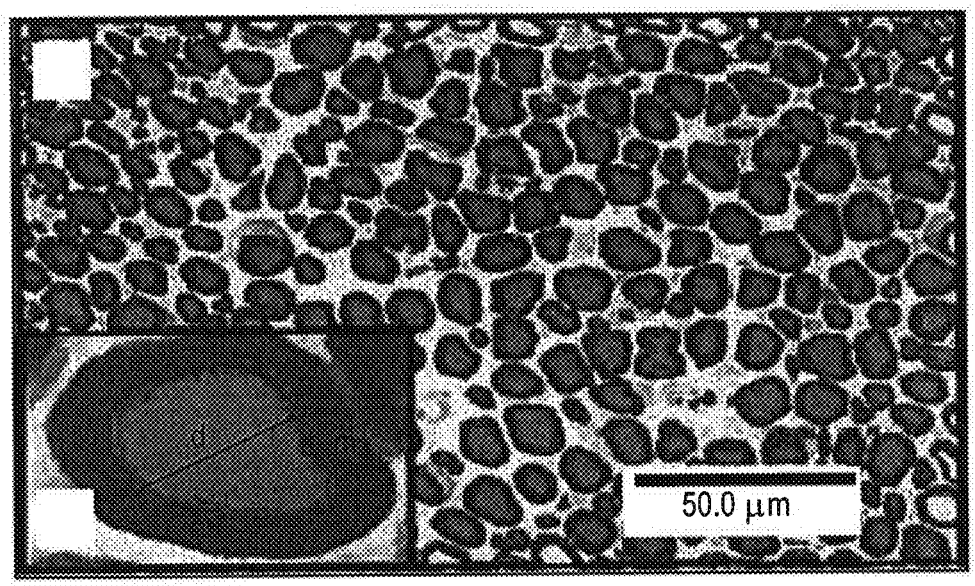
FIG. 1D
FIG. 1E
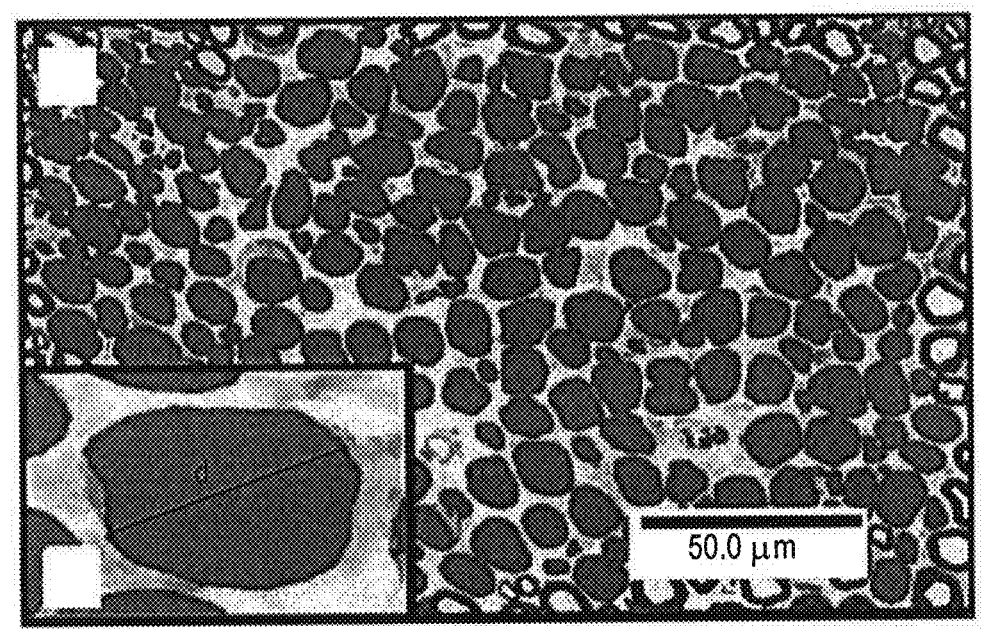

Week 4

Week 4

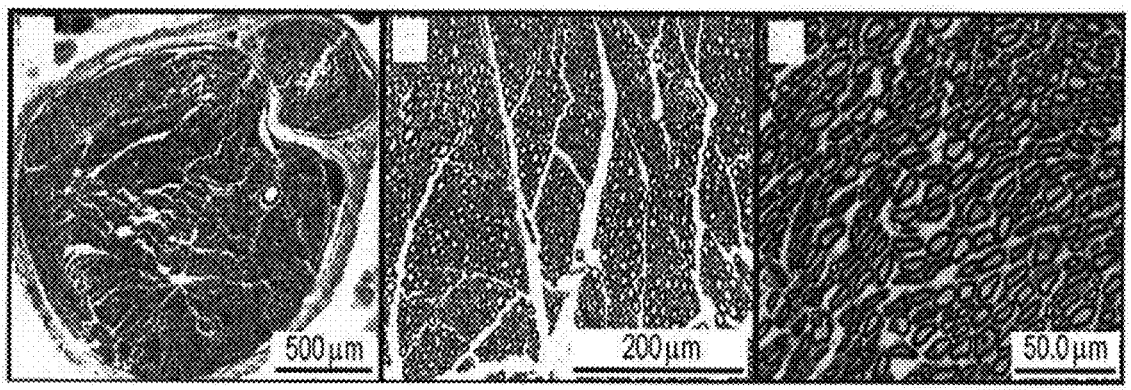
FIG. 5A  FIG. 5B  FIG. 5C
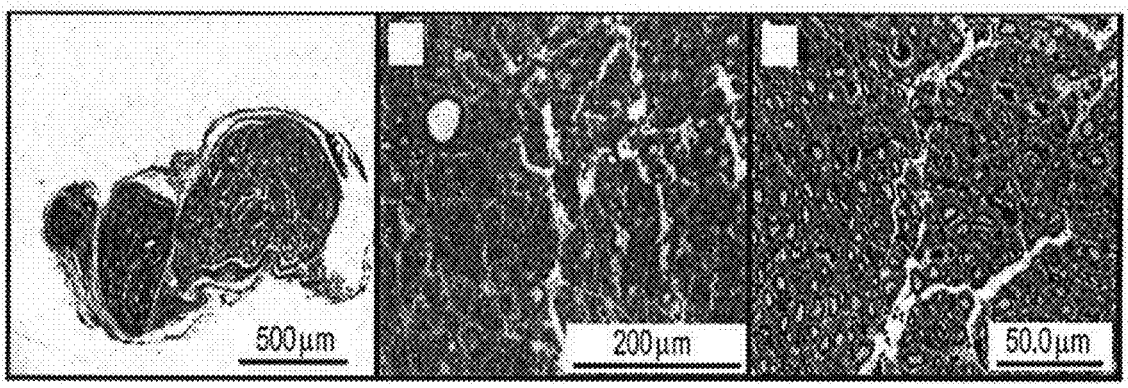
FIG. 5D  FIG. 5E  FIG. 5F

Week 4

Week 4

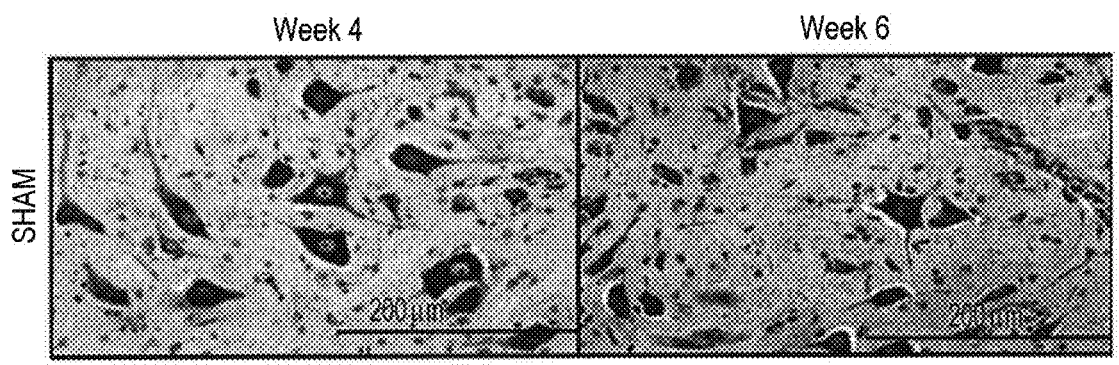
FIG. 9A          FIG. 9B
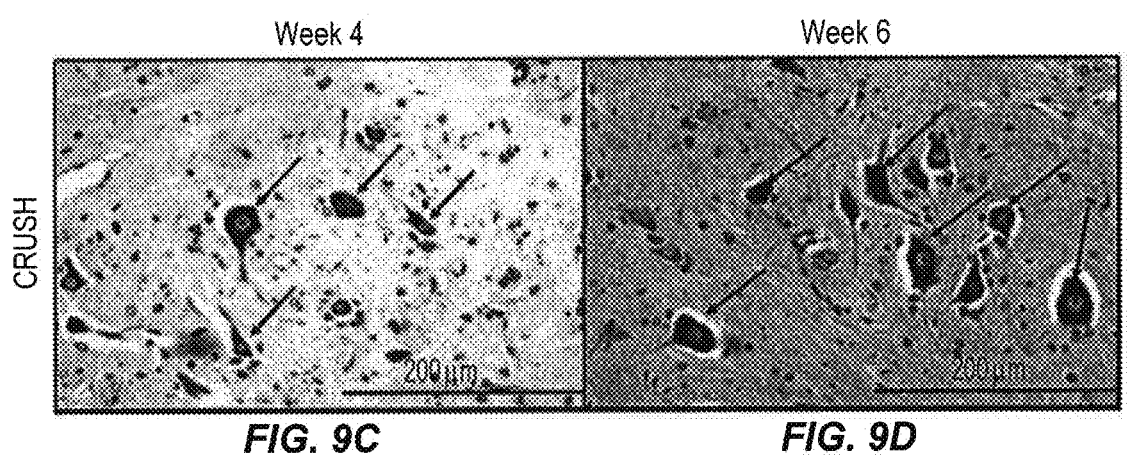
FIG. 9C          FIG. 9D

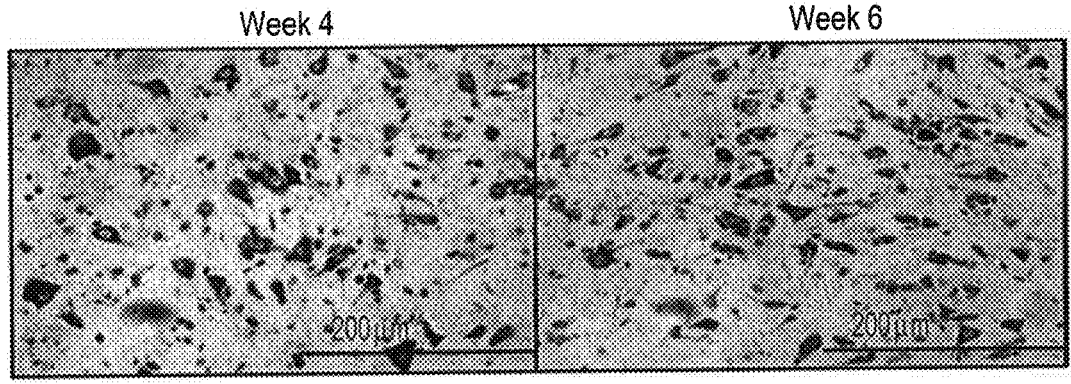
FIG. 10E FIG. 10F
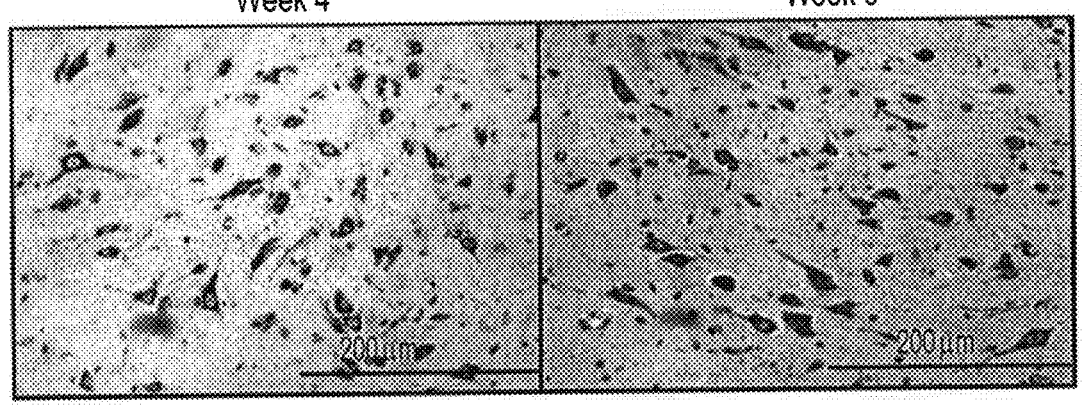
FIG. 10G FIG. 10H

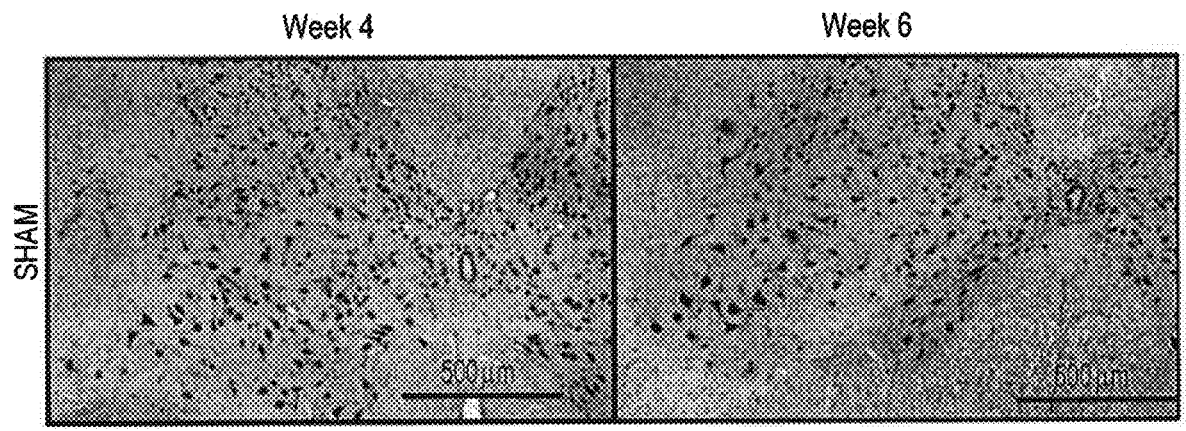
FIG. 11A  FIG. 11B
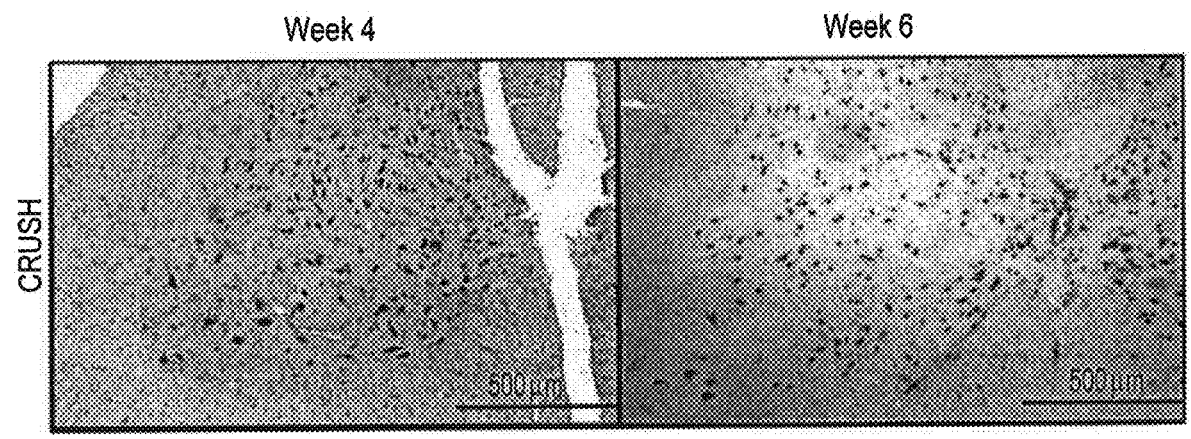
FIG. 11C  FIG. 11D

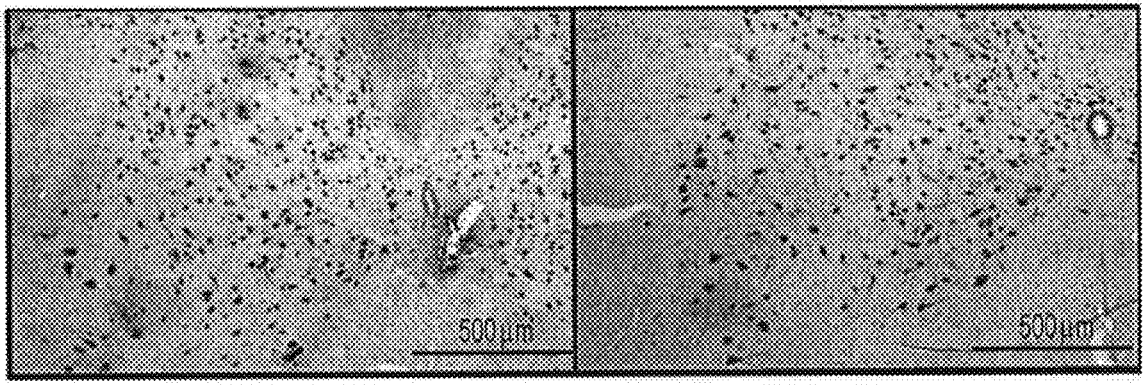
FIG. 11E  FIG. 11F
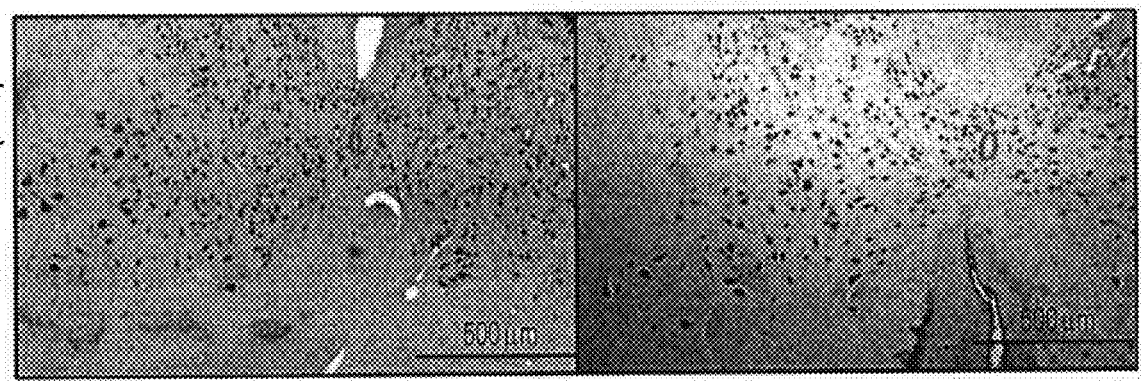
FIG. 11G  FIG. 11H

Week 4          Week 6

Week 4          Week 6

Week 4          Week 6

Week 4          Week 6

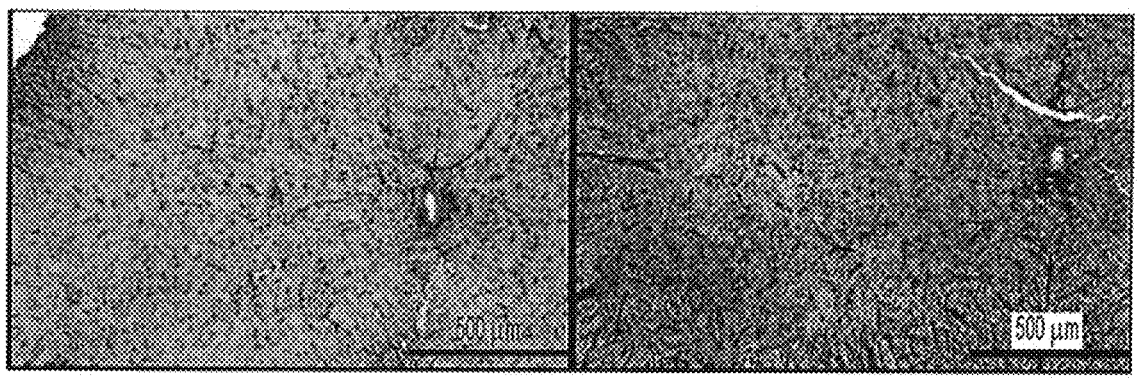
FIG. 15E  FIG. 15F
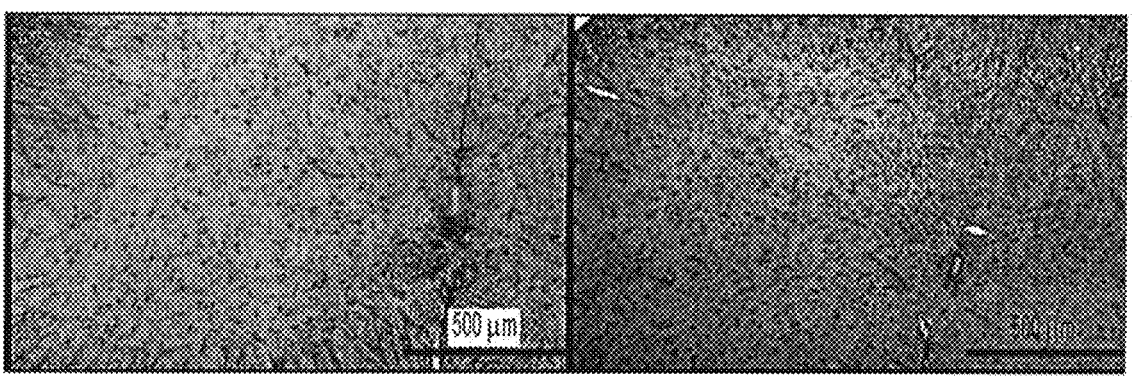
FIG. 15G  FIG. 15H

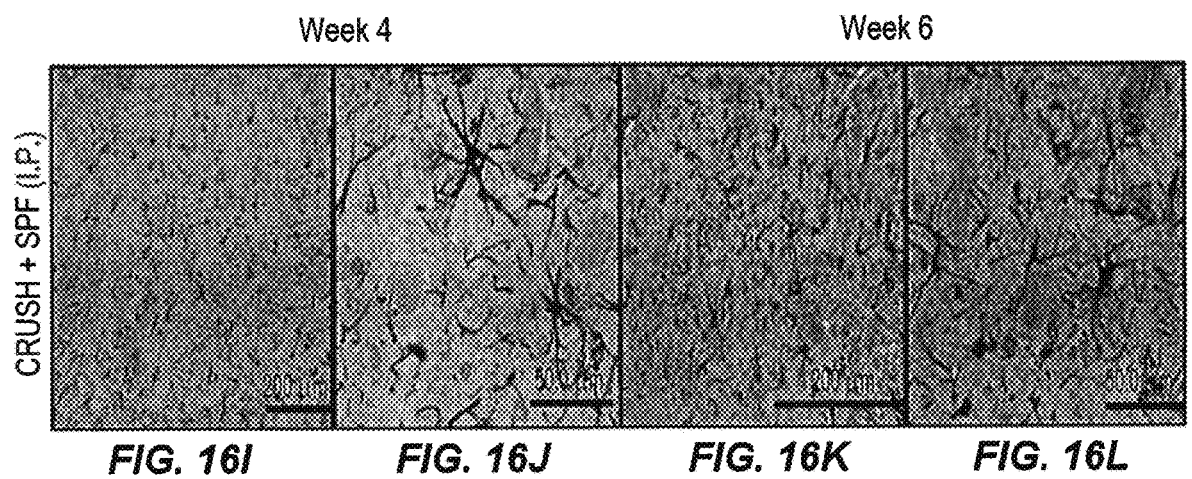
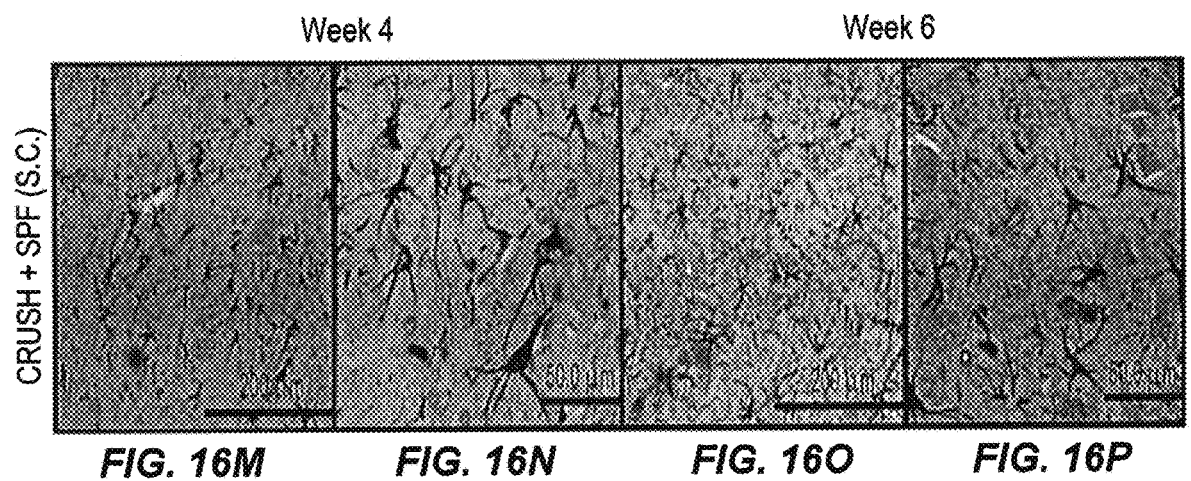

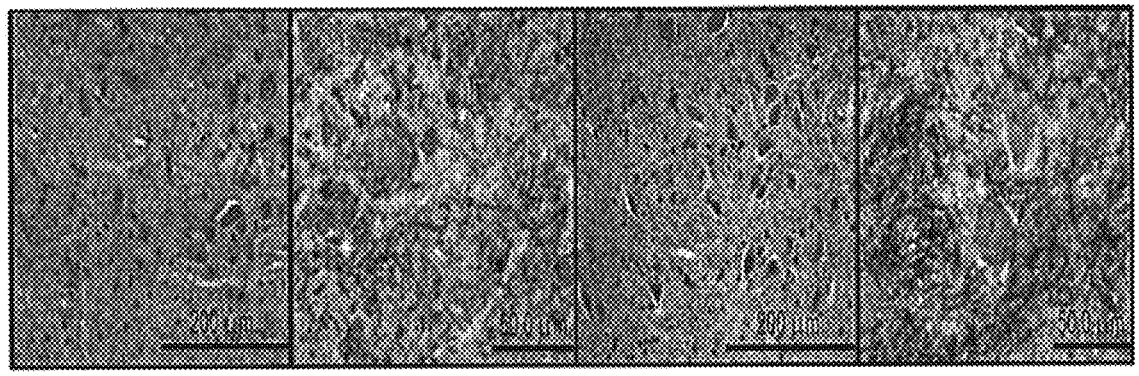
Week 4        Week 6
*FIG. 19I*    *FIG. 19J*    *FIG. 19K*    *FIG. 19L*
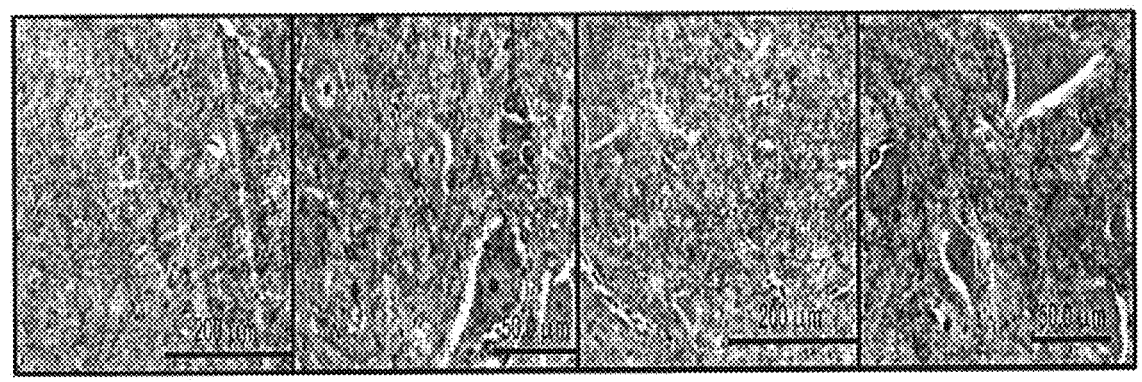
*FIG. 19M*    *FIG. 19N*    *FIG. 19O*    *FIG. 19P*

METHOD OF TREATING NERVE DAMAGE

BACKGROUND

1. Field

The disclosure of the present patent application relates to use of epidermal gel secretions of catfish for therapeutic purposes, and particularly, to a method for regeneration of crushed nerves, and/or the resulting symptoms of neurobehavioral, as well as axonal, neuronal, and histopathological changes resulting from crush, using epidermal gel secretions of catfish.

2. Description of the Related Art

Injuries to the nervous system affect millions of human beings around the world. Injuries to peripheral nerves can be caused by trauma, surgery, cancer, diabetes mellitus, or congenital anomalies. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons.

Peripheral nerve injury is a major source of morbidity and an area with significant medical need. For example, failure of nerve regeneration often necessitates amputation of an otherwise salvaged limb.

The Arabian Gulf catfish (*Arius bilineatus* (*Valenciennes*)) naturally exudes a proteinaceous gel-like material ("epidermal gel secretion") from its epidermis upon stress or injury. The epidermal gel secretion includes a complex mixture of biochemically and pharmacologically active components. Often times, however, the Arabian Gulf catfish produces venoms from its venomous spines and venom glands near its pectoral spines which mix with secretions on the catfish skin. Additionally, since the gelatinous secretion is exuded while the catfish is still alive, contaminants other than the venom (such as feces, vomit and blood) are also often mixed with the epidermal secretion.

SUMMARY

A method of treating damaged nerves can include administering a therapeutically effective amount of a composition comprising a soluble protein fraction obtained by fractionating epidermal gel secretions of catfish to a patient in need thereof. The soluble protein fraction can include soluble proteins and lipids obtained by fractionating the epidermal gel secretions of catfish. The soluble protein fraction can include about 87% soluble proteins and about 13% lipids. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

Fractionating the epidermal gel secretion of catfish can include mixing the catfish epidermal gel secretions with phosphate buffered saline to provide an extract, homogenizing the extract to provide a homogenized extract, and centrifuging the homogenized extract to provide a soluble protein fraction and an insoluble protein fraction. The soluble fraction can be freeze dried to provide a powdered soluble fraction. If desired, the insoluble protein fraction can be fractionated (in the manner described above for fractionating the EGS) to separate any undissolved soluble proteins therefrom. The additional soluble protein fraction extracted from the insoluble protein fraction can be added to the original soluble protein fraction to enrich the original soluble protein fraction.

The freeze-dried soluble fraction can be analyzed to determine a ratio of the concentration of soluble protein to lipids. Generally, it can be expected that the freeze-dried powdered soluble fraction includes about 87% soluble proteins. If the freeze-dried powdered soluble fraction includes less than about 13% lipids, however, the soluble fraction can be supplemented with lipids from an additional lipid fraction to provide a soluble protein fraction having about 87% soluble proteins and about 13% lipids. The additional lipid fraction can be obtained from the freeze-dried EGS. The therapeutic composition can include the soluble protein fraction having about 87% soluble proteins and about 13% lipids.

For administration of the composition, the soluble protein fraction can be taken out of deep freeze (−80° C.), dissolved in saline in phosphate buffer (pH 7.5), and maintained at temperatures ranging from about 4° C. to about 6° C. to be ready for administration. In an embodiment, the composition includes the soluble protein fraction dissolved in phosphate buffer saline. It is preferable to dissolve the soluble protein fraction and administer the composition when the composition is still cold, e.g., temperatures ranging from about 4° C. to about 6° C. For example, the composition can be maintained in crushed ice or in a refrigerator until it is ready to be administered.

These and other features of the present disclosure will become readily apparent upon further review of the following specification.

BRIEF DESCRIPTION OF THE DRAWINGS

FIG. 1B shows a representative micrograph of a cross-section of sciatic nerve myelinated axons stained with toluidine blue demonstrating the method of calculating myelin thickness and g-ratios.

FIG. 1C shows a representative micrograph of a cross-section of sciatic nerve myelinated axons stained with toluidine blue demonstrating the method of calculating myelin thickness and g-ratios.

FIG. 1D shows a representative micrograph of a cross-section of sciatic nerve myelinated axons stained with toluidine blue demonstrating the method of calculating myelin thickness and g-ratios.

FIG. 1E shows a representative micrograph of a cross-section of sciatic nerve myelinated axons stained with toluidine blue demonstrating the method of calculating myelin thickness and g-ratios.

FIGS. 5A-5L show Toluidine blue stained photomicrographs of semi-thin transverse sections of sciatic nerves obtained from animals in the SHAM (FIG. 5A, FIG. 5B and FIG. 5C), CRUSH (FIG. 5D, FIG. 5E and FIG. 5F), CRUSH+0.5×SPF(I.P.) (FIG. 5G, FIG. 5H and FIG. 5I) and CRUSH+1×SPF(S.C.) (FIG. 5J, FIG. 5K and FIG. 5L) groups at Week 6 following nerve injury (Column I; 10×, Column II, 40× and Column III, 100×). Sciatic nerve sections of CRUSH+0.5×SPF(I.P.) are shown in FIG. 5G, FIG. 5H, and FIG. 5I. Sciatic nerve sections of CRUSH+1×SPF (S.C.) are shown in FIG. 5J, FIG. 5K and FIG. 5L.

FIGS. 9A-91H depict photomicrographs of cresyl violet stain of ventral grey horn of rat spinal cords at weeks 4 and 6 following sciatic nerve injury (100×).

FIGS. 10A-10H depict photomicrographs of cresyl violet stain of dorsal grey horn of rat spinal cords at weeks 4 and 6 following sciatic nerve injury (100×).

FIGS. 11A-11H depict photomicrographs of NEU-N immunostaining of the spinal cords at week 4 and week 6 following nerve crush injury.

FIGS. 15A-15H show representative 10× photomicrographs of lumbar spinal cord from rats of all groups immunostained for GFAP at Week 4 and Week 6 following nerve crush injury.

Similar reference characters denote corresponding features consistently throughout the attached drawings.

DETAILED DESCRIPTION OF THE PREFERRED EMBODIMENTS

Figure 1A:
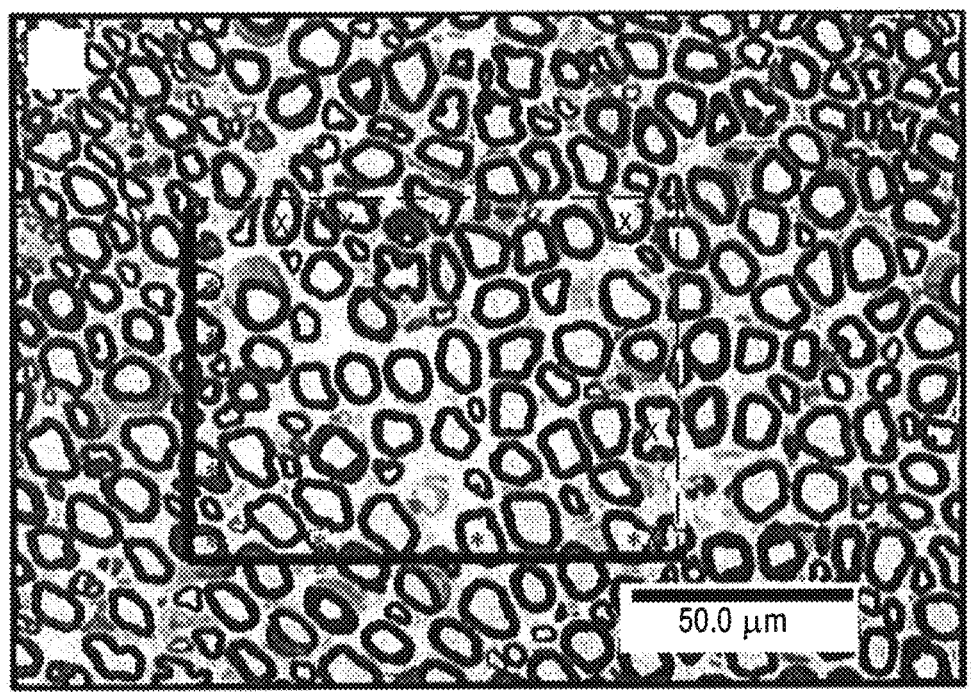
FIG. 1A shows a representative micrograph of a cross-section of sciatic nerve myelinated axons stained with toluidine blue.

A method of treating damaged nerves can include administering a therapeutically effective amount of a composition comprising a soluble protein fraction obtained from epidermal gel secretions of catfish to a patient in need thereof. The soluble protein fraction can include soluble proteins and lipids. The soluble protein fraction can include about 87% soluble proteins and about 13% lipids. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

A method of preparing a therapeutic composition from the epidermal gelatinous secretion of catfish can include collecting epidermal gel secretions (EGS) from the catfish and fractionating the epidermal gel secretions to obtain a soluble protein fraction comprising about 87% soluble proteins and about 13% lipids. The therapeutic composition can include the soluble protein fraction comprising about 87% soluble proteins and about 13% lipids.

The soluble protein fractions described herein can be obtained from the epidermal gel secretions (EGS) of Arabian Gulf catfish, such as (*Arius bilineatus* (*Valenciennes*)). The Arabian Gulf catfish naturally exudes a gelatinous secretion through its skin after the catfish is shocked, e.g., threatened or injured. For example, once a catfish is caught, it will struggle as it is towed to the surface with the fishing hook still in its mouth (as the catfish is a bottom dweller). As the fish reaches the surface, it struggles to defend itself and to escape the reduction in water pressure. This will cause the fish to secrete the EGS along with one or more contaminants, such as venom from its venom glands, faeces from its anal pore, vomit from its mouth and through its gills, and blood through its gills if the fishing hook catches the gill rays. Shocking the fish can also be accomplished by thermal shock, physical abrasions, or neural stimulation. The fish can be washed one or more times to remove contaminants. While the fish is still alive, the fish can be held through its gills to induce production of additional EGS. The EGS without any remaining contaminants on the skin can be collected by a gentle mechanical scraping or suction of the skin. Preferably, the EGS is immediately frozen, e.g., in dry ice, then cooled to −80° C. (deep freeze) or kept frozen in liquid nitrogen, to limit microbial growth and prevent biochemical decomposition.

The soluble protein fractions described herein can include a mixture of highly active biochemical and pharmacological components. These include, for example, a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. The soluble fraction can also include vaso-active components, phosphatases, including an acid phosphatase, a general esterase and a tyrosine specific esterase, and proteins with collagenase-like activities that cleave collagen into fragments. The soluble fraction can include a factor that activates phospholipase A2, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin. The lipids in the soluble fraction can include neutral lipids, phospholipids, and glycolipids. For example, the neutral lipids can include eicosanoids, cholesterol, triglycerides, fatty acids and steroids.

It should be understood that a therapeutic composition can be prepared from epidermal gel secretions of other species of catfish or any other aquatic or terrestrial creature (e.g., moray eels, slugs, and worms) that produces epidermal gel secretions having biologically active components similar to those present in the soluble protein fractions described herein.

As used herein, the term "about," when used to modify a numerical value, means within ten percent of that numerical value.

According to an embodiment, the method of preparing a therapeutic composition from the epidermal gelatinous secretion of catfish can include collecting epidermal gel secretions (EGS) from the skin of Arabian Gulf catfish (*Arius bilineatus* (*Valenciennes*)) and fractionating the EGS to provide a soluble protein fraction (SPF).

In an embodiment, the soluble protein fraction (SPF) can be extracted from the EGS by thawing the frozen EGS to a temperature ranging from about 4° C. to about 6° C. and mixing the thawed EGS with a suitable, non-toxic extraction buffer (e.g., saline in phosphate buffer at pH 7.5) to provide an extract. This step and all subsequent purification procedures can be carried out at about 4° C. to about 6° C. in the dark, unless otherwise indicated. The extraction buffer should not denature or affect the proteins in the EGS in any way. Preferably, the extraction buffer includes phosphate buffered saline having 0.05M ($NaH_2PO_4/Na_2HPO_4$) and 0.14M NaCl, pH 7.5. The thawed EGS can be mixed with an equal volume of the extraction buffer and homogenized, e.g., with an Ultra Truex (IKA) homogenizer. The homogenized extract can then be centrifuged to provide a soluble protein fraction (SPF) and an insoluble protein fraction. Centrifugation can separate insoluble filamentous proteins and cellular debris from a soluble fraction. Centrifugation can also remove contaminants such as microorganisms. The therapeutic composition is preferably free from insoluble components, as such components are not appropriate for intraperitoneal or sub-cutaneous injection and will not be absorbed and distributed if injected into an animal or human in this manner. Insoluble components can also clog the injection needle during injection. In an embodiment, the homogenate is centrifuged at 15,000 rpm for about ten to about fifteen minutes to provide the soluble fraction and the insoluble fraction. The soluble fraction can be freeze-dried and maintained at about −80° C. under nitrogen.

In an embodiment, the soluble protein fraction is freeze-dried and maintained at about −80° C. under nitrogen. The freeze-dried soluble fraction can be analyzed to determine a ratio of the concentration of soluble protein to lipids. In an embodiment, the powdered soluble fraction includes about 87% soluble proteins and about 13% lipids. If the powdered soluble fraction includes less than about 13% lipids, the powdered soluble fraction can be supplemented with lipids from an additional lipid fraction to achieve a soluble protein fraction having about 87% soluble proteins and about 13% lipids. The additional lipid fraction can be obtained from the freeze-dried EGS, as described herein. The therapeutic composition can include the soluble protein fraction having about 87% soluble proteins and about 13% lipids. The soluble fraction (SPF) (also referred to herein as "Fraction B") can be freeze-dried and stored at about −80° C. under nitrogen.

According to an embodiment, an additional soluble protein fraction can be separated from the insoluble fraction obtained from centrifugation. According to an embodiment, an insoluble fraction obtained from centrifugation in one fractionating cycle can be further fractionated in a subsequent fractionating cycle to provide yet another soluble protein fraction. According to an embodiment, the method can include about two to about four fractionating cycles of insoluble protein fractions, thereby providing a plurality of additional soluble protein fractions. The plurality of additional soluble protein fractions can be pooled and added to the original SPF obtained from the original fractionation of the EGS. The soluble protein fraction (SPF) or "Fraction B" can include the pooled soluble protein fractions. The SPF can be used for IP injection in an animal or human for treating damaged nerves. The SPF (Fraction B) can include lipids as well as soluble proteins (about 87% soluble proteins and about 13% lipids).

The concentration of lipids in the soluble protein fraction can be determined, e.g., by extracting the lipids from a freeze-dried soluble protein fraction and weighing the extracted lipids. If the soluble protein fraction includes about 87% soluble proteins, but less than about 13% lipids, additional lipids can be extracted directly from an EGS and added to the freeze-dried soluble protein fraction to increase the lipid percentage to about 13%. The additional lipids can be extracted from the freeze-dried original EGS. As described in detail, below, lipid extraction can be carried out in the dark and the extracted lipids can be stored under nitrogen until added to the soluble protein fraction. The lipids can be added with an organic solvent, e.g., isopropyl alcohol, to the freeze-dried soluble protein fraction to increase the lipid concentration to about 13% of the total soluble protein-lipid fraction. The organic solvent can be evaporated under vacuum at room temperature.

In an embodiment, if it is determined that the soluble protein fraction includes about 87% soluble proteins but less than about 13% lipids (which is generally the case), additional lipids can be provided by extracting lipids from the EGS with an organic solvent mixture. The additional lipids can be obtained from the freeze-dried EGS by extracting the lipids with an organic solvent mixture including chloroform: methanol: isopropanol (2:1:0.250, v/v) for about 72 hours on a stirring plate. The extracted lipids can then be obtained by filtration, e.g., using a vacuum pump and a Buchner funnel. The lipid extracts can be concentrated to dryness on a rotary evaporator at about 25° C. in the dark and weighed to ensure that the required weight of lipids to be added to the soluble protein fraction is achieved. The required amount of lipids can be dissolved in a suitable organic solvent, e.g., isopropyl alcohol, and added to the soluble freeze-dried protein fraction to increase the lipid fraction in the soluble protein fraction to about 13% of the combined weight of the proteins and lipids. The organic solvent can be evaporated under vacuum at room temperature in the dark to provide a freeze dried soluble protein fraction having about 87% soluble proteins and about 13% lipids of the total combined soluble proteins and lipids. The freeze dried soluble protein fraction (soluble proteins combined with the lipids) can be stored under nitrogen at about −80° C. until needed for injection.

The freeze dried soluble fraction can be maintained at about −80° C. (deep freeze) for long-term storage to prevent any unwanted chemical reaction. The enzymes in the fraction will not react against the components in the fraction if kept at about −80° C. during storing for lengthy periods of time under nitrogen. Also the lipids in the soluble protein fraction will be protected from decomposition if kept the same way in deep freeze until required for use. Nitrogen will not allow aerial oxygen to react with the lipids. The SPF is preferably stored in portions appropriate for a single injection at −80° C. It can then be thawed, kept in ice, and administered as needed.

A therapeutically effective amount of the composition including the SPF (Fraction B) can be administered to a patient to treat damaged nerves. A therapeutically effective amount can include about 3 mg to about 3.5 mg of the SPF (e.g., SPF including about 85% soluble protein and about 13% total lipids) per 100 gm of body weight of the patient (animal or human) to be treated. The therapeutic composition can be administered to a patient in need thereof, preferably by intraperitoneal (IP) or sub-cutaneous (SC) injection after dissolution of the SPF in saline, phosphate buffered saline, or other delivery system, such as nanotechnology delivery systems. The therapeutic composition can be combined with a pharmaceutically acceptable carrier. The therapeutic composition can be administered using other delivery methods, e.g., oral administration, provided that the composition is protected from the digestive effects of the elementary canal for oral administration, such as by encapsulation or nano-particle technology. Prior to injection of the soluble protein fraction, the freeze-dried soluble fraction can be dissolved in saline or phosphate buffered saline.

The therapeutic composition, prepared according to the present teachings, was administered to male Wistar rats with crushed sciatic nerves. As described herein, the results demonstrated that the SPF treatment alleviated neurobehavioral deficits and stimulated regeneration of the axons and histo-morphological alterations following nerve injury. The SPF treatment also protected spinal neurons and enhanced subcellular recovery after peripheral nerve injury, thereby improving nerve regeneration.

Accordingly, the SPF composition can be administered to a patient to treat damage to the nervous system resulting from crush injury or disease. In an embodiment, a concentration of 3 mg SPF/kg of human or animal body weight can be administered to a patient in need thereof. Prior to the injection of SPF, the SPF can be sterilized with ultrasound or by passing through a membrane filter.

The SPF composition can be administered to a patient to accelerate regeneration of crushed nerves and damages sustained due to the crush and bring them back to functionality as assessed by recovery of their functions. The composition can be used to treat nerve compression injury or neuropathy that are known to be associated with disease states such as diabetes, glaucoma, or myelin-related neurodegenerative diseases, where nerve function deteriorates as these severe chronic disorders progress. Pre-clinical studies of peripheral nerve injury have identified a crucial role for neural tissue inflammation in the onset of neuropathic pain. Activation of immune and immune-like glial cells at the site of nerve injury, spinal cord, and dorsal root ganglia give rise to the production of proinflammatory cytokines, which may induce the discharge of neural ion channels and nociceptors, alter the activity of glial cells supporting neural function or induce the degeneration of neurons and Schwann cells. It is believed that the proteins and lipids in the present composition act synergistically to provide neuroprotective and neuroregenerative properties to alter, regulate, control and/or render the injured peripheral nerve microenvironment milieu towards more permissive rather than inhibitory effect. This in turn may speed up the way to neuronal survival and axonal regeneration by modulating the anti-inflammatory factors.

The SPF is preferably stored in portions appropriate for a single injection at −80° C. It is then thawed and injected as needed.

A therapeutically effective amount of the SPF can include about 3 mg to about 4 mg of the SPF per kg of body weight of the animal or human to be treated.

The following examples illustrate the present teachings.

Example 1

Preparation of SPF and Calculation of Soluble Protein in Solution

EGS was collected from the catfish skin and kept at −80° C. until use. Frozen EGS was thawed to 4° C., mixed with an equal volume of extraction buffer [phosphate buffered saline (PBS), 0.05 M containing ($NaH_2PO_4/Na_2HPO_4$) and 0.14 M NaCl, pH 7.5], and homogenized with an Ultra Truex (IKA) homogenizer. This step and all subsequent purification procedures were carried out at 4'C unless otherwise indicated. The homogenate was centrifuged at 15,000 rpm for 10-15 min. The supernatant was collected, and the pellet (insoluble protein etc.) was re-extracted with extraction buffer (2-4 times). Each time, the soluble fraction was separated by centrifugation as described above, and the two extracted fractions were pooled. The combined extracted fractions provided the soluble protein fraction (SPF)

To find the concentration of catfish soluble proteins in the SPF, the SPF was diluted with PBS (1:50). 0.1 ml of the diluted sample was mixed well with 5 ml of Coomassie Brilliant Blue solution and kept in tubes at room temperature for about 10 minutes. Absorbance was read at 595 nm for the sample, and its protein concentration was determined by comparing its absorbance against absorbance for a standard curve for different bovine serum albumin concentrations.

The SPF was then dissolved in the extraction buffer to be injected.

Example 2

Nervy Regeneration

Experiments for nerve regeneration involved two major procedures. The first one was to cause damage to the sciatic nerve through crushing the nerve, to be followed by intensive and stringent procedures of evaluation of the extent of the resulting damage. The second treatment involved treating the animals with crushed sciatic nerves with SPF, to be followed by intensive research work to demonstrate nerve regeneration and recovery of nerve functions upon treatment of the animals with SPF.

A total of 100 male Wistar rats (weight 250-300 g) were used in the study. For the first experiment, equal numbers of animals (n=10/group) were randomly assigned to the following 6 treatment groups: I: NAIVE (no surgery or sciatic nerve injury); II: SHAM (SHAM-injury surgical control group): III: CRUSH (saline-treated, crushed sciatic nerve); or CRUSH SPF-treated groups distributed as follows VI: CRUSH+O.5×SPF (IP), V: CRUSH+1× (SC) and VI: CRUSH+2×SPF (SC) groups. The SPF-treated animals were administered intraperitoneal (IP) or subcutaneous (SC) injections of SPF (O.5X=3 mg/kg; X=6 mg/kg; 2X=12 mg/kg) once a day for 14 days starting 1 hour after sciatic nerve injury. In the second experiment, forty rats were used. Equal numbers of animals (n=10/group) were randomly assigned to the following four treatment groups: I: SHAM (SHAM—surgical control group); II: CRUSH (saline-treated); III CRUSH+1×SPF (IP) and VI: CRUSH+1×SPF (SC) groups.

One group was left as a control group (Sham), where the sciatic nerve was exposed, then the wound was sutured and then the animal was not treated. The second group had the sciatic nerve exposed, crushed sutured and left without treatment (control animals). The third group had the sciatic nerve exposed, crushed, the wound was sutured, then the animal was treated with the preparation (SPF) once a day for 14 days through inter peritoneal (IP) injection, or subcutaneous injection (SC).

Specific aims of the experiments included: assessing the pain tolerance in rats with crushed sciatic nerve following treatment with SPF; evaluating the functional motor outcomes in animals with a crushed sciatic nerve injury following treatment with SPF; obtaining an estimation of total myelinated axon number, myelin thickness and myelin density using stereological measurements; assessing the histopathological changes (using histological and immuno-histochemical techniques) in rats with crushed sciatic nerve following treatment with SPF; and relating the results of these research experiments to the recorded findings of previously treated human neurological disorders with catfish skin preparation (CSP) components.

The rats in all experimental groups were evaluated for motor neurobehavioral functions 2 weeks preoperatively and during 1 st, 3rd, and 5th post-surgery weeks; whereas for sensory functions the animals were tested 1 week preoperatively and during 2nd, 4th, and 6th post-surgery weeks as described earlier. All tests were repeated three times (with 3 min.-20 min. interval) for each rat. Mean of 3 measurements was used as data for that rat, for calculating the group mean for further statistical analysis. Investigators were blinded to all treatments in all experiments.

Several tests of reflexive sciatic nerve function (foot position, toe spread, extensor postural thrust [EPT], hopping and Rotarod tests) were conducted. Briefly, EPT was measured by calculating the functional deficit in this feature; thus, the higher value indicated a poor outcome. The hopping reflex test was done to test several integrated functions. Each leg of the rat was suspended above a horizontal surface and was slowly moved laterally, with one foot touching the table surface at a time. The rat was scored based on whether it hopped on the foot that was contacting the table surface (1 for hopping, 0 for no hopping) (Thai hammer et al., 36).

The rota rod test is widely used to evaluate the motor coordination of rodents, in which the animal is placed on a horizontal rod that rotates around its long axis; the animal must walk forward to remain upright and not fall off. Rotarod performance was measured using Rotarod test (47750—Rat Rotarod NG, Ugo Basile SRI., Varese—IT AL Y) set at the acceleration mode (initial speed starts from 5 rpm/min; while maximum speed set at 45 rpm/min). The rat was held by the tail and placed on the rotating rod, facing away from the direction of rotation, so it has to walk forward to stay upright. Ten seconds after putting the rat on the rod, the acceleration was started, and the speed at which the rat falls off was noted. The mean speed at fall was recorded; rather than using the maximum speed, as it corrects for the extra practice the rat received during the failed runs, which is assumed to assist performance. Time and acceleration speed were recorded (Monville et al., 37). The Rotarod time latency that the animal falls is indicated on the V-axis.

Tactile allodynia, mechanical hyperalgesia, hotplate analgesia and tail flick neurobehavioral tests were conducted on all rats to assess the sensory function as follows: 1-Tactile allodynia: The von Frey using Hargreaves's method (37370—Plantar Test; Hargreaves Apparatus, UGO Basile SRL, Italy) was used to evaluate the sensitivity of the skin to tactile stimulation as described previously. Mechanical allodynia thresholds from the right and left hind limbs were measured in different animal groups, and then the withdrawal reflex latencies (mean±SO) were calculated. 2—Mechanical Hyperalgesia: Paw pressure thresholds expressed in grams were measured using Analgesia Meter (Model 21025, UGO Basile SRL, Italy). Three consecutive mechanical nociceptive threshold values were measured for each hind limb, and the mean and standard deviation (SO) of the paw pressure latencies were calculated. 3. Thermal nociception: Thermal nociception was measured by a modified hot plate test (51° C.; 35100—Hot Cold Plate, UGO Basile SRL, Italy). The withdrawal response threshold (WRT) defined as the time elapsed from the onset of hotplate contact to the withdrawal of the hind paw and was characterized as a brief paw flick recorded to the nearest 0.1 see; a standard cutoff latency of 35 sec was employed to prevent tissue damage. A normal response is considered withdrawal within 12 seconds. The WRT was measured for both left and right hind limbs. Each hind limb was tested thrice, with 20 minutes between tests to avoid sensitization. Then the withdrawal response latency (WRL) was calculated, and the three latencies were averaged to obtain a final result for each animal. 4. Tail flick: The spinally mediated nociceptive thresholds were determined using Analgesia Meter Apparatus (Model 7360, UGO Basile SRL, Italy). The amount of time taken by the rat to move (flick) its tail away from the heat was recorded. A cut-10 off time of 30 seconds was used to prevent tissue damage.

All behavioral data were analyzed by 2-way repeated measures ANOVA followed by Bonferroni's F- and Fisher least significant difference (LSD) comparison post hoc test or Student t-test, as appropriate. All statistical analysis was performed using SPSS (version 21.0, IBM Corp.) and p values less than 0.05 were considered statistically significant.

At the end of Week 4 and Week 6 postoperative periods, three animals from each experimental group were randomly selected for histopathological and morphometric evaluation as previously described. Briefly, animals were anesthetized, the right sciatic nerve and lumbar spinal cord were dissected and fixed by immersion overnight at 4° C., in a mixture of 2% paraformaldehyde and 2% glutaraldehyde in 0.1 M phosphate buffer, pH 7.4. On the following day, the 5 mm length of sciatic nerve specimens distal to the crush site (or corresponding location in NAIVE and SHAM rats) were rinsed in phosphate buffer (pH 7.4) twice, post-fixed in 1% osmium tetroxide, dehydrated through a graded alcohol series, immersed into propylene oxide and embedded in Epon resin. From each tissue block, semi-thin (1I.1m) cross-sections were cut using RMC MT-7 ultramicrotome (Research and Manufacturing Co, Tucson, Ariz., USA), and stained with 1% toluidine blue for light microscopic histopathological examination and morphometric analysis. For electron microscopy, ultrathin sections were cut from the same tissue blocks and processed for EM analysis.

Stereological analysis of the sciatic nerves was performed by an experimenter blinded to the groups according to principles described previously. Stained sections of the sciatic nerve were digitally photographed using Olympus OP71 digital camera (Nikon COOLPIX 4500) with 100× oil immersion objective (total magnification 1000×). From each nerve, ten sections were selected for photography, and from each section 10 photographs were taken from randomly chosen fields. No. of nerve fibers/field in each photomicrograph were counted as previously described (FIGS. 1A-1E). For calculating the myelin thickness (m=[D-d]/2) and g-ratio (d/D), the axon diameter (d) and the nerve fiber diameter (D) were measured automatically using Image-Pro Plus 6.0. Thickness measurements from all sampled axons were averaged to obtain the mean myelin thickness. Quantification was done by Image-Pro Plus image analyzing software (Version 6.0.0.260 for Windows 2000/XP Professional; Media Cybernetics). The unbiased counting frame method with a square sample area (900 $\mu m^2$) was used to obtain an estimation of total axon number impartially from nerve cross-section. A counting frame was placed on the image, and the sampling area was selected in a systematic uniform random manner. The nerve profiles marked with a yellow asterisk along the solid yellow lines (inclusion lines) were included in the counts, but not the profiles marked with an X touching the dashed red line (exclusion lines). A mean sampling of each sectioned nerve profile was done in 70×70 μm step size in a systematic random manner. This ensured that all locations within a nerve cross-section (1 μm-thickness) were equally represented and that all axon profiles were sampled with equal probability regardless of shape, size, orientation and location (FIGS. 1A-E).

Images were viewed on a 15-inch Samsung SyncMaster 5005 color monitor. The axon diameter (d) and the nerve fiber diameter (0) were measured automatically using Image-Pro Plus 6.0 image analysis software and were used to calculate myelin thickness. The thickness measurements acquired from all sampled axons were then averaged to obtain the mean myelin thickness. Myelin sheath thickness was calculated as the difference between the fiber diameter (0) and the axon diameter (d), divided by two (m=[0−d]/2). The number of axons in the image (N) was calculated by using the following equation: N=(A×n)/a, where "n" is the number of axons in a small square, which is identified through Image-Pro Plus; "a" is the area of the small square, and "A" is the total area of the image (length×width). Also, the perimeters of the myelinated axons were measured, and the average axon perimeters were calculated and compared between groups.

Images of the distal portions of the right sciatic nerve obtained from 3 rats per group were analyzed. A total of 10 images from each section were digitized and stored in uncompressed tagged image file format (TIFF) with 24-bit RGB class and 640×480-pixel resolution. All data are presented as the mean±standard deviation of the mean (SEM). All calculations and all statistical procedures were performed using SPSS (version 21.0). The group values were compared using a Mann-Whitney U-test. A p value of less than 0.05 was considered significant.

For protein quantification of myelin basic protein (MBP), glial fibrillary acidic protein (GFAP) and growth associated protein 43 (GAP-43), Western blot was performed as described previously. Briefly, the sciatic nerve tissues from 3 rats/group were homogenized in RIPA buffer, (50 mM Tris (pH 7.4), 150 mM NaCl, 1% NP-40, 5 mM EOTA, 0.5% sodium deoxycholate, 0.1% SOS, protease inhibitor, 2 mM Benzamidine, PMSF). Proteins were isolated and dissolved in PLB-TCEP provided with the NucleoSpin® RNA/Protein kit. Protein concentrations were determined using the trichloroacetic acid method. Then, equal amounts of protein (10-14~g) were loaded on each lane, separated by 8% SOS-poly acrylamide gel electrophoresis (SOS-PAGE) and blotted onto a nitrocellulose membrane for 1 h at 75V. Membranes were washed in PBS (3×5 min) then blocked with 5% fat-free milk solution in PBS for 30 min. Subsequently, the nitrocellulose membranes were incubated with the anti-MBP (0-18: sc-13912, Molecular weight-14-22; Santa Cruz Biotechnology, Inc., Heidelberg, Germany), anti-GF AP (antibody (ab7260)—Abeam Biochemical®, Cambridge, Mass., USA) and anti-GAP-43 (Antibody (B-5): sc-17790—Santa Cruz Biotechnology) diluted in 5% milk in PBS-Tween overnight at 4° C. Next, membranes were washed with PBS and incubated with the anti-mouse IgG secondary antibody conjugated to horseradish peroxidase (Goat anti-mouse IgG-HRP: sc-2005 and donkey anti-rabbit IgG-HRP: SC-2313; Santa Cruz Biotechnology, Inc., Heidelberg, Germany) for two hours at room temperature. After washing the membranes with PBS (3×5 min), they were treated with chemiluminescence reagent and then exposed to X-ray film, and the film was developed. Actin was used as loading control. All bands labeled with the anti-MBP antibody, GFAP antibody and GAP-43 antibody (n=3 sciatic nerves/group) were scanned, and their density was quantified by Densitometer GS-800, and normalized with the actin band density.

While collecting the sciatic nerve, lumbar spinal cords were also dissected and fixed by immersion overnight at 4° C., in a mixture of 4% paraformaldehyde and 0.1% glutaraldehyde in 0.1 M phosphate buffer, pH 7.4. Every 15th section of the spinal cord was stained for Cresyl Violet staining and immunostained for neurons using Primary antibodies for NeuN, GFAP and GAP 43. 5~m thick paraffin sections of the spinal cord, were cut and mounted on Poly-L-lysine coated slides and kept overnight for drying. The tissue sections were deparaffinized in xylene and rehydrated in graded series of alcohol from Absolute alcohol to 50% alcohol and then taken to water. Endogenous peroxidase activity was quenched by treating sections with 3% hydrogen peroxide for 15 min followed by 30 minutes incubation in 50 mM glycine and 0.1% sodium borohydride and then washed with PBS (Ph 7.4).

Non-specific binding of antibodies was blocked by treating the sections with 5% normal goat serum. Sections were incubated with primary antibodies (Anti-NeuN, Clone A60, Mouse Monoclonal Antibody, Cat # MAB377, Millipore. Billerica, Mass., USA), Anti-GFAP antibody (GA-5: sc-58766, Mouse MonoclonalSanta Cruz Biotechnology) or Anti-GAP-43 Antibody (B-5: sc-17790—Santa Cruz Biotechnology) overnight at 4° C. Sections were then washed with PBS and treated with biotinylated goat anti-mouse IgG [(1:200), Vector Labs, Burlingame, Calif., USA)] and 1% normal goat serum for 2 hrs at room temperature. Slides were then washed three times in PBS and treated with Avidin-Biotin Complex (Vector Labs, PK-6200, Burlingame, Calif., USA) along with 0.1% Tween 20 for 1 hour at room temperature.

Sections were color developed with 3-diaminobenzidine as a chromogen (DAB kit, SK-41 00, Vector Labs, Burlingame, Calif., USA), for 30 sees or until the desired brown color was obtained as seen under the microscope. The slides were washed with distilled water, counterstained in hematoxylin for 5 minutes, followed by bluing under tap water for 5 minutes. The slides were dehydrated by passing through graded series of alcohol from 50% to Absolute ethanol and cleared in xylene.

Finally, a coverslip was mounted on top of sections using DPX mountant for histology. For Cresyl violet staining, sections were mounted on gelatin-coated slides and air-dried overnight. Sections were hydrated in graded ethanol and stained with 0.1% cresyl violet stain. Slides were dehydrated in graded ethanol, cleared in xylene and mounted with DPX mountant for histology (44581, Sigma).

The number of Neun labeled neurons in the ventral and dorsal grey horns of the spinal cord were counted using Cell Sens Dimension software. From each rat, ten sections were selected for neuron quantification. The region of the spinal cord under analysis was focused at 40× magnification, and an image was transferred to a computer monitor with a high-resolution digital Nikon camera attached to an Olympus microscope (DP-72). The total number of neurons in the entire ventral and dorsal grey horns were counted. Slides were coded to avoid observers' bias. The mean number of neurons per section was calculated for statistical analysis.

The GF AP and GAP-43 immuno-reactive staining intensity was measured with Cell Sens Dimension software. From each rat, ten sections were randomly selected for intensity measurement. The total intensity in the entire ventral and dorsal grey horns was measured, and the mean GFAP and GAP-43 immunoreactive intensity per section were calculated for statistical analysis. H. Statistical Analysis:

The NeuN, GFAP and GAP-43 immunohistochemical data were analyzed by oneway ANOVA followed by Bonferroni's F-test and Fisher least significant difference (LSD) comparison post hoc test to determine differences in individual baseline values. All statistical analysis was performed using SPSS (version 21.0, IBM Corp.); p values less than 0.05 were considered statistically significant.

The hind paws of the SHAM animals displayed normal clinical appearance following surgery. Also, the skin and muscle wounds did not hamper the animal's gait during the experiment. During the first week, the foot and toes of the hind paw in the CRUSH rats were strongly flexed. The animals were also incapable of standing on their operated hind paw. Partial weight bearing was observed in the CRUSH rats starting from the second week. In contrast, the SPF-treated animals displayed observable improvement in clinical picture and weight bearing over the subsequent weeks compared to the CRUSH group.

Figure 2A:
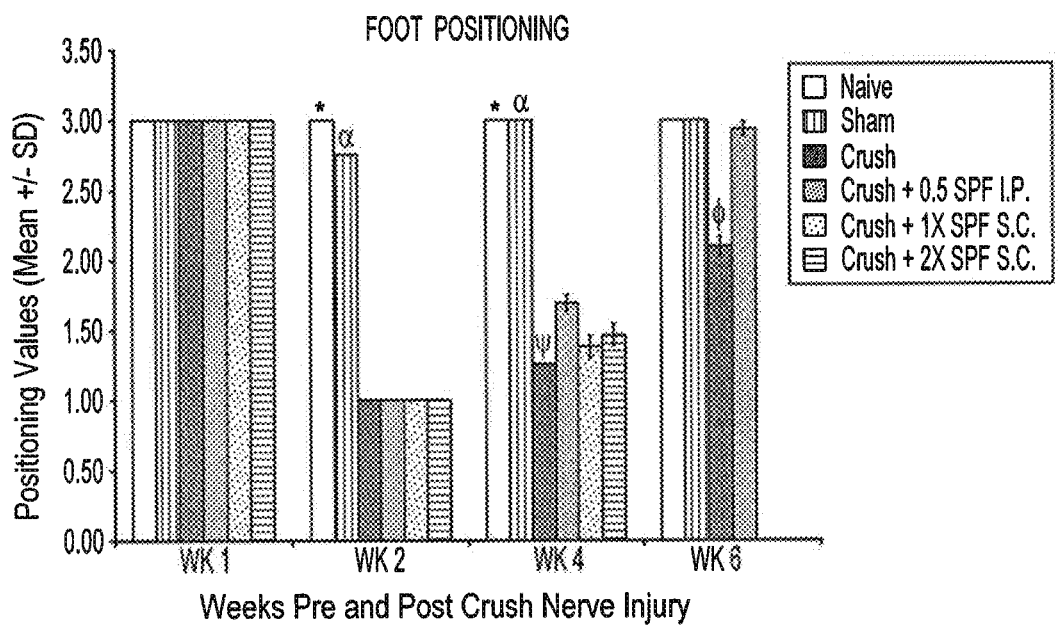
FIG. 2A is a graph showing the effects of sciatic nerve crush on foot position values in CRUSH+SALINE.
Figure 2B:
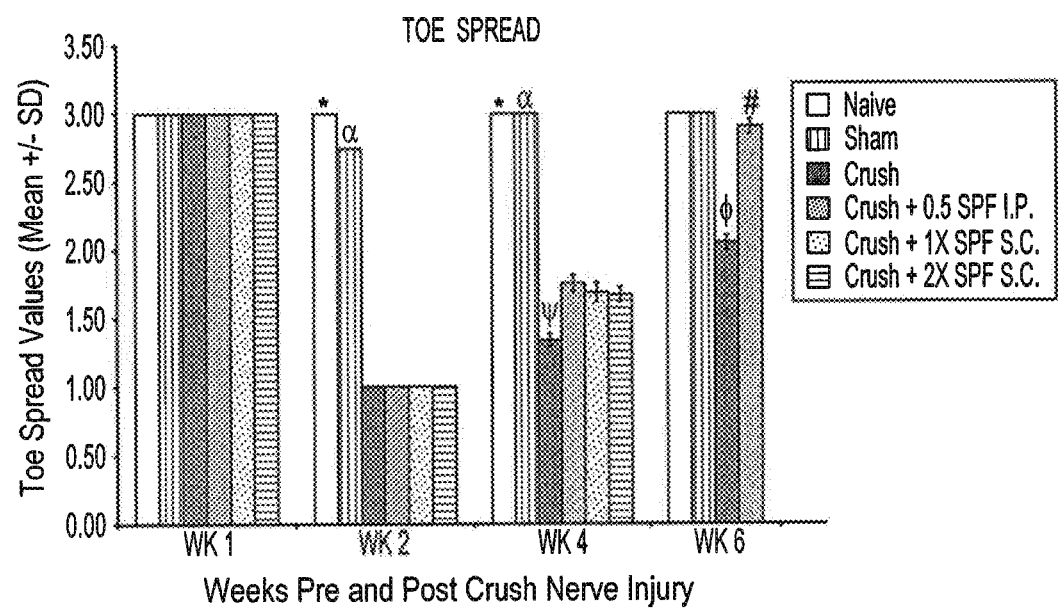
FIG. 2B is a graph showing results of analysis of toe spread outcome.

Sciatic nerve crush produced significant (p<0.000) decrease of foot position values in CRUSH+SALINE group at week 1, week 3 and week 5 post-surgery weeks compared to NAIVE and SHAM groups (FIG. 2A). 0.5×loP. and 2×S.C. SPF treatments significantly (p<0.001) increased the foot position values at Week 3 compared to CRUSH+SALINE group. Likewise, the mean values of the foot position analysis were significantly (p<0.000) higher in CRUSH+0.5×I.P. SPF-treated at Week 5 (FIG. 2A). The CRUSH+0.5× loP. SPF-treated animals mean values of the foot position were similar to NAÏVE and SHAM groups. Like the foot position, significant recovery (p<0.000) of the toe spread started at the end of week 3 in the CRUSH+0.5× loP, CRUSH+1×S.C. and CRUSH+0.5×S.C. SPF-treated groups (FIG. 2B). At the end of Week 5, the CRUSH+0.5× I.P SPF-treated group demonstrated significant (p<0.000) foot position recovery compared to CRUSH animals. However, the improvement of CRUSH+0.5×J.P. SPF-treated animals was still lagging behind (p<0.04) the NAÏVE and SHAM groups (FIG. 2B).

Figure 2C:
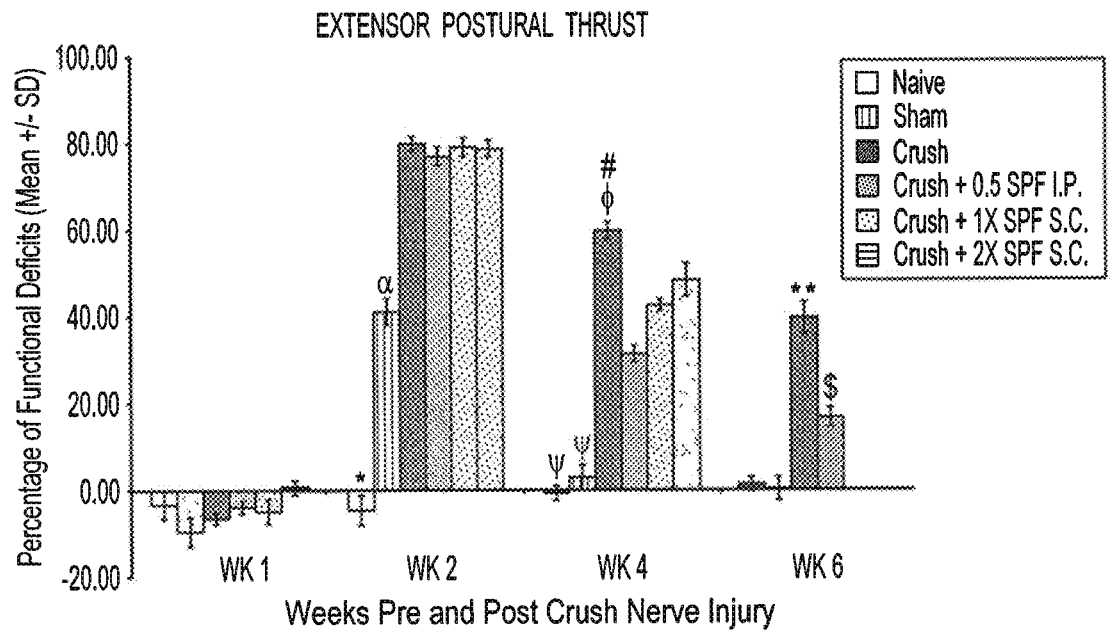
FIG. 2C is a graph showing evaluation of functional recovery as measured by extensor postural thrust (EPT) following crush injury and SPF treatments.

FIG. 2C shows the evaluations of the functional recovery as measured by extensor postural thrust (EPT) following crush injury and J.P. and S.C. SPF treatments. The SHAM and the SPF-treated groups displayed significant (p<0.000) EPT deficits at Week 1 following crush injury. Further, the SPF-treated groups lost significant (p<0.000) EPT compared to SHAM animals (approximately 80% and 40% deficits, respectively) at Week 1 following crush injury. At Week 3 post-injury, the CRUSH+SPF-treated groups displayed significant (p<0.000 CRUSH vs. 0.5×SPF (J.P.) and 1×SPF (S.C.)-treated groups; p<0.03 CRUSH vs. 2×SPF (S.C.) treated group EPT recovery. The CRUSH+0.5×SPF(J.P.)-treated group displayed more than 85% improvement in motor EPT recovery (p<0.000) compared to CRUSH (approximately 60% recovery) by the end of Week 5 following nerve injury.

Figure 2D:
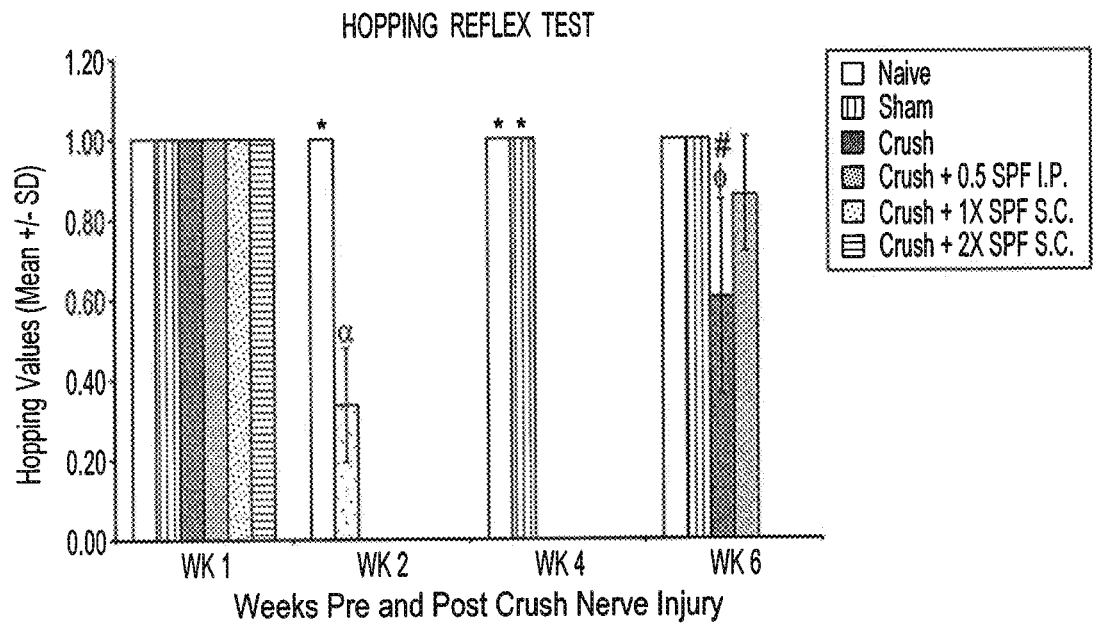
FIG. 2D is a graph showing differences in the mean values of the hopping test outcome among the experimental animal groups.
Figure 2E:
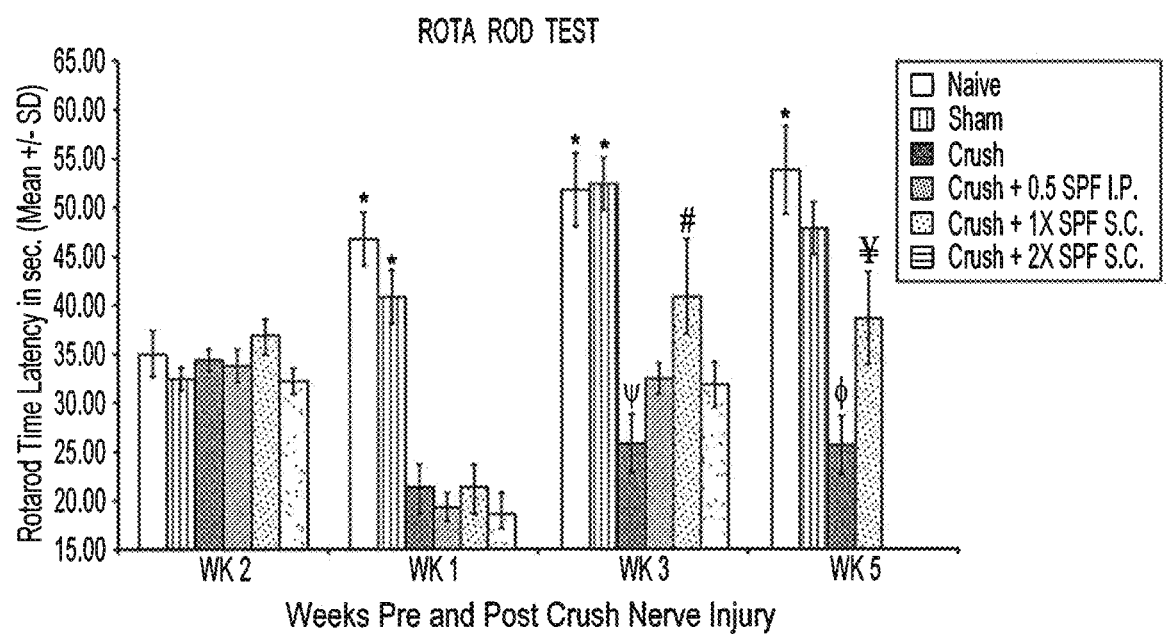
FIG. 2E is a graph showing rotarod performance measured using Rotarod test set at the acceleration mode (initial speed starts from 5 rpm/min; while maximum speed set at 45 rpm/min) one week before the nerve injury and at week 1, 3 and 5 post-injury. The Rotarod time latency that the animal falls is indicated on the Y-axis.

The results of the hopping test (FIG. 2D), which examines several integrated sensory and motor functions, demonstrated significant (p<0.000) early recovery in the SHAM animals compared to the NAIVE group at the end of Week 1. However, the CRUSH+SPF-treated animals showed did not show any hopping response at Week 1 and Week 3. At Week 5 post-nerve injury, the CRUSH and CRUSH+0.05× SPF (J.P.)-treated group demonstrated hopping response (approximately 60% and 90%, respectively). The hopping response of the CRUSH+0.05×SPF (J.P.)-treated group was similar to the NAIVE and SHAM groups and statistically (p<0.03) much higher than CRUSH animals (FIG. 2I)).

The Rotarod acceleration mode performance test displayed a significant decrease in the time latency of the CRUSH and CRUSH SPF-treated groups (approximately 20 sec) compared to NAIVE and SHAM animals (nearly 50 and 40 sec, respectively) at Week 1 post-nerve injury. At Week 3 following the surgery, the CRUSH+1×SPF (S.C.) (p<0.004) demonstrated higher time latency on the Rotarod compared to CRUSH group. Meanwhile, the Rotarod performance of the CRUSH+0.5×SPF (J.P.) animals displayed significantly (p<0.001) higher time latency (approximately 40 sec) compared to the CRUSH group (nearly 25 sec) at Week 5. The CRUSH+0.5×17 SPF(I.P.) animals showed no significant difference to SHAM group (approximately 47 sec).

Figure 3A:
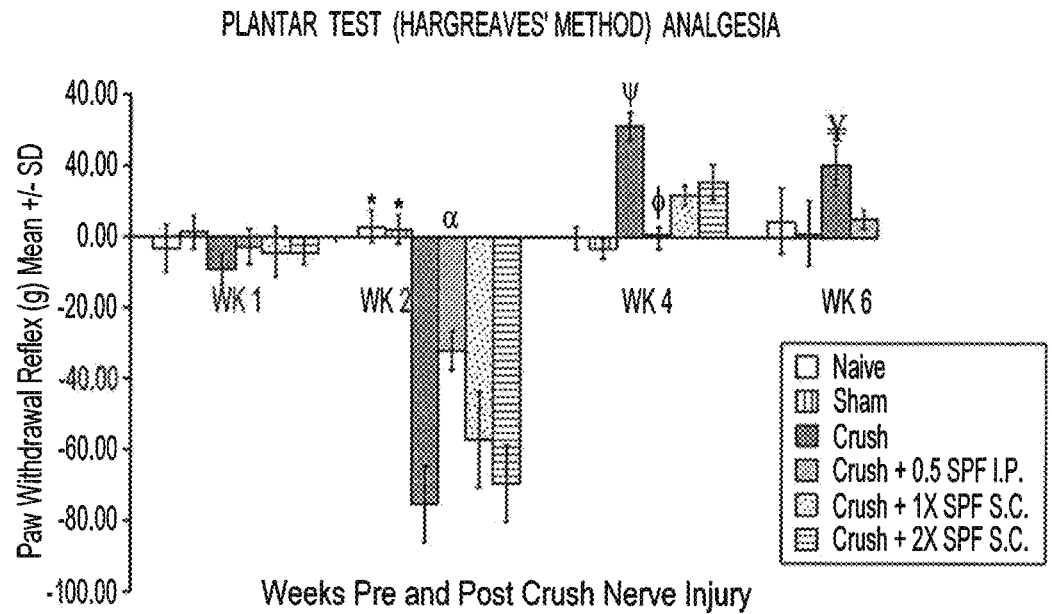
FIG. 3A is a graph showing Plantar Test using Hargreaves's method to measure tactile allodynia.

Several neurobehavioral sensory tests were performed, including assessment of allodynia, mechanical hyperalgesia, thermal hyperalgesia, and tail flick latencies. The time course graph displaying the assessment of allodynia time latency of the different experimental groups before and after sciatic nerve injury is shown in FIG. 3A. The CRUSH and the CRUSH SPF treated groups showed significant (p<0.000) decrease in analgesia planter test at Week 2 post-injury. Week 4 postinjury, the CRUSH, and CRUSH+1×SPF (S.C.) groups displayed an increase in analgesia. However, CRUSH+0.5×SPF (J.P.) group showed significant decrease compared to CRUSH (p<0.000), CRUSH+1×SPF (S.C.) and CRUSH+2×SPF (S.C.) treated animals (p<0.008). The CRUSH+0.5×SPF (J.P.) stayed significantly different compared to the CRUSH group at Week 6 following nerve injury. The CRUSH+0.5×SPF (J.P.)-treated group displayed significant (p<0.02) decrease compared to CRUSH animals at Week 6 post nerve injury. Moreover, it was noticed that the latency times of the CRUSH+0.5×SPF (J.P.) animals followed that of NAIVE and SHAM groups).

Figure 3B:
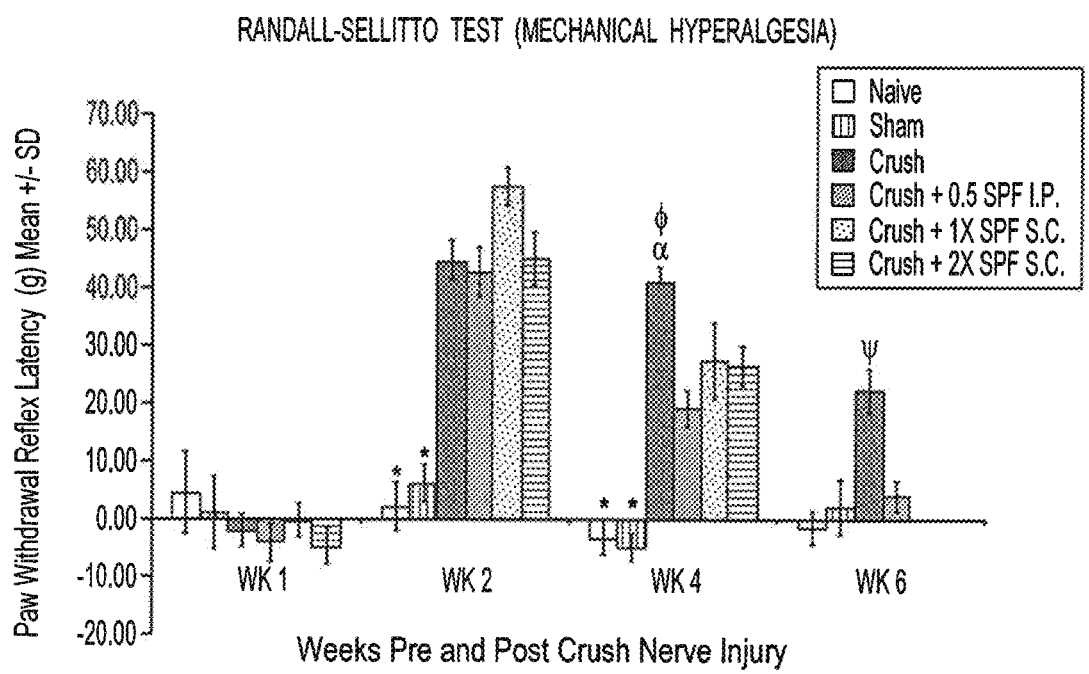
FIG. 3B is a graph showing the time course of paw pressure latency (mechanical hyperalgesia) from different experimental groups tested at one week before the crush injury surgery and week 2, week 4 and week 6 post-injury induction.

Likewise, using paw pressure latency test which measures mechanical hyperalgesia, the CRUSH and the CRUSH SPF treated groups showed significant (p<0.000) increase in mechanical hyperalgesia test at Week 2 and Week 4 post-injury compared to NAIVE and SHAM groups (FIG. 3B). The CRUSH+0.5×SPF (J.P.), CRUSH+1×SPF (S.C.) and CRUSH+2×SPF (S.C.)-treated groups showed a significant (p<0.000, p<0.01 and p<0.01, respectively) decrease in paw withdrawal reflex latencies compared to the CRUSH group at Week 4. At Week 6 following nerve injury, CRUSH+0.5× SPF (I.P.)-treated animals displayed significant (p<0.000) decrease in paw pressure latency indicating back to normal mechanical hyperalgesia values.

Figure 3C:
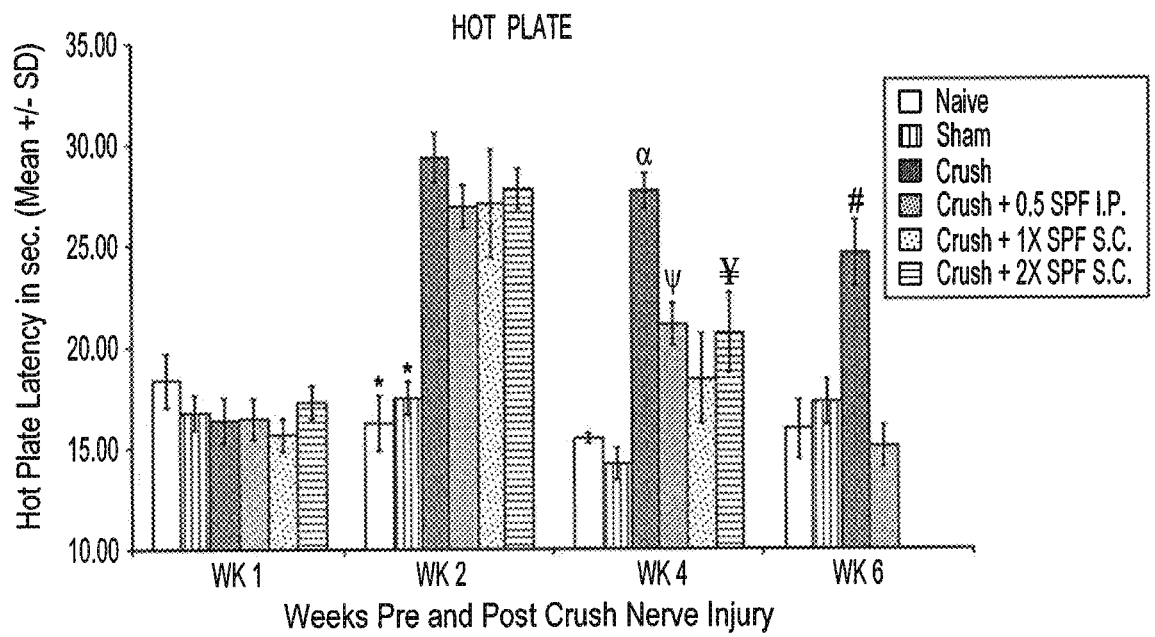
FIG. 3C is a graph showing the time course of hot plate latency.
Figure 3D:
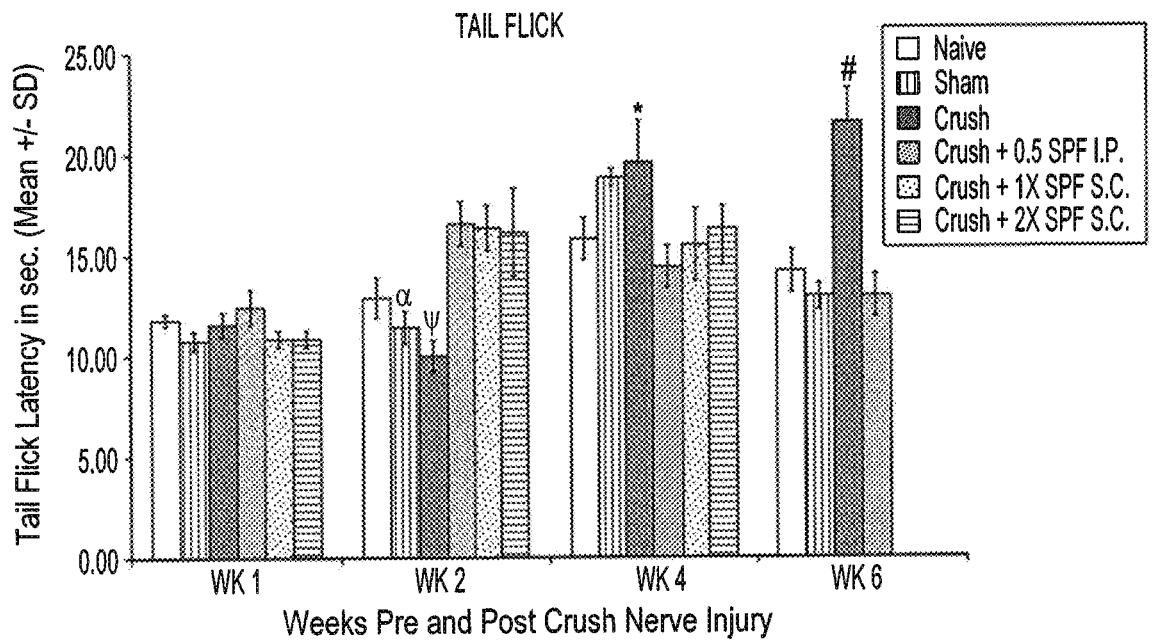
FIG. 3D is a graph showing time course of tail flick withdrawal latency (mean±SEM).

Nerve crush injury produced a significant (p<0.000) delay in the hot palate latency in the CRUSH and CRUSH SPF-treated groups at Week 2 (FIG. 3C). The CRUSH SPF-treated groups showed a significant (p<0.000) thermal nociceptive recovery starting at Week 4. At week 6 post-injury, the CRUSH+0.5×SPF (I.P.) animals maintained the thermal nociception recovery comparable to control groups. The CRUSH group displayed significant (p<0.001) higher hot plate latency compared to NAIVE, SHAM and CRUSH+ 0.5×SPF (IoP.) groups at Week 6 following nerve injury (FIG. 3C). The time course of tail flick withdrawal latencies of the different groups is shown at Week 3, 4 and 6 post-injury in FIG. 3D. The data shows fluctuation in the values of tail flick withdrawal latencies among the different groups at Week 2 and Week 4 following surgery. The CRUSH+0.5×SPF-treated group showed significantly (p<0.006) tail flick withdrawal latency recovery compared to CRUSH group by the end of Week 4 post-surgery. This central nociception normalization was sustained until the end of the experiment. Whereas CRUSH animals continued to display significant (p<0.000) increase in the tail flick withdrawal latency compared to controls and CRUSH+0.5× SPF (IoP.) groups. Importantly, there was no difference between CRUSH+0.5×SPF(I.P.) group and the NAIVE and SHAM groups at Week 6 post nerve injury (FIG. 3D).

Figures 4A, 4B, 4C:
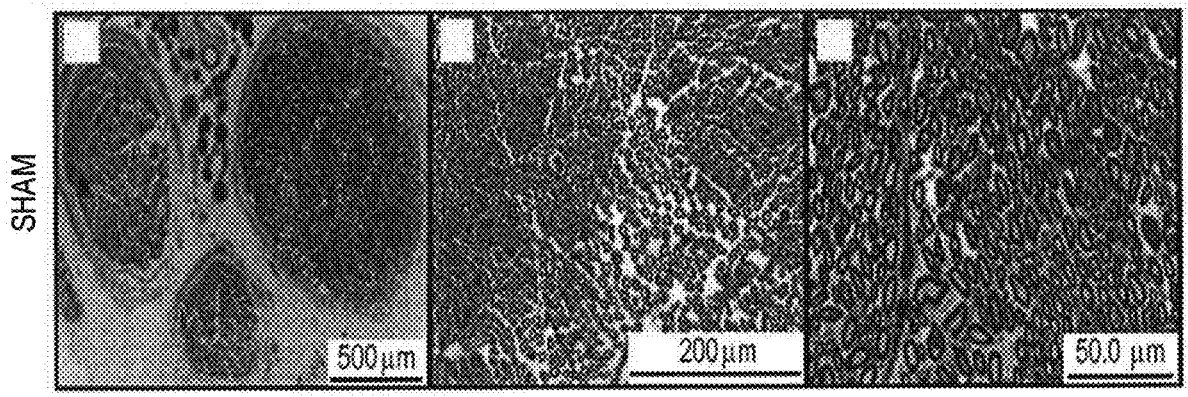
FIGS. 4A-4L show toluidine blue stained photomicrographs of semi-thin transverse sections of sciatic nerves obtained from animals in the SHAM (FIG. 4A, FIG. 4B and FIG. 4C), CRUSH (FIG. 4D, FIG. 4E and FIG. 4F), CRUSH+0.5×SPF(I.P.) (FIG. 4G, FIG. 4H and FIG. 4I) and CRUSH+1×SPF(S.C.) (FIG. 4J, FIG. 4K and FIG. 4L) groups at Week 4 following nerve injury (Column I; 10×, Column II, 40× and Column III, 100×). Sciatic nerve sections of CRUSH+0.5×SPF(I.P.) are shown in FIG. 4G, FIG. 4H and FIG. 4I and sciatic nerve sections of CRUSH+1× SPF(S.C.) are shown in FIG. 4J, FIG. 4K and FIG. 4L.
Figures 4D, 4E, 4F:
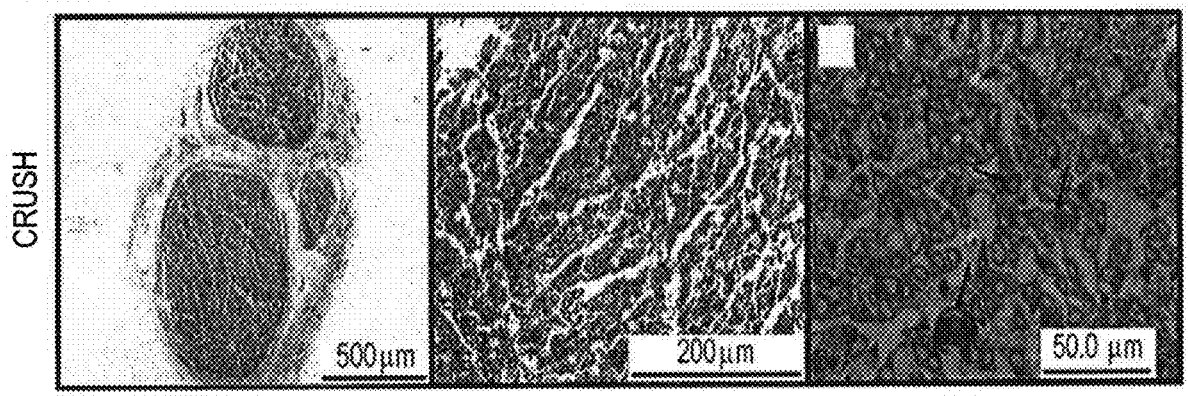
Figures 5G, 5H, 5I:
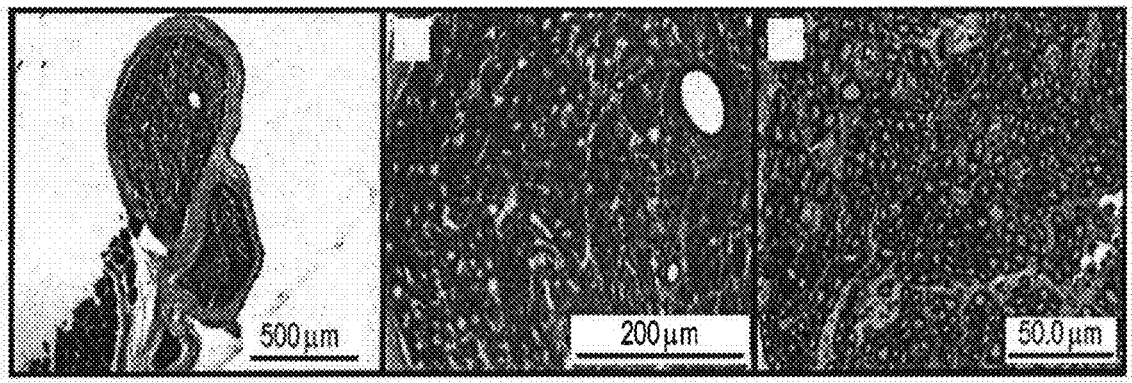

Histological examination of the Toluidine blue stained photomicrographs of semi-thin transverse sections of the sciatic nerves sampled from animals in the SHAM group at Week 4 (FIGS. 4A, 4B and 4C) and Week 6 (FIGS. 5A, 5B and 5C) following surgery revealed a regular sciatic nerve appearance at different magnifications. Tissue samples for SHAM animals showed the regular distribution of small and large diameter nerve fibers and normal proportion of myelin sheath thickness, fiber diameter, and intraneural blood vessels. Wallerian degeneration and unmyelinated fibers were evident in the tissue sections of the sciatic nerve 10 mm distal to the lesion site of CRUSH groups at Week 4 (FIGS. 4D, 4E and 4F) after crush nerve injury. The CRUSH sciatic nerves animals showed the presence of smaller minifascicles nerve fibers with less myelin and macro phages filled with degraded myelin following crush injury (FIGS. 4D, 4E and 4F). At week 6 following crush injury, the sciatic nerves from CRUSH animals (FIGS. 5D, 5E and 5F) displayed regenerative recovery but still showed the presence of smaller mini-fascicles nerve fibers with thin myelin sheaths and more myelin configurations and debris.

Figures 4G, 4H, 4I:
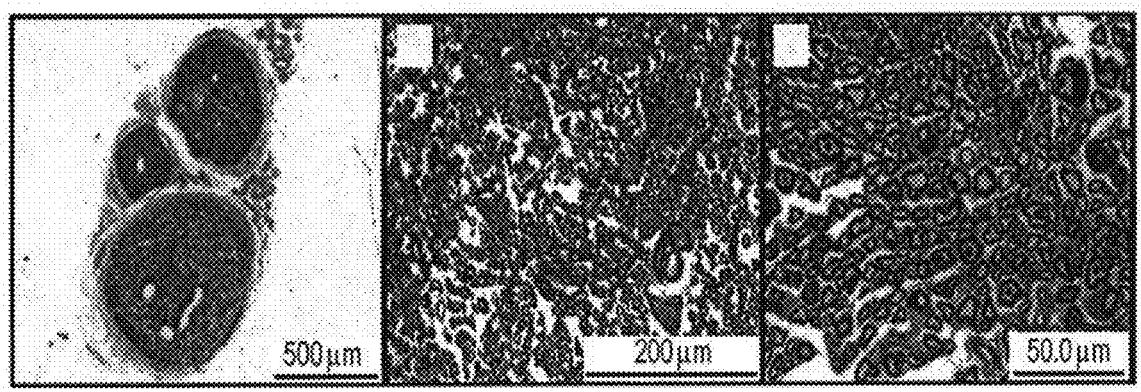
Figures 4J, 4K, 4L:
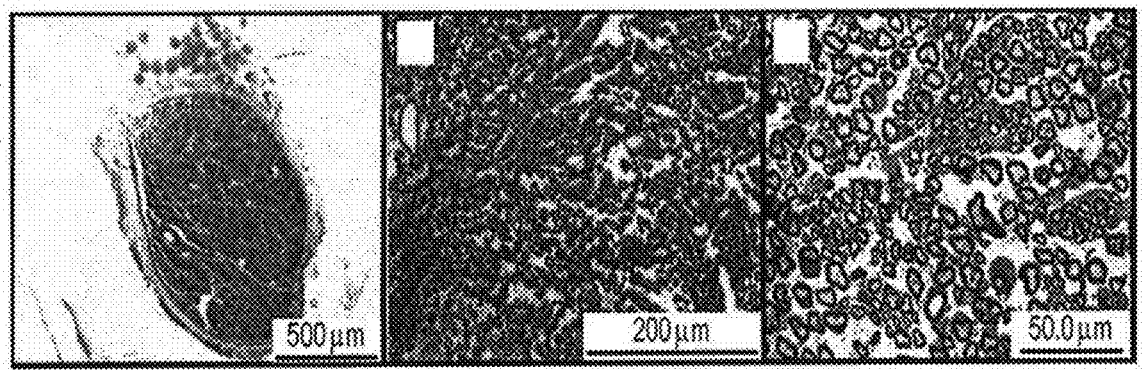
Figures 5J, 5K, 5L:
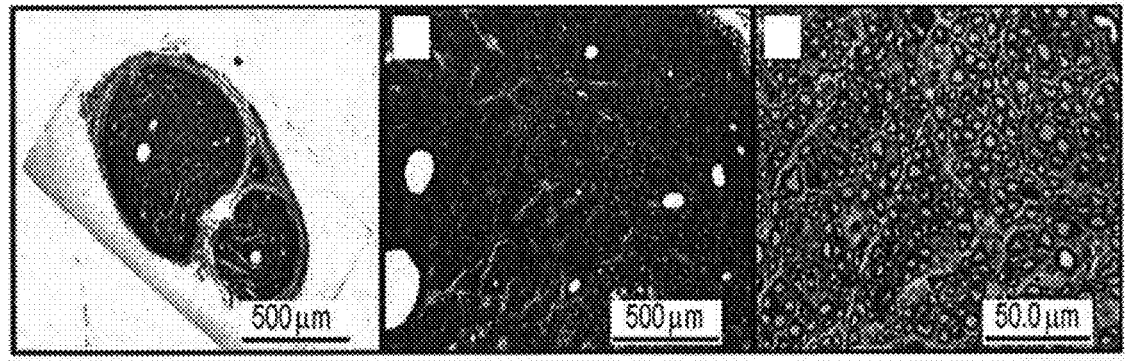
Figures 6A, 6B:
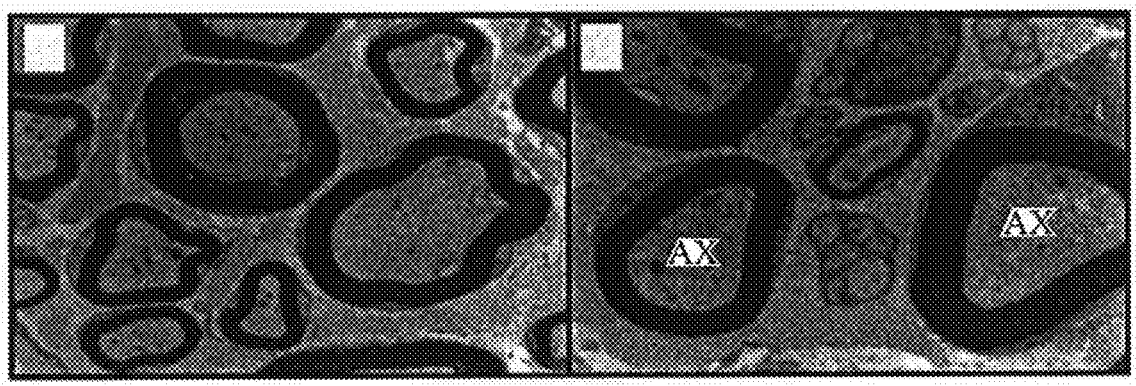
FIGS. 6A-6H show electron micrographs of sciatic nerve from the SHAM (FIG. 6A and FIG. 6B), CRUSH (FIG. 6C and FIG. 6D), CRUSH+SPF(I.P.) (FIG. 6E and FIG. 6F) and CRUSH+SPF(S.C.) (FIG. 6G and FIG. 6H) groups at Week 4 post-injury (Panel I; 5000× and Panel II; 1 0000×).
Figures 6C, 6D:
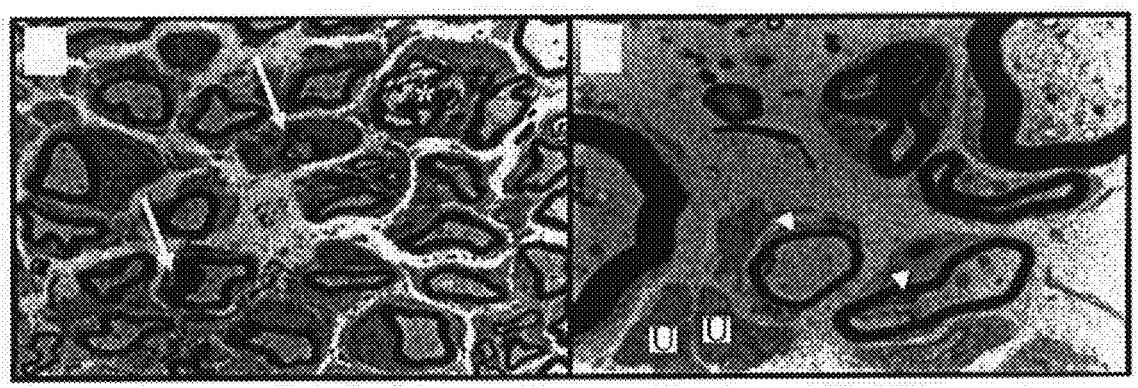
Figure 6E:
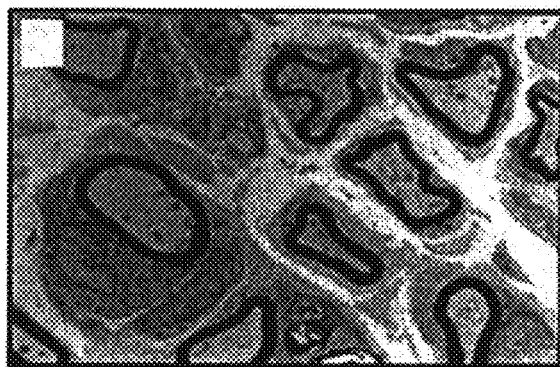
Figure 6F:
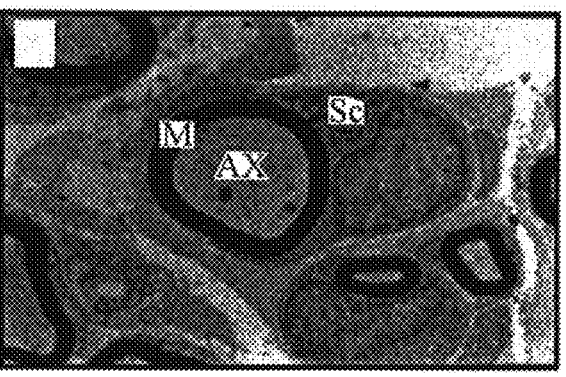
Figure 6G:
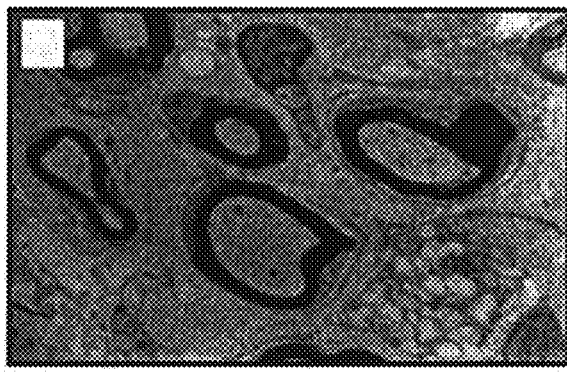
Figure 6H:
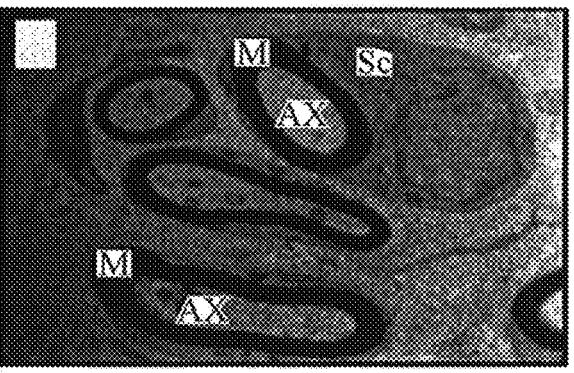

In contrast, at Week 4 following injury, sciatic nerve sections of CRUSH+O.5×SPF (IoP.) (FIGS. 4G, 4H and 4I) and CRUSH+1λSPF (S.C.) (FIGS. 4J, 4K and 4L) groups showed remarkable nerve regeneration with large-size nerve fibers surrounded with noticeable increase in myelin layers compared with those from the CRUSH (FIGS. 4D, 4E and 4F). The myelin debris and macrophages in the SPF-treated groups were much less compared to CRUSH nerves. Likewise, at Week 4, sciatic nerve sections of CRUSH+O.5×SPF (IoP.) (FIGS. 5G, 5H and 5I) and CRUSH+1×SPF (S.C.) (FIGS. 5J, 5K and 5L) groups showed remarkable nerve regeneration with less myclin debris compared to those from the CRUSH (FIGS. 5D, 5E and 5F) group. Further, the SPF-treated nerves showed more compactly arranged, regular shaped and more myelin surrounding the axons compared to CRUSH group.

Figure 7A:
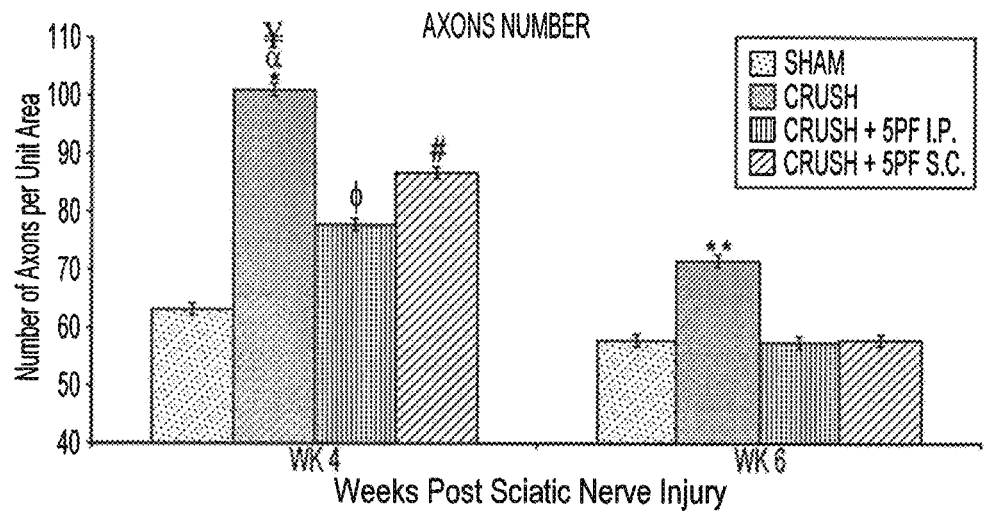
FIG. 7A is a graph depicting number of axons/field (at 1000× magnification) in cross-section of sciatic nerve distal to the injury site.
Figure 7B:
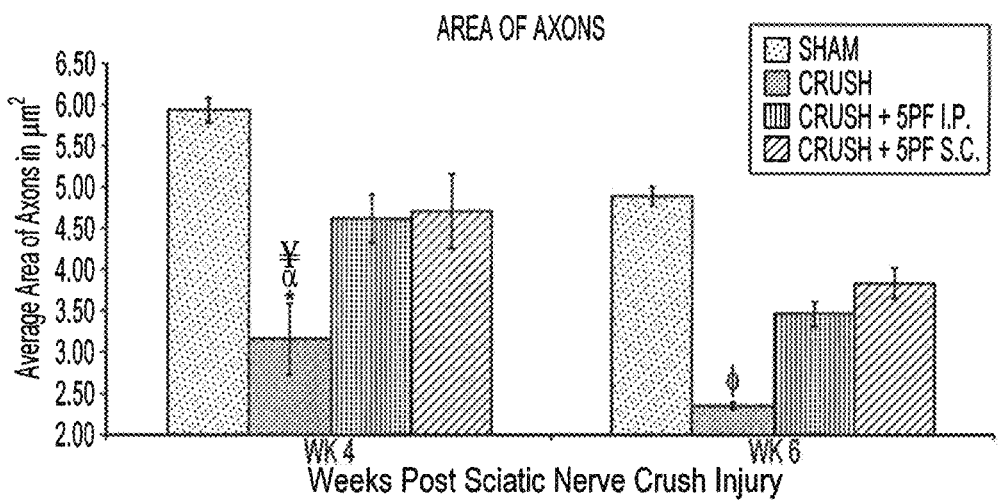
FIG. 7B is a graph depicting the mean cross-sectional areas of myelinated axon obtained from 10 different and randomly selected samples from each animal (3 animals/group).
Figure 7C:
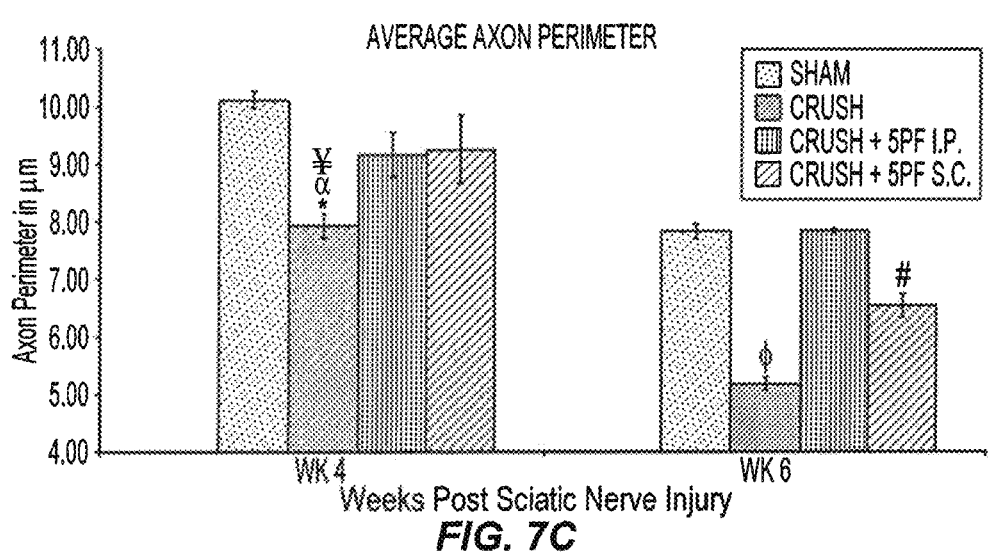
FIG. 7C is a graph depicting the mean axonal perimeters of myelinated axon obtained from 10 different and randomly selected samples from each animal (3 animals/group).

Examination of electron micrographs of sciatic nerve revealed vastly irregular shaped and highly condensed abnormal myelin sheaths, disintegrated axonal fibers and remnants of myelin scattered in between the axons in CRUSH group at Week 4 (FIGS. 7C and 7D) following injury compared to SHAM specimens (FIGS. 7A and 7B). Also, a sizeable number of unmyelinated or slightly myelinated axons were found in CRUSH group. At Week 5 (FIGS. 7C and 7D), the majority of the axons and nerve fibers were still small in size and thinly myelinated with a noticeable amount of extracellular cells and collagen fibers along with disintegrated and remnants of myelin scattered in between the axons in CRUSH nerves.

SPF-treated crushed sciatic (FIGS. 7E, 7F, 7G and 7H) nerves showed normal, healthy appearing myelin sheaths, with normal thickness and normal axons at Week 4. Also, the Schwann cells were healthy and appeared normal in SPF-treated animals. Likewise, the SPF-treated crushed sciatic nerves at Week 5 following nerve injury (FIGS. 7E, 7F, 7G and 7H) showed normal, healthy appearing myelin sheaths, with normal thickness and normal apparent axons.

Figure 8A:
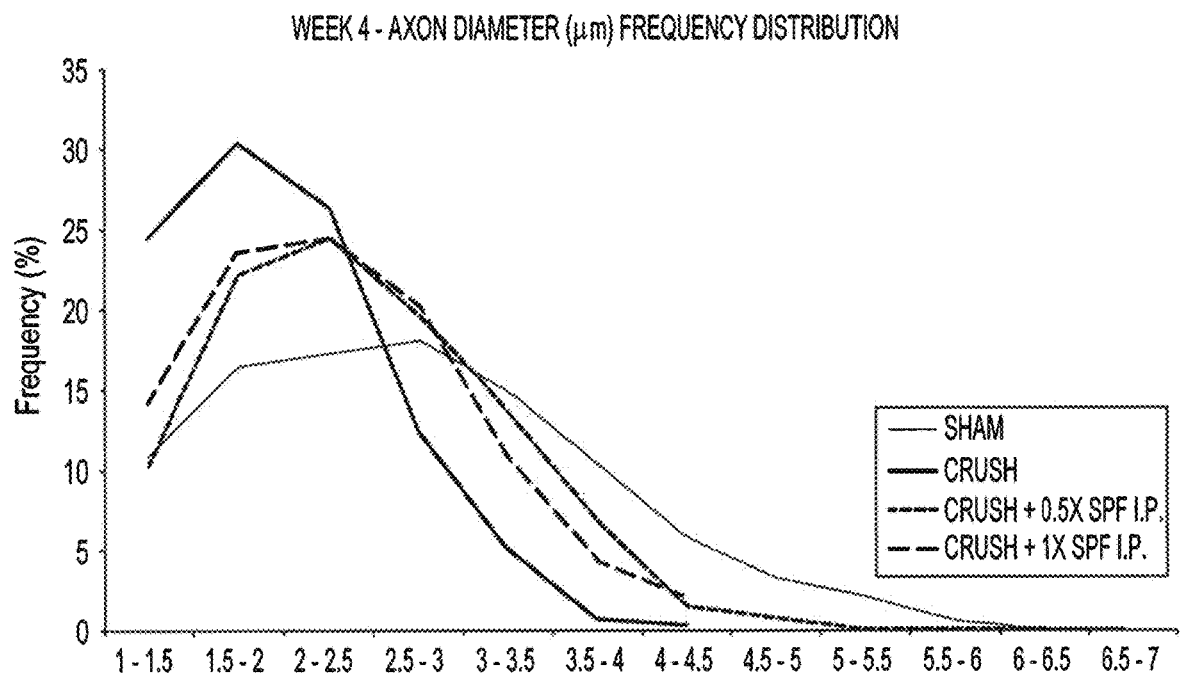
FIG. 8A is a graph depicting the percentage frequency of the myelinated axon diameter at week 4.
Figure 8B:
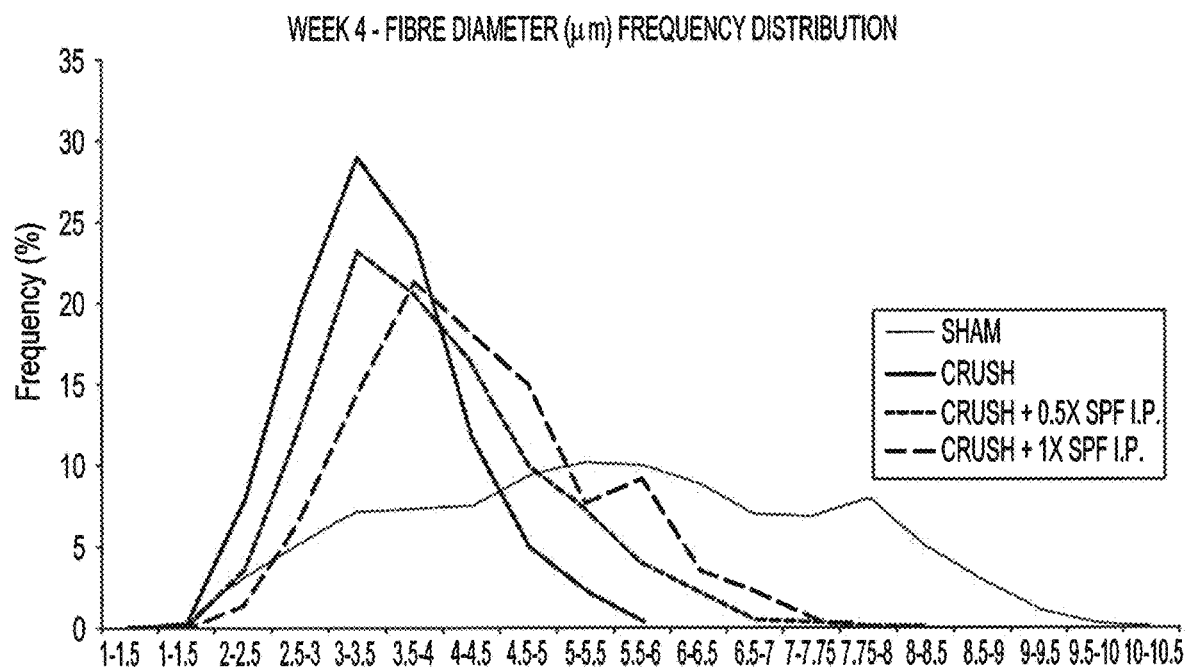
FIG. 8B is a graph depicting the percentage frequency of the nerve fiber diameter at week 4.
Figure 8C:
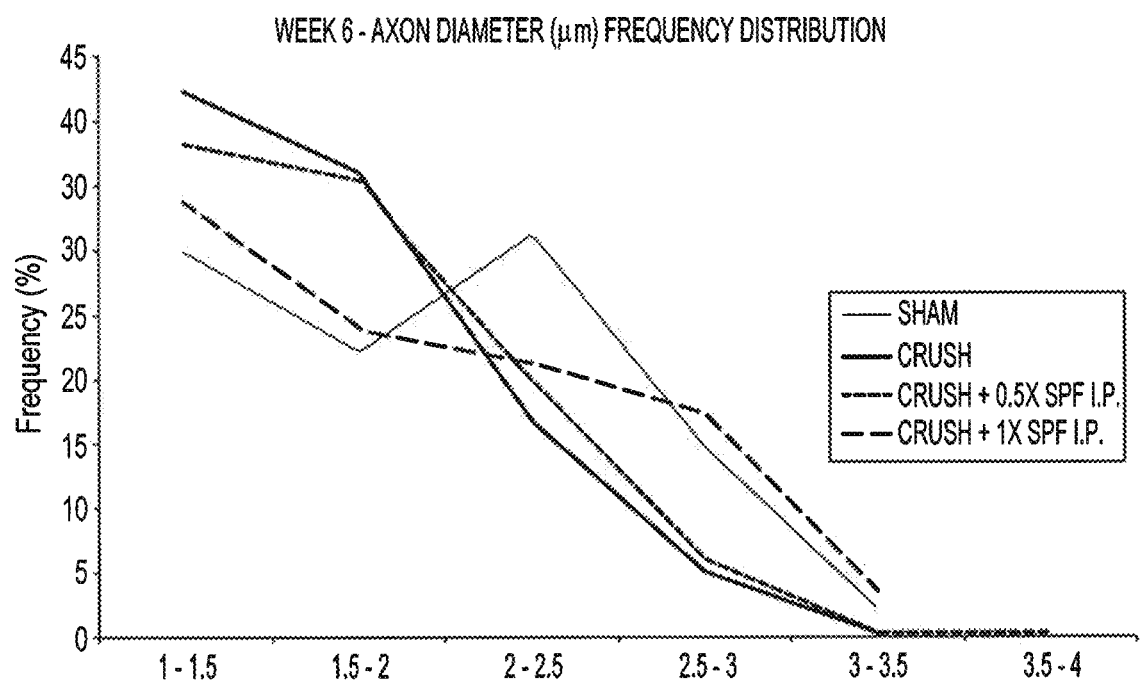
FIG. 8C is a graph depicting the percentage frequency of the myelinated axon diameter at week 6.
Figure 8D:
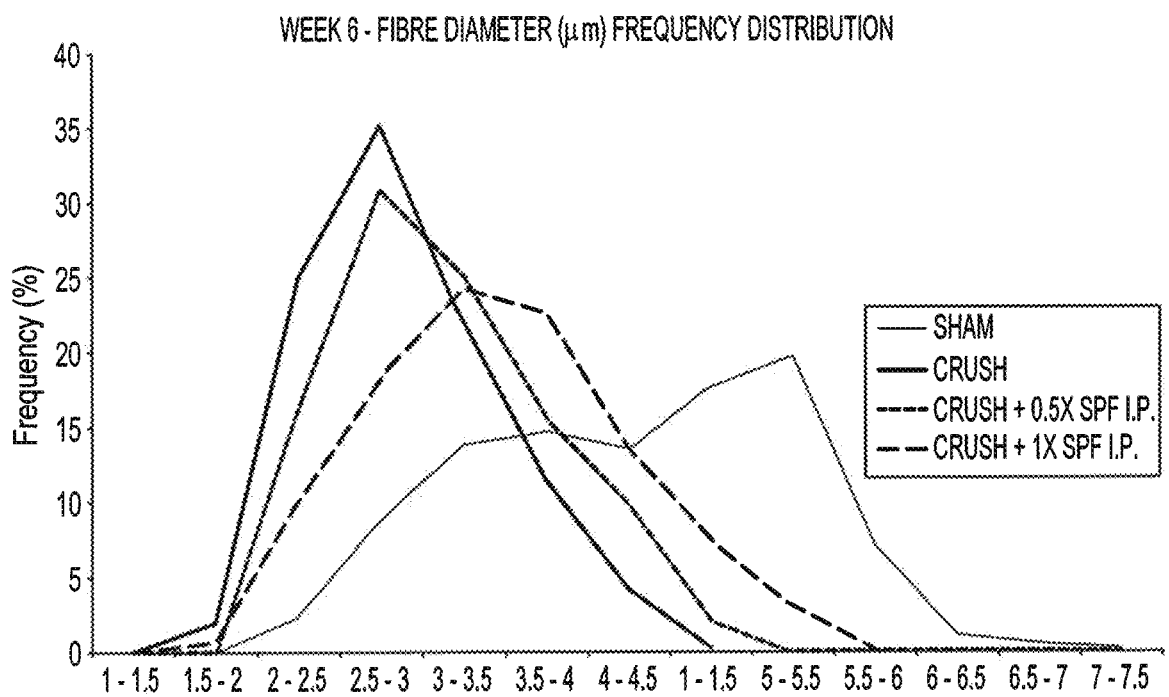
FIG. 8D is a graph depicting the percentage frequency of the nerve fiber diameter at week 6.

Morphometric analysis data of sciatic nerves after 4 and 6 weeks post-surgery are presented in FIGS. 8A-8C. FIG. 8A shows the mean total number of the myelinated axon that was calculated for each experimental group at Weeks 4 and 6 following sciatic nerve injuries using square counting frame. At Week 4 after sciatic injury, the CRUSH+0.5×SPF (I.P.)-treated ($p<0.02$), CRUSH+1×SPF (S.C.)-treated ($p<0.001$) and CRUSH ($p<0.0001$) groups showed a significant increase in the mean total myelinated axons numbers compared with SHAM groups. I.P. and S.C. SPF treatments significantly ($p<0.001$ and $p<0.01$, respectively) decreased the number of axons unit area following nerve crush injury at Week 4 compared to CRUSH group. Further, the number of axons per unit area of the I.P. and S.C. SPF-treated groups returned to SHAM level by Week 6. However, in the CRUSH animals, the number of axons per unit area remained significantly ($p<0.005$) increased, but the axons were immature and were thinly myelinated compared to SHAM and I.P. and S.C. SPF-treated groups, which showed thicker myelination at Week 6 (FIG. 8A). The result of the mean cross-sectional areas of myelinated axons obtained from different and randomly selected samples from each animal are depicted in FIG. 8B. The averaged areas of myelinated axons measured in square micrometers ($\mu m^2$) were calculated for each experimental group at Week 4 and 6 following sciatic nerve injuries. The CRUSH animals showed significant decrease in the average areas of myelinated axons compared with SHAM ($p<0.002$), CRUSH+ 0.5×SPF (I.P.) ($p<0.01$) and CRUSH vs CRUSH+1×SPF (S.C.) ($p<0.05$) at Week 4. At Week 6 after the nerve injury, the I.P. and S.C. SPF-treated groups displayed significant ($p<0.01$) increase in the mean areas of the myelinated axons compared to CRUSH group. Moreover, the I.P. and S.C. SPF-treated groups at Week 6 showed no difference in mean areas compared to SHAM animals (FIG. 8B).

The averaged perimeters of myelinated axons measured in square micrometers ($m^2$) were calculated for each experimental group at Weeks 4 and 6 following sciatic nerve injuries (FIG. 8C). The CRUSH animals showed significant decrease in the average perimeters of myelinated axons compared with SHAM ($p<0.002$), CRUSH+0.5×SPF (I.P.) ($p<0.02$) vs CRUSH+1×SPF (S.C.) ($p<0.03$) at Week 4. At Week 6 after nerve injury, the I.P. and S.C. SPF-treated groups displayed significant ($p<0.000$) increase in the mean areas of the myelinated axons compared to CRUSH group. However, average perimeters of myelinated axons in the CRUSH+1×SPF (S.C.) group were still significantly ($p<0.003$) lower than CRUSH+0.5×SPF (I.P.) group.

Myelinated axon diameters (d), myelinated nerve fiber diameter (I)) (FIG. 8E), and myelin thickness were stereologically estimated from 10 different random samples. The samples were selected from each animal for each experimental group at Week 4 and 6 following sciatic nerve injury using square counting frame. The CRUSH animals displayed a significant ($p<0.002$-$p<0.03$) decrease in axon diameter at all the time points assessed following nerve injury compared with SHAM and CRUSH SPF-treated groups. However, I.P. and S.C. SPF-treated groups showed no significant change in axon diameter in comparison with SHAM animals at Week 4 and Week 6 post-nerve injury indicating the growing process of the nerves. The nerve fiber diameter sizes (D) in the CRUSH and I.P. and S.C. SPF-treated groups at Week 4 and 6 displayed significant ($p<0.000$) decrease compared to SHAM group. However, the nerve fiber diameter sizes in the CRUSH animals were significantly less compared to CRUSH+0.5×SPF (I.P.) at Week 4 ($p<0.001$) and Week 6 ($p<0.04$) following nerve injury. Likewise, the calculated myelin thickness for the CRUSH and CRUSH SPF-treated groups show a significant ($p<0.001$) decrease in myelin thickness compared to SHAM animals at Week 4 and Week 6 following sciatic nerve injury. However, the myelin thickness in CRUSH SPF-treated animals increased significantly ($p<0.003$-$P<0.05$) at Week 4 and increased more at Week 6 compared with CRUSH group, indicating the recovery process of the CRUSH SPF-treated groups. In support of the stereological analysis, the MBP density analysis of the distal nerve samples significantly increased basic myelin content in the I.P. and S.C. SPF-treated groups at Week 4 ($p<0.000$) and Week 6 ($p<0.01$) post sciatic nerve injury. However, the basic myelin protein content increase 22 in the I.P. SPF-treated group did not reach the normal levels at Week 6 post-injury in the SHAM.

For further ratification of the morphometric data, the diameters of myelinated nerve axons and fibers were measured from Week 4 (FIGS. 8A and 8B) and Week 6 (FIGS. 8C and 8D) samples and the diameter distribution plotted. The CRUSH group displayed a remarkable shift in the distribution of the axon and nerve fiber diameter sizes to the left toward the low range values compared to SHAM animals at Week 4 and week 6. Although the treated groups showed an improvement distribution pattern of the axon and nerve fiber diameters the CRUSH SPF (I.P.) treated group displayed more normalization of axon and nerve fiber diameter distribution compared to the CRUSH SPF (SC)-treated group at Week 4 and Week 6 (FIGS. 8A-8D).

Figures 9E, 9F, 9G, 9H:
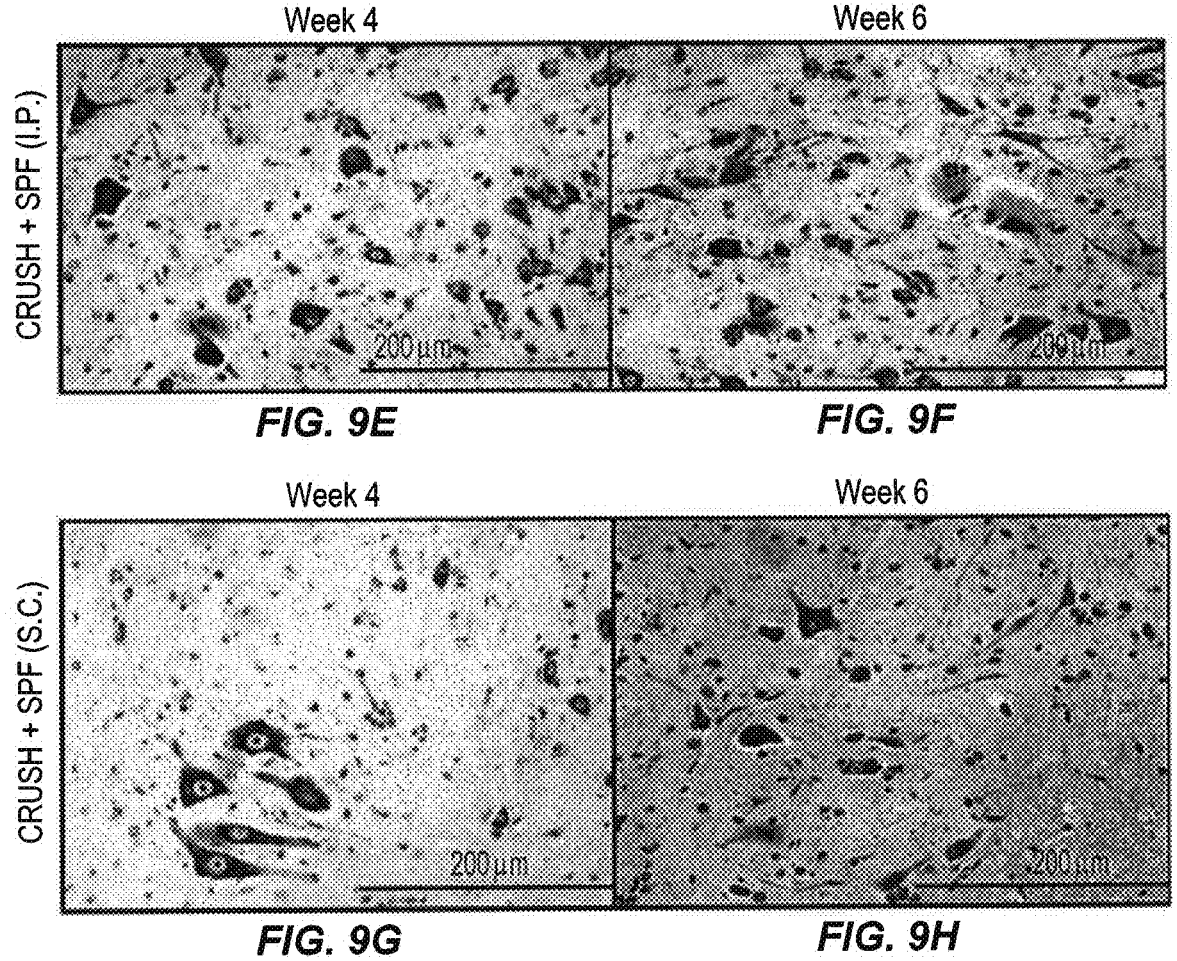
Figures 10A, 10B, 10C, 10D:
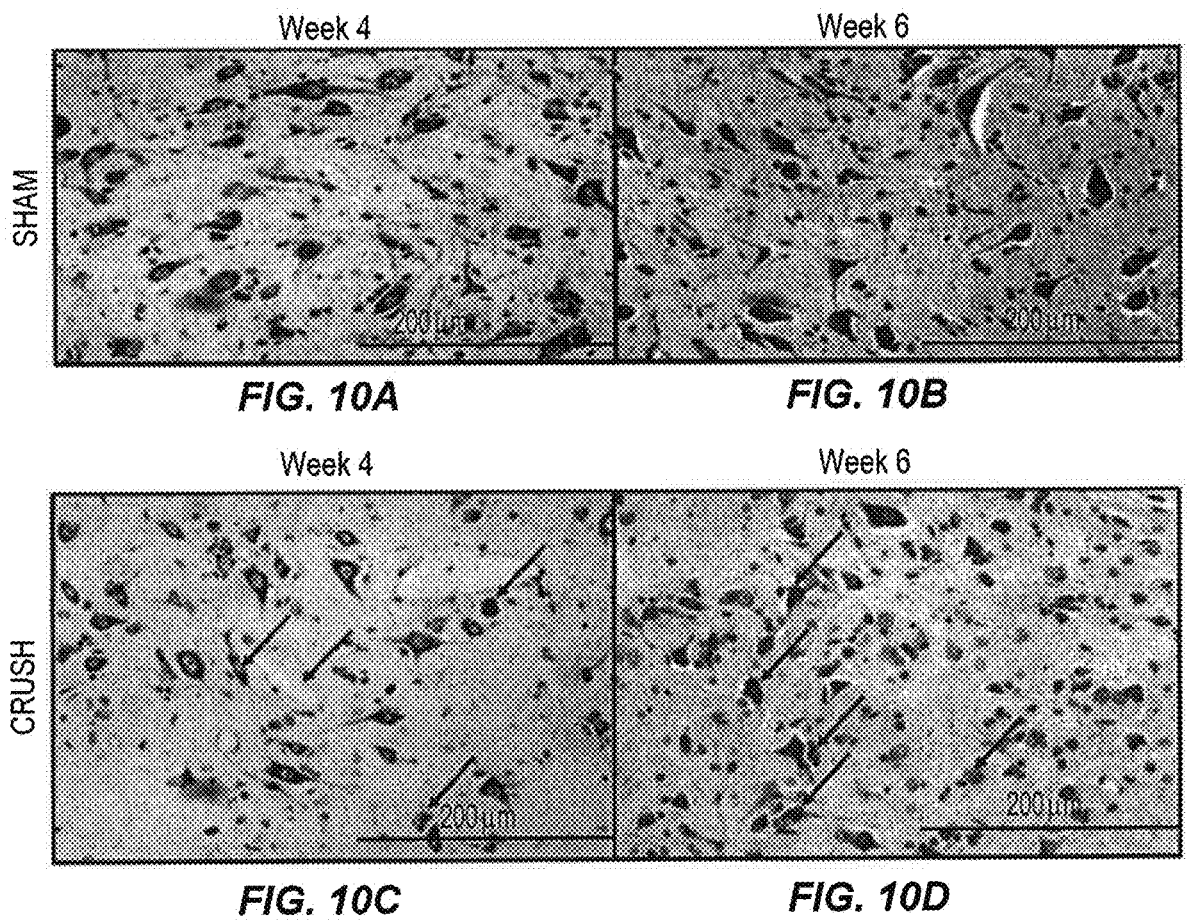

Histological examination of the Cresyl violet stained sections of the lumbar spinal cord ventral and dorsal grey horns at Week 4 and 6 after nerve injury are demonstrated in FIGS. 9A-9H and 11A-11H, respectively. The CRUSH animals revealed fewer healthy ventral and dorsal horn neurons and a large number of degenerating neurons at Week 4 (9C and 10C) and Week 6 (FIGS. 9D and 11D) compared to SHAM (FIGS. 9A and 9B) group. The number of neurons in the ventral horn is remarkably more in CRUSH SPF (loP.) group compared to CRUSH group at Week 4 (FIGS. 9E and 9E) and Week 6 (10F and 11F). Likewise, the number of neurons in the dorsal horns of the CRUSH SPF (S.C.)-treated group is noticeably more compared to CRUSH group at Week 4 (9G and 9G) and Week 6 (9H and 10H) after nerve crush injury.

Figures 12A, 12B, 12C, 12D:
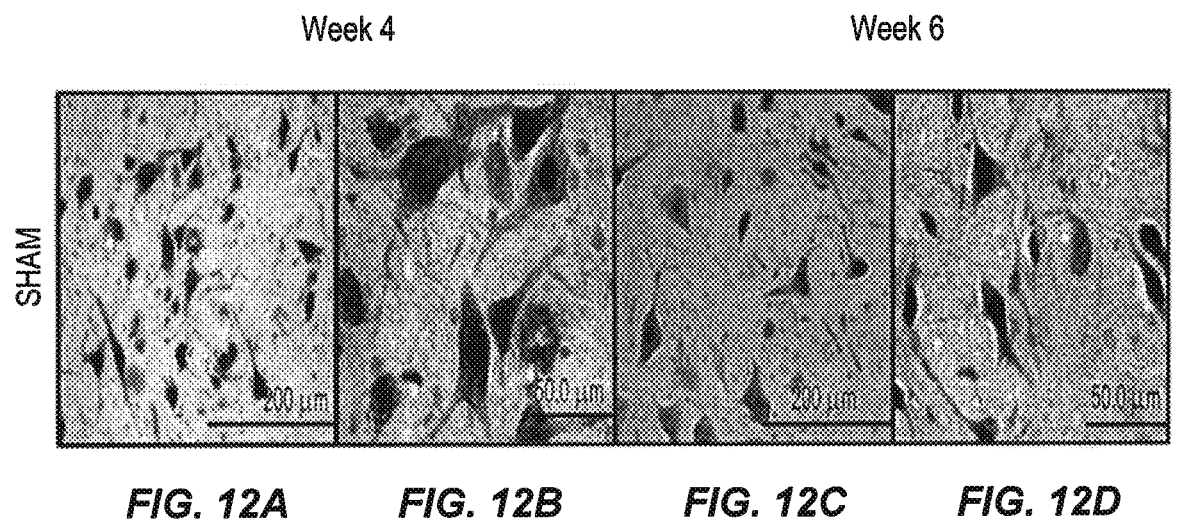
FIGS. 12A-12P depict photomicrographs of the lumbar spinal cord ventral grey horn immunostained for NeuN at Week 4 and Week 6 post-injury for all groups (SHAM group-FIGS. 12A-12D; CRUSH group-FIGS. 12E-12H; CRUSH SPF (loP.) group-FIGS. 12I-12L; CRUSH SPF (S.C.) group-FIGS. 12M-12P).
Figures 12E, 12F, 12G, 12H:
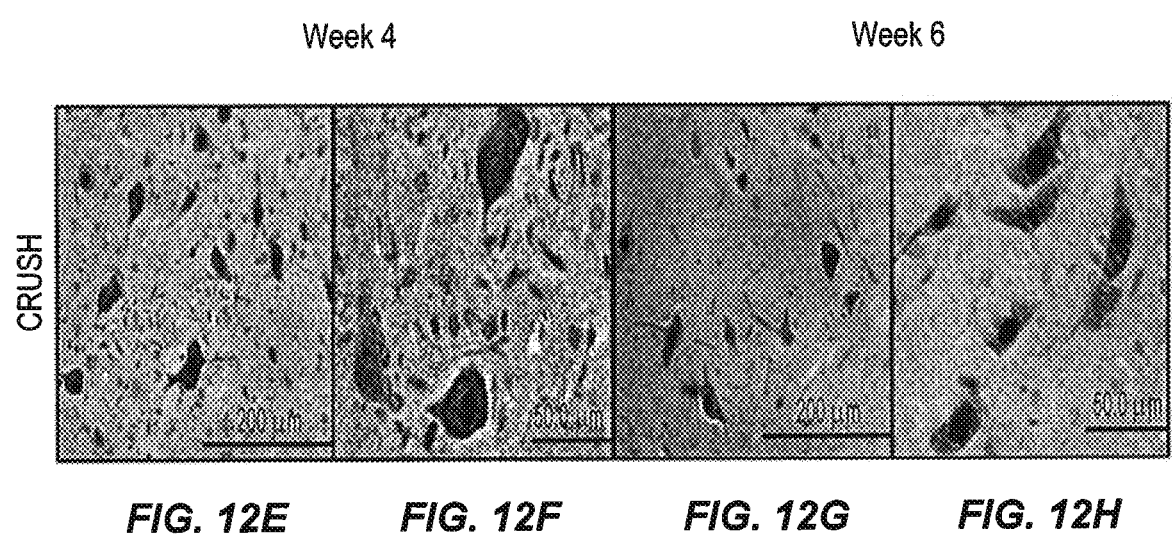
Figures 12I, 12J, 12K, 12L:
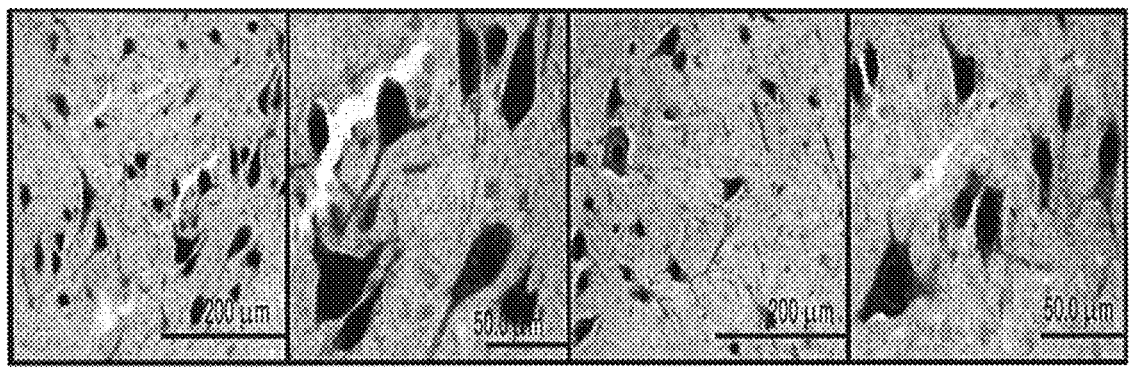
Figures 12M, 12N, 12O, 12P:
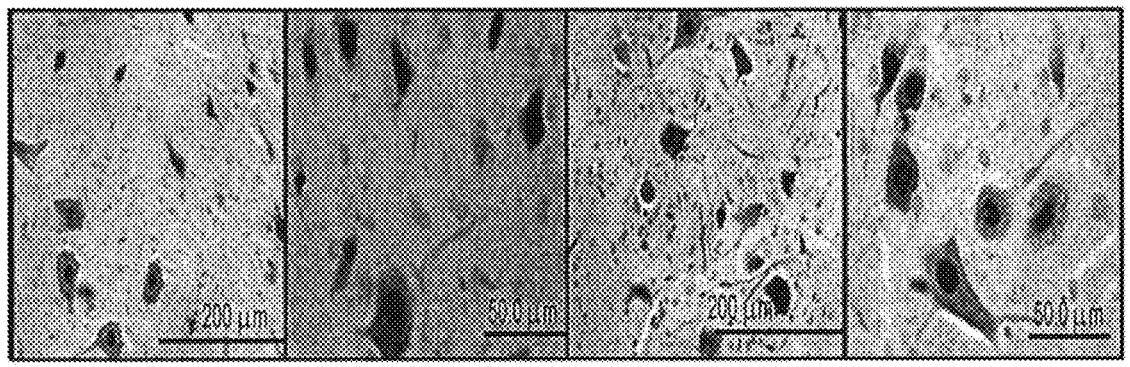

Immunostaining for neurons with neuronal marker NeuN showed fewer neurons in the CRUSH group at Week 4 (FIG. 11C) and Week 6 (FIG. 11D) compared to the SHAM group (FIGS. 11A and 11B, respectively). I.P. and S.C. SPF-treated groups showed more neurons compared to the CRUSH group at Week 4 (FIGS. 11E and 11G) and Week 6 (FIGS. 11 F and 11H). High magnification (40× and 100×) photomicrographs of the lumbar spinal cord ventral grey horn immunostained for NeuN at Week 4 and Week 6 post-injury for all groups are shown in FIGS. 12A-12P).

Figure 13A:
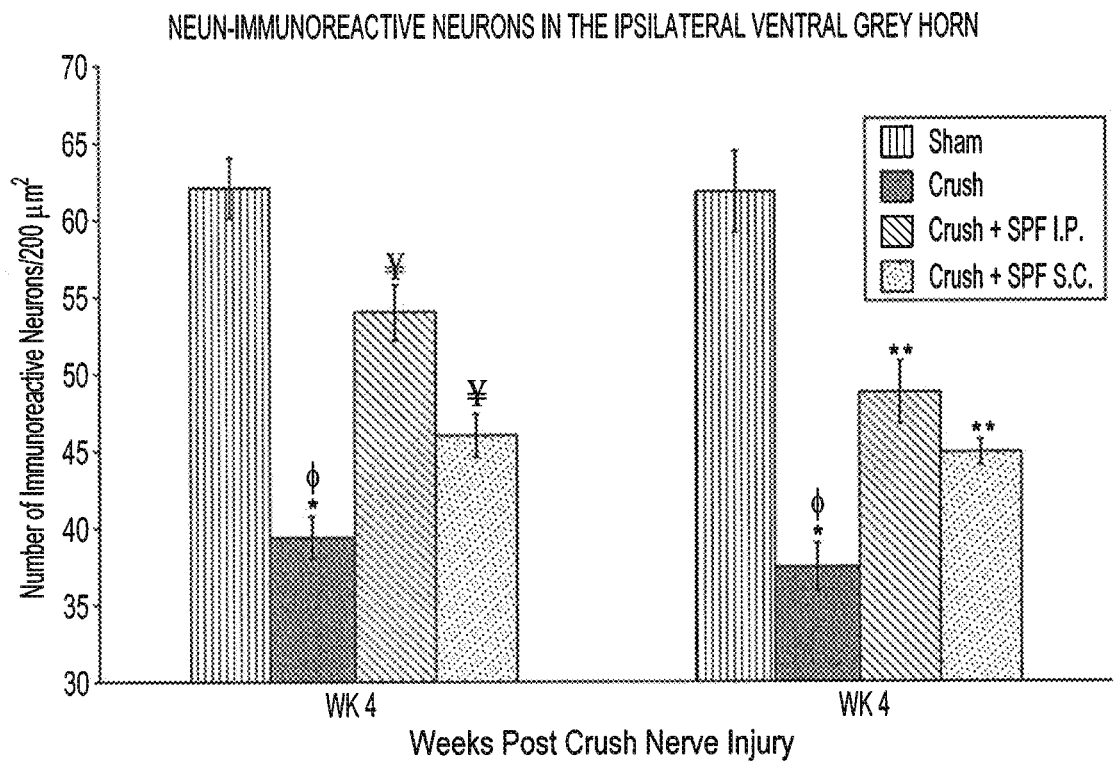
FIG. 13A is a graph showing the number of NeuN-immunoreactive neurons in the ipsilateral ventral grey horn at Week 4 and Week 6 post-injury.

The sciatic nerve crush injured animals displayed a notable decrease in the number of NeuN-immunostained neurons at Week 4 (FIGS. 12E and 12F) and Week 6 (FIGS. 12G and 12H) compared to SHAM group (FIGS. 12 A, 12B, 12C and 12D). The number of the NeuN-immunoreactive neurons is remarkably more in the CRUSH SPF (IoP.) and CRUSH SPF(S.C.)-treated groups at Week 4 (FIGS. 12I, 12J and FIGS. 12M and 12N, respectively) and Week 6 (FIGS. 12K and 12L and FIGS. 12O and 12P, respectively) compared to CRUSH group. Likewise, the number of the NeuN-immunoreactive neurons in the dorsal grey horn is remarkably more in the CRUSH SPF (IoP.) and CRUSH SPF (S.C.)-treated group at Week 4 and Week 6 compared to CRUSH group. Morphometric analysis of the ipsilateral ventral grey horn showed significant (p<0.000) decrease in the number of the NeuN-immunostained neurons in the CRUSH group compared to SHAM at Week 4 and Week 6 post-injury (FIG. 13A). Further, the number of NeuN positive neurons significantly (p<0.000 and p<O.OOS) increased in the CRUSH SPF (IoP.) and CRUSH SPF (S.C.)-treated groups at Week 4 and Week 6 post-injury.

Figure 13B:
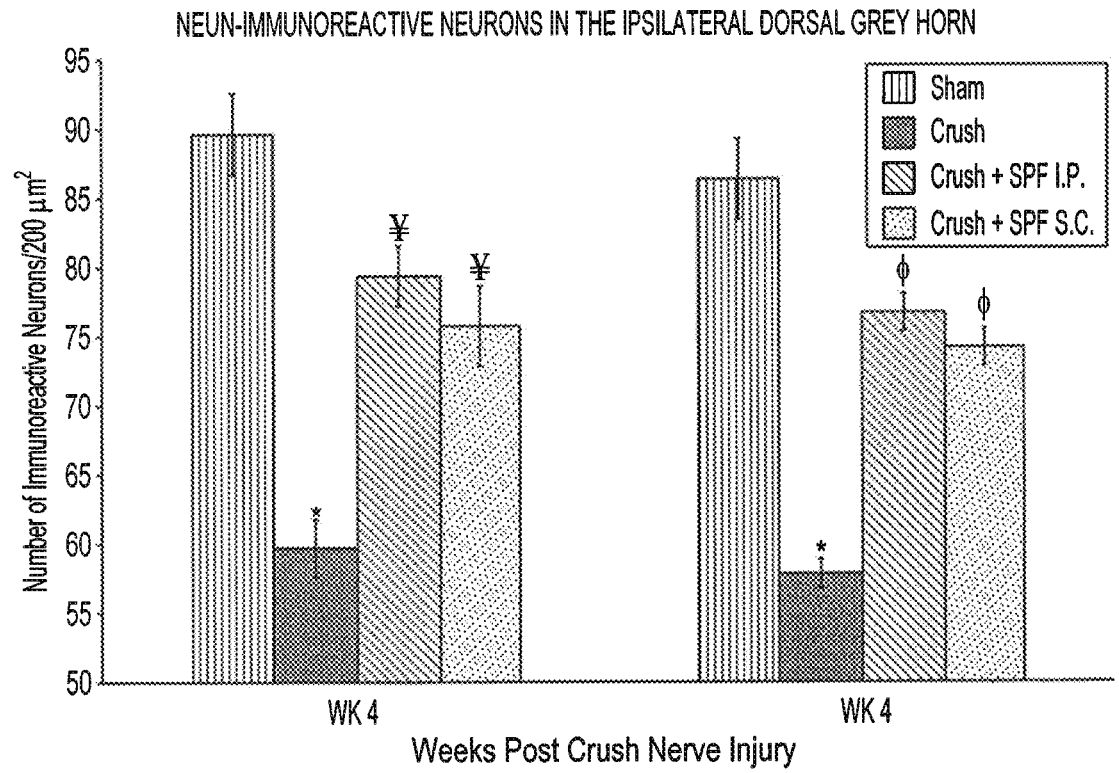
FIG. 13B is a graph showing the number of NeuN-immunoreactive neurons in the ipsilateral dorsal grey horn at week 4 and week 6 post-injury.
Figure 14:
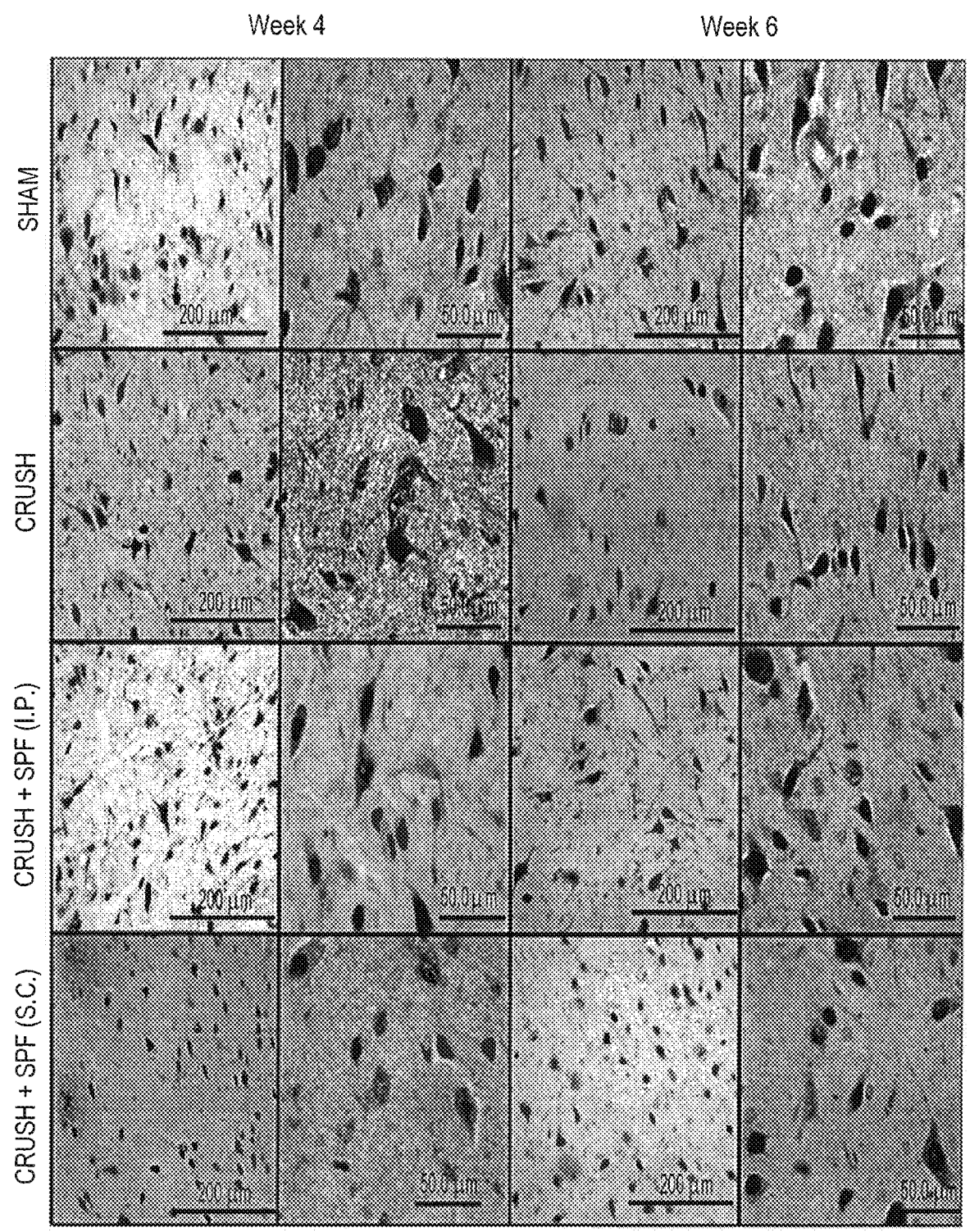
FIG. 14 shows representative photomicrographs of lumbar spinal cord dorsal grey horn from rats of experimental groups immunostained for NeuN at week 4 and week 6 post injury.

Likewise, analysis of the ipsilateral dorsal grey horn showed significant (p<0.000) decrease in the number of the NeuN-immunostained neurons in the CRUSH group compared to SHAM at Week 4 and Week 6 post-injury (FIG. 13B). High magnification (40× and 100×) photomicrographs of the lumbar spinal cord dorsal grey horn immunostained for NeuN at Week 4 and Week 6 post-injury are shown in FIG. 14. In contrast, the number of NeuN-immunostained neurons significantly (p<0.000) increased in the CRUSH SPF (I.P.) and CRUSH SPF (S.C.)-treated groups at Week 4 and Week 6 post-injury. However, the number of the NeuN-immunostained neurons in the treated groups still significantly lower at Week 4 (p<0.02) and Week 6 (p<0.004) compared to SHAM animals (FIGS. 15A-15H).

Figures 15A, 15B:
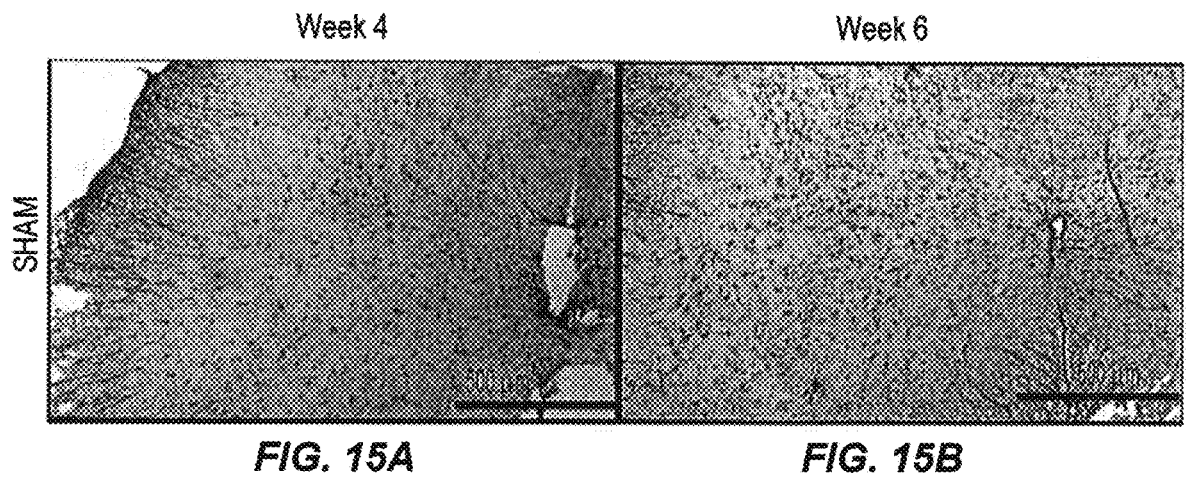
Figures 15C, 15D:
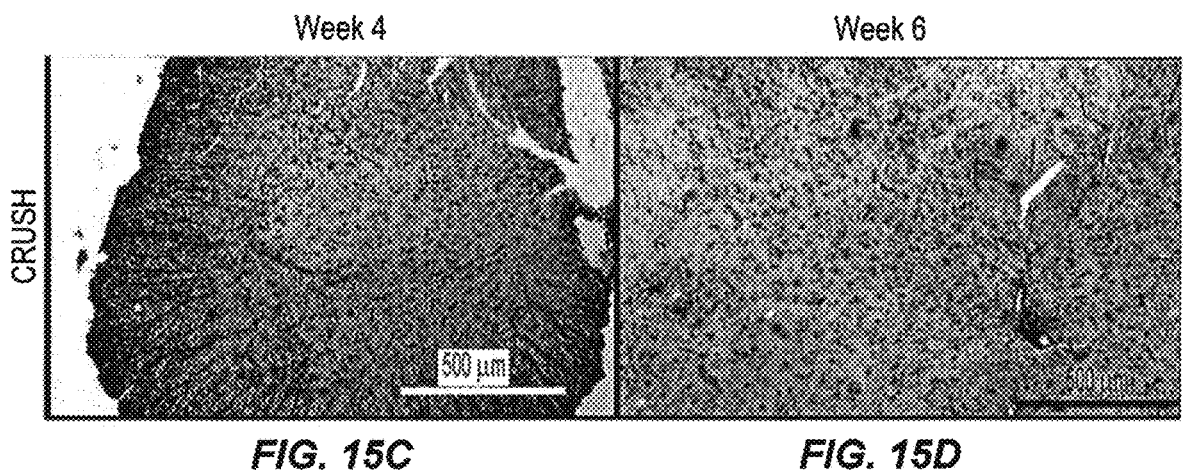
Figures 16A, 16B, 16C, 16D:
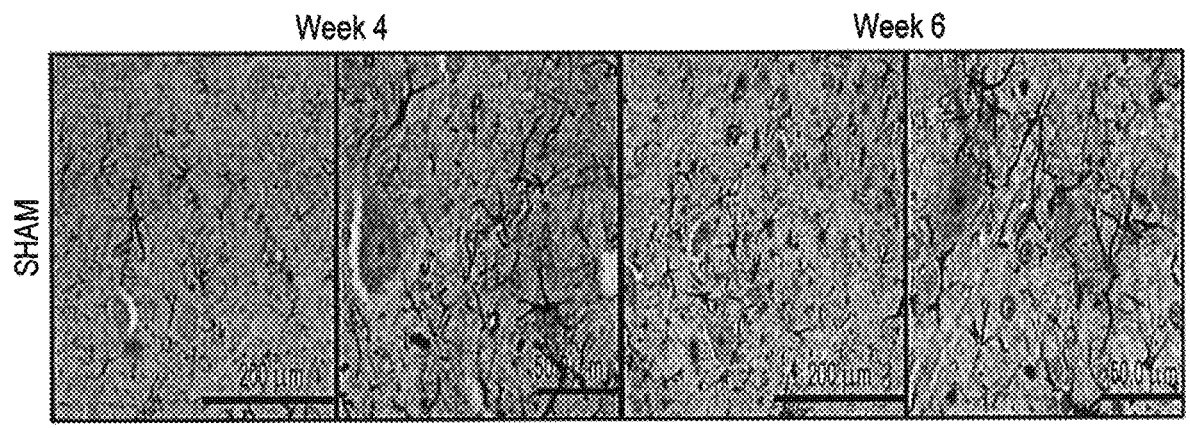
FIGS. 16A-16P show representative 40× and 100× photomicrographs of lumbar spinal cord ventral grey horn from rats of the experimental groups immunostained for GFAP at Week 4 and Week 6 post-injury.
Figures 16E, 16F, 16G, 16H:
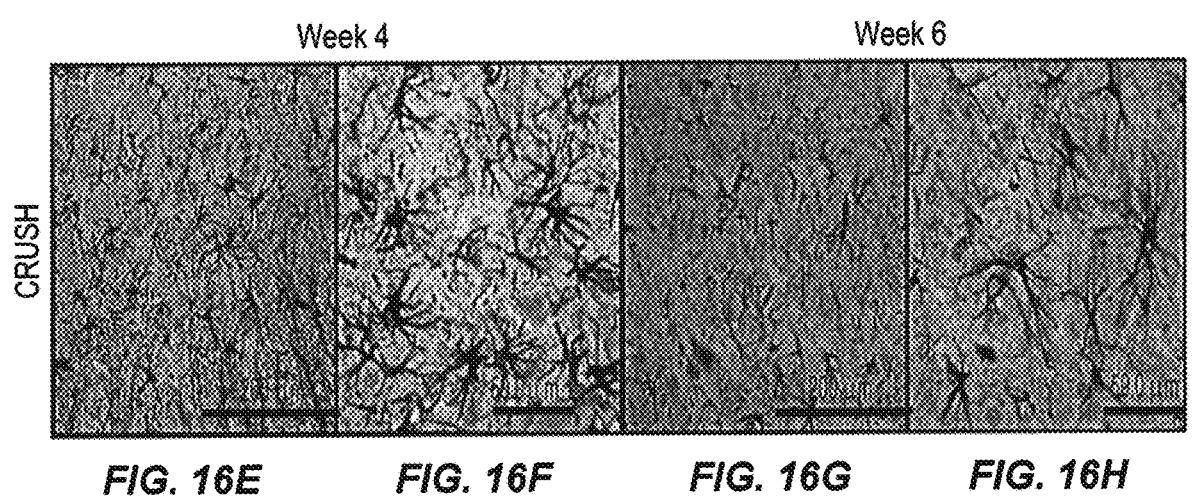
Figure 17A:
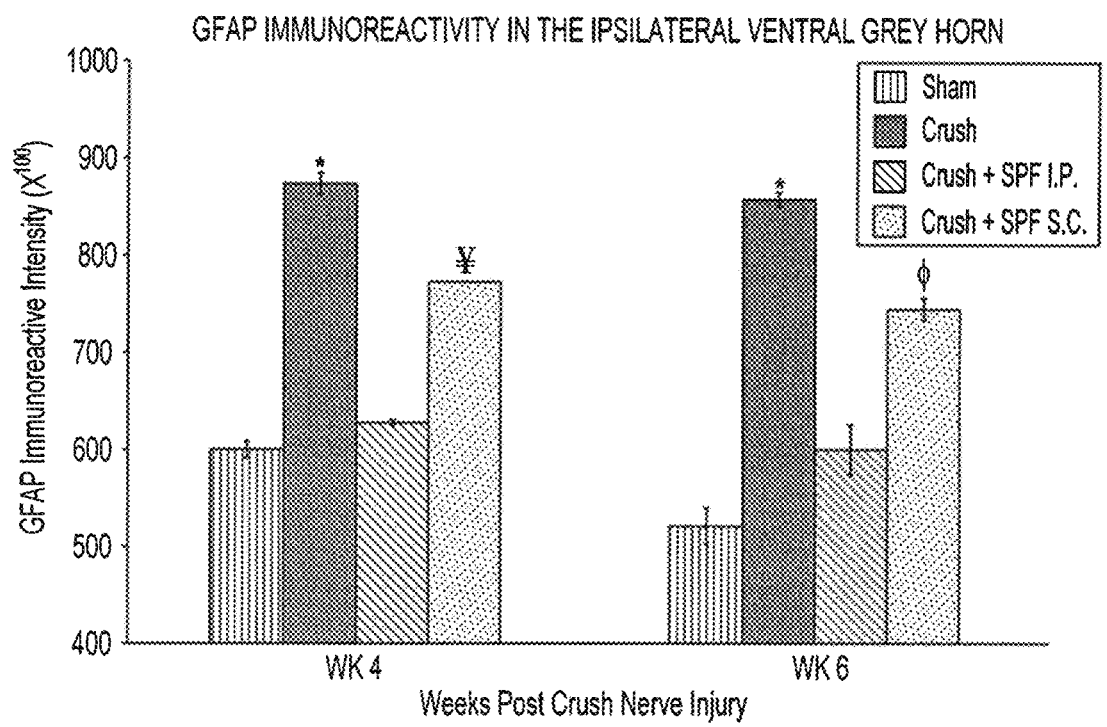
FIG. 17A is a bar graph showing the number of GFAP-immunoreactive astrocytes in the ipsilateral ventral greyhorn at week 4 and week 6 post-injury.
Figure 17B:
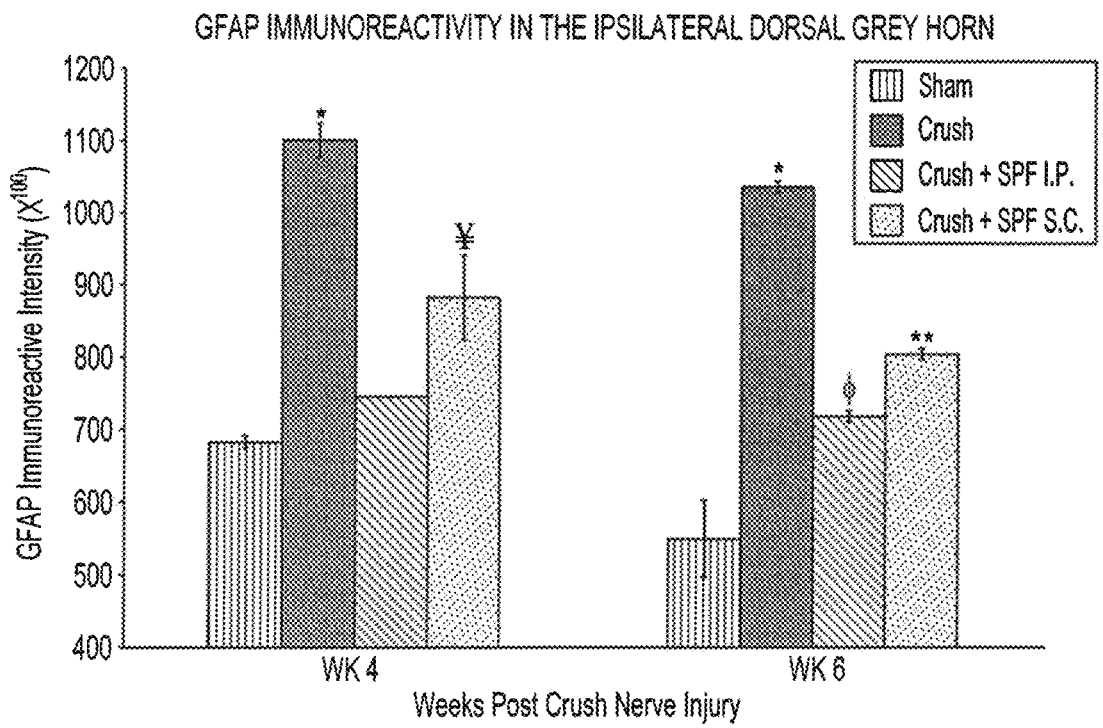
FIG. 17B is a bar graph showing the number of GFAPimmunoreactive astrocytes in the ipsilateral dorsal grey horn at week 4 and week 6 post-injury.
Figure 17C:
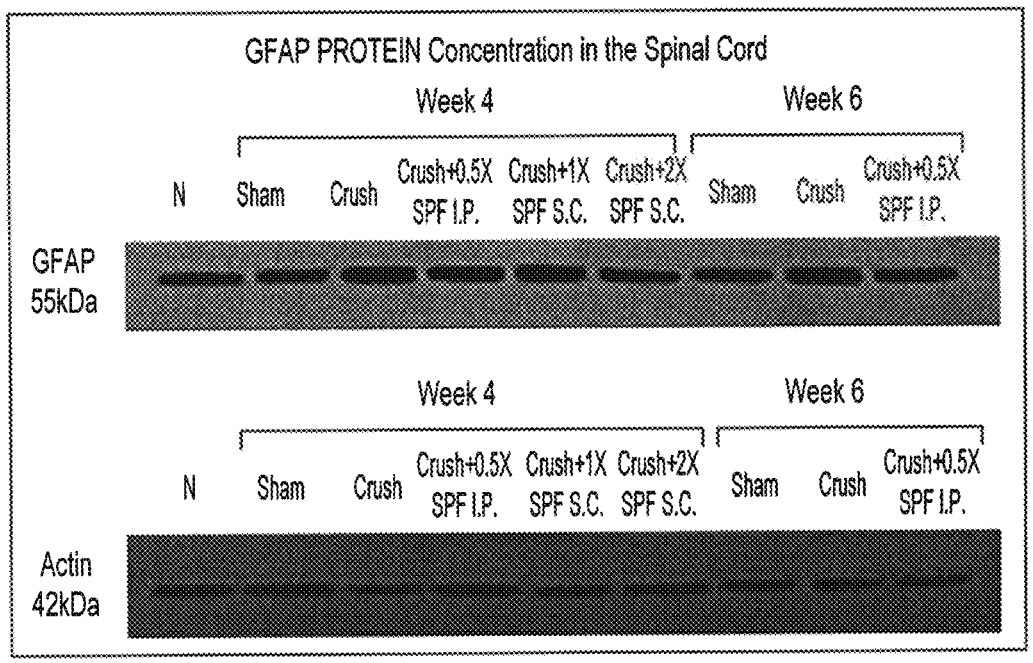
FIG. 17C shows Western blot analysis of glial fibrillary acidic protein (GFAP) in the lumbar spinal cords from all the experimental groups at Week 4 and Week 6 following nerve injury.
Figure 17D:
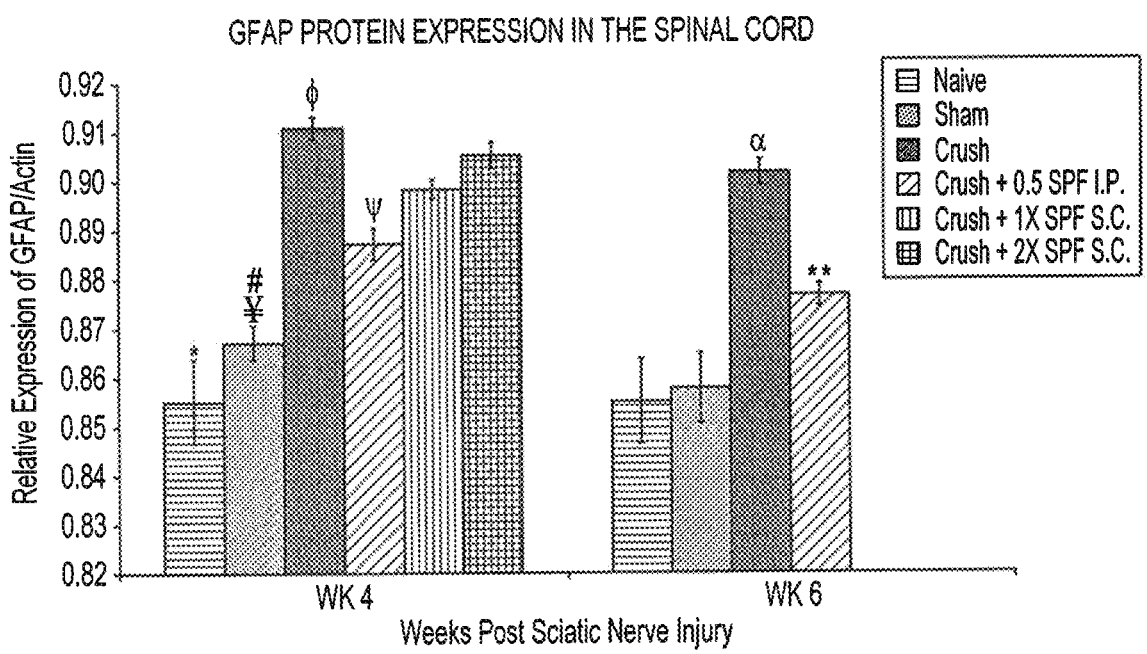
FIG. 17D is a bar graph showing the GFAP density in spinal cord samples (n=3 rats/group) normalized with densities of actin band (Molecular weight-42).
Figure 17E:
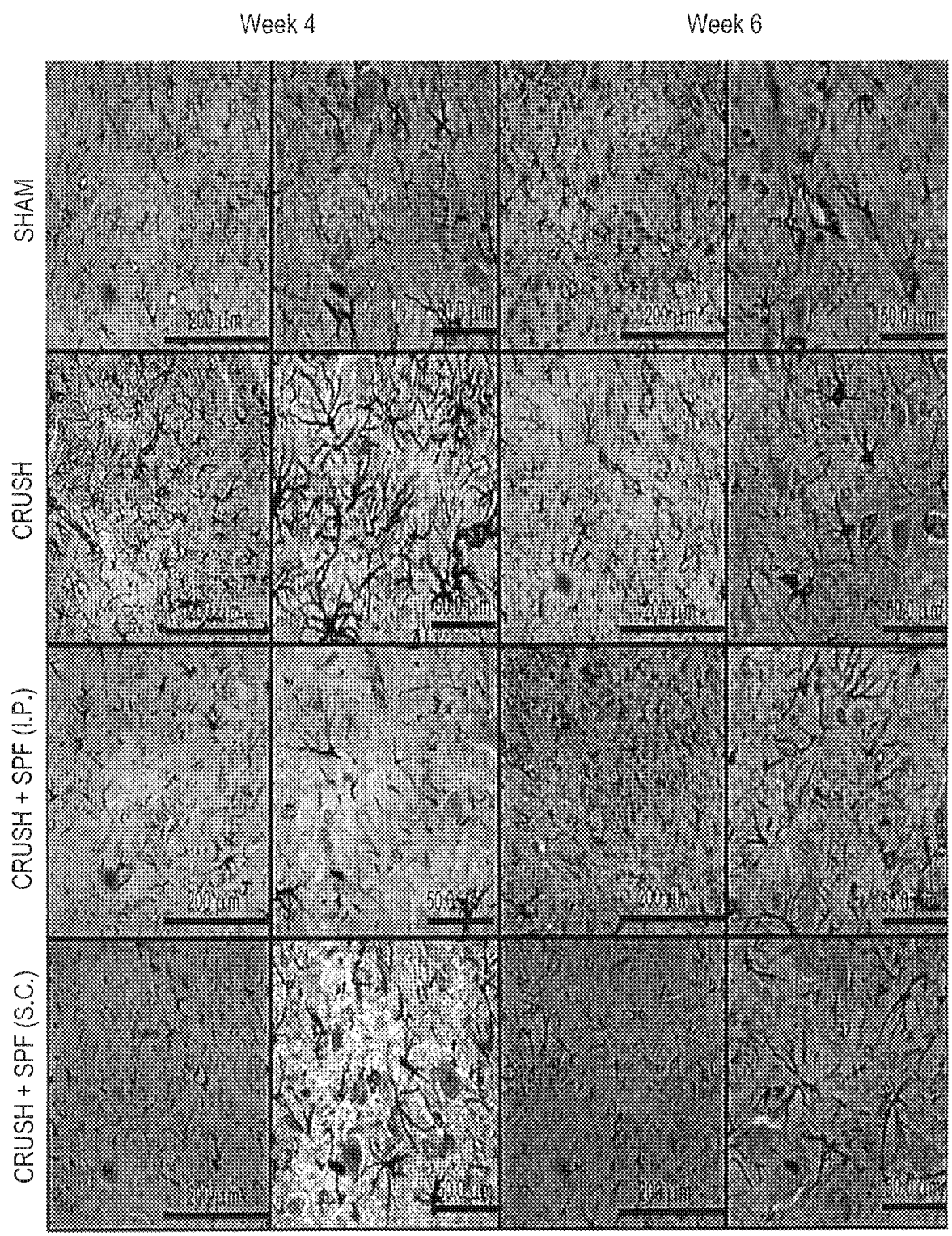
FIG. 17 E depicts show representative photomicrographs of spinal cord dorsal grey horn from rats of all groups immunostained for GFAP at Week 4 and Week 6 following nerve crush injury

Immunostaining for astrocytes with GFAP antibodies showed a remarkable increase in the GFAP-immunoreactive astrocytes in the CRUSH animals at Week 4 (FIG. 15C) and Week 6 (FIG. 15D) compared to the SHAM group (FIGS. 15A and 15B, respectively). IoP. and S.C. SPF treatments decreased the GFAP immunoreactivity compared to the CRUSH group at Week 4 (FIGS. 15E and 15G) and Week 6 (FIGS. 15F and 15H). High magnification (40× and 100×) photomicrographs of the lumbar spinal cord ventral grey horn immunostained for GFAP at Week 4 and Week 6 post-injury are shown in FIGS. 16A-16P. The number of GFAP-immunostained astrocytes in the ventral grey horn of the CRUSH animals at Week 4 (FIGS. 16E and 16F) and Week 6 (FIGS. 16G and 16H) is remarkably lower compared to SHAM group (FIGS. 16A, 16B, 16C and 16D). The IoP. and S.C. SPF treatments resulted in an exceptionally high GFAP immunoreactivity in the ventral grey horn at Week 4 (FIGS. 16I and 16J and FIGS. 16M and 16N, respectively) and Week 6 (FIGS. 16K and 16L and FIGS. 16O and 16P, respectively) compared to CRUSH group. Likewise, the number of GFAP immunoreactive astrocytes in the dorsal grey horn is remarkably lower in the CRUSH SPF (IoP.) and CRUSH SPF (S.C.)-treated group at Week 4 and Week 6 compared to CRUSH group (FIG. 17B). Morphometric analysis of the ipsilateral ventral grey horn showed significant (p<0.000) increase in the number of the GFAP-immunostained astrocytes in the CRUSH group compared to SHAM at Week 4 and Week 6 post-injury (FIG. 17A). Further, the number of GFAP positive astrocytes significantly (p<0.000) decreased in the CRUSH SPF (IoP.) treated groups at Week 4 and Week 6 post-injury (FIG. 17C). However, the GFAP immunoreactivity decrease in the CRUSH SPF (S.C.)-treated group remained significantly higher than the SHAM and CRUSH SPF (IoP.) groups at Week 4 (p<0.000) and Week 6 (p<0.002) post-injury (FIG. 17D). Likewise, analysis of the ipsilateral dorsal grey horn showed significant (p<0.000) increase in the number of the GFAP-immunostained astrocytes in the CRUSH group compared to SHAM at Week 4 and Week 6 post-injury. IoP. and S.C. SPF treatments significantly (p<0.000) decreased the number of GFAP-immunostained astrocytes at Week 4 and Week 6 post-injury (FIG. 17E). However, this decrease remained significantly (p<0.02) CRUSH+1×SPF (S.C.) higher compared to SHAM and CRUSH+1×SPF (IoP.) groups at Week 4. At week 6 post-injury, the IoP. and S.C. SPF-treated groups displayed significantly (p<0.01 and p<0.001) higher GFAP immunoreactivity in the dorsal grey horn compared to SHAM group. Western blot analysis of glial fibrillary acidic protein (GFAP) in the lumbar spinal cords from all the experimental groups at Week 4 and Week 6 following nerve injury is demonstrated in FIG. 17C. In support of the GFAP immunohistochemical staining and morphometric analysis, protein density analysis of the spinal cord revealed significant (p<0.000) increase in GFAP content in the CRUSH and SPF-treated groups at Week 4 following sciatic nerve injury (FIG. 17D). However, only the I.P. SPF-treated group displayed a significant decrease in the GFAP protein concentration at Week 4 (p<0.002) and Week 6 (p<0.003) compared to CRUSH group. The GFAP content in the I.P. SPF-treated was not significantly different than SHAM group at Week 4 nor NAIVE or SHAM groups at Week 6 post-nerve injury.

Figure 18A:
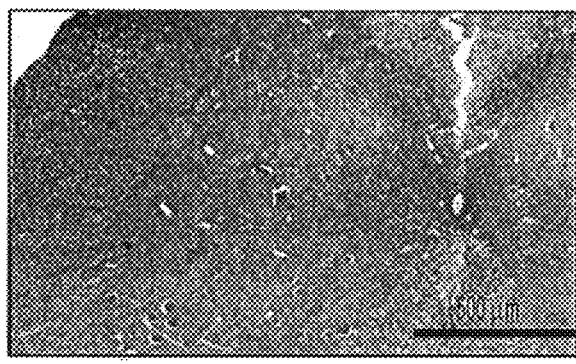
FIGS. 18A-18H show representative 10× photomicrographs of lumbar spinal cord from rats of all groups immunostained for GAP-43 at week 4 and week 6 following nerve crush injury.
Figure 18B:
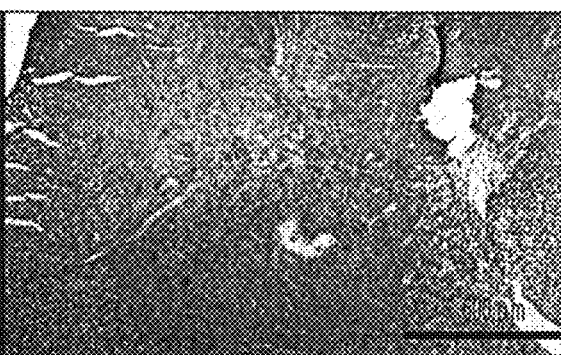
Figure 18C:
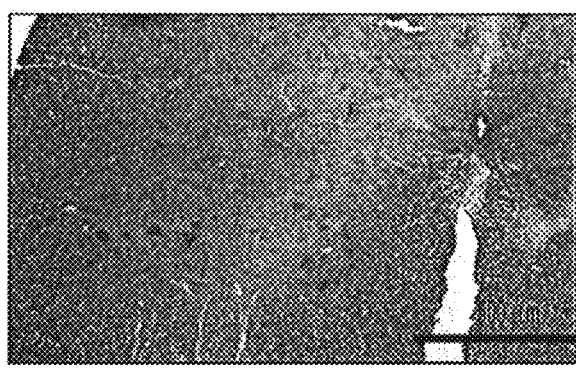
Figure 18D:
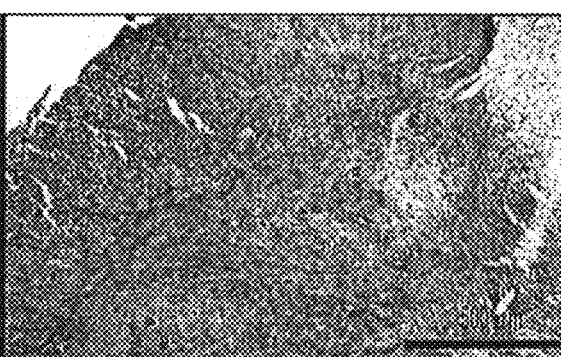
Figure 18E:
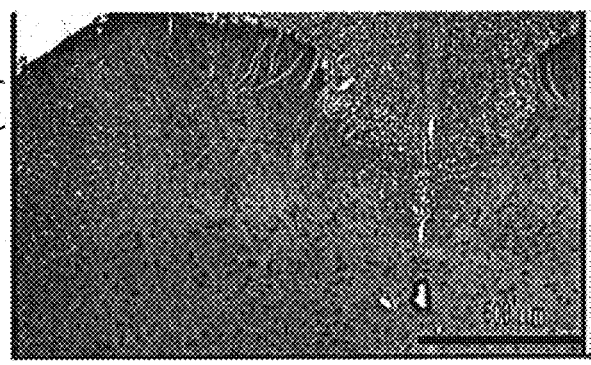
Figure 18F:
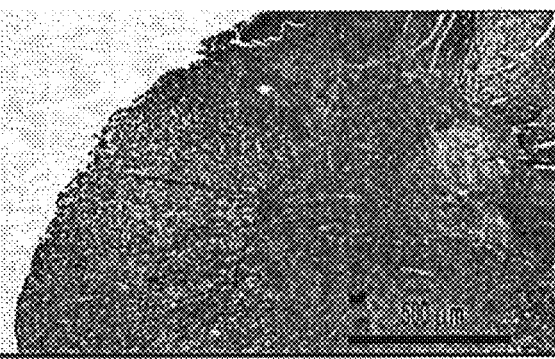
Figure 18G:
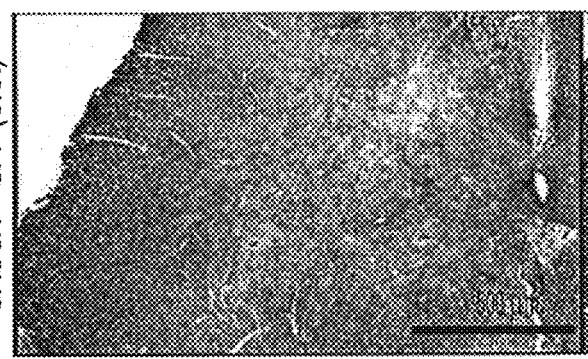
Figure 18H:
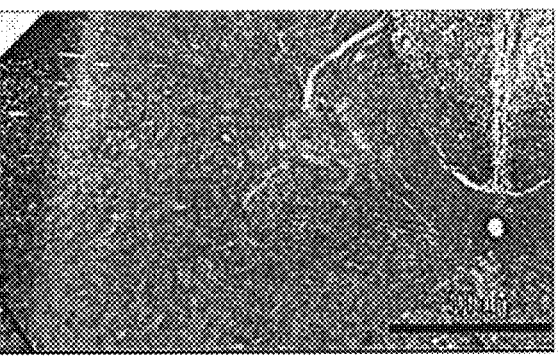
Figures 19A, 19B, 19C, 19D:
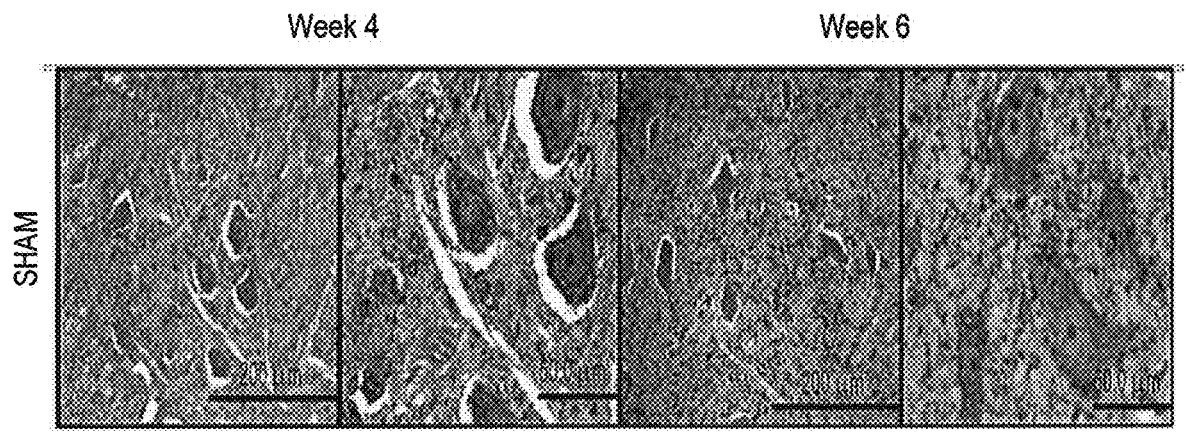
FIGS. 19A-19P show representative 40× and 100× photomicrographs of lumbar spinal cord ventral grey horn from rats of the experimental groups immunostained for GAP-43 protein at week 4 and week 6 post injury.
Figures 19E, 19F, 19G, 19H:
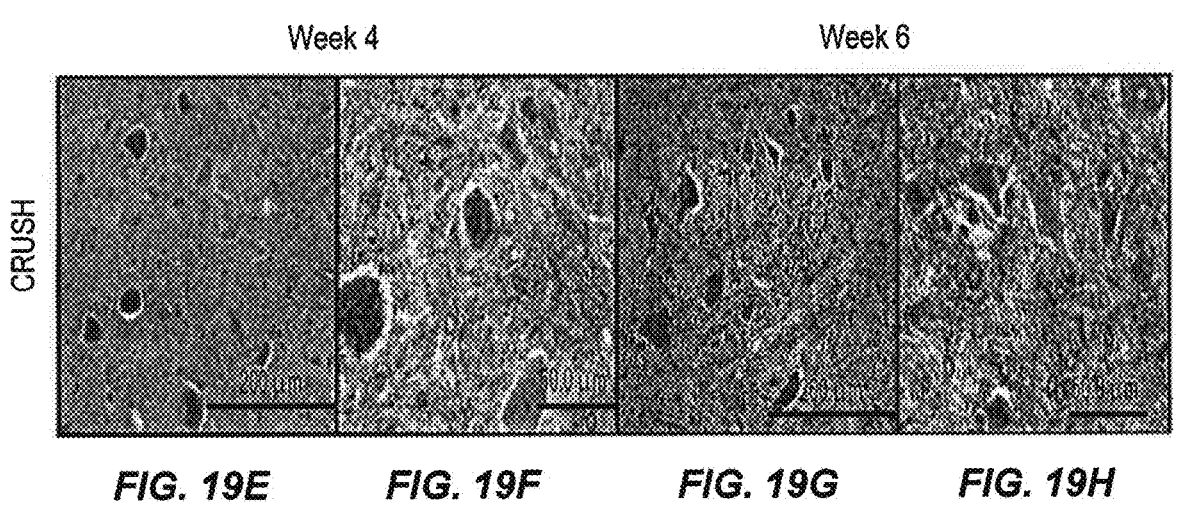

Growth associated protein-43 (GAP-43) immunostaining in the lumbar spinal cord showed a general increase in the immunoreactivity in the CRUSH and SPF-treated animals at Week 4 (FIGS. 18C, 18E and 18G) and Week 6 (FIGS. 18D, 18F and 18H) compared to the SHAM group (FIGS. 18A and 18B, respectively). However, only at Week 6 the I.P. SPF treatment apparently decreased the GAP-43 immunoreactivity compared to the CRUSH group (FIGS. 18F and 18H). High magnification (40× and 100×) photomicrographs of the lumbar spinal cord ventral grey horn immunostained for GAP-43 at Week 4 and Week 6 post-injury are shown in FIG. 18B. The GAP-43 immunoreactivity in the ventral grey horn of the CRUSH animals at Week 4 (FIGS. 19E and 19F) and Week 6 (FIGS. 19G and 19H) was remarkably higher compared to SHAM group (FIGS. 19A, 19B, 19C and 19D). The I.P. and S.C. SPF treatments resulted in a remarkably lower GAP-43 immunoreactivity in the ventral grey horn at Week 6 (FIGS. 19K and 19L and FIGS. 19O and 19P, respectively) compared to CRUSH group. However, at Week 4 post-injury, the I.P. and S.C. SPF treatments did not reveal a noticeable difference compared to the CRUSH group (FIGS. 16I and 16J and FIGS. 16M and 16N, respectively).

Figure 20A:
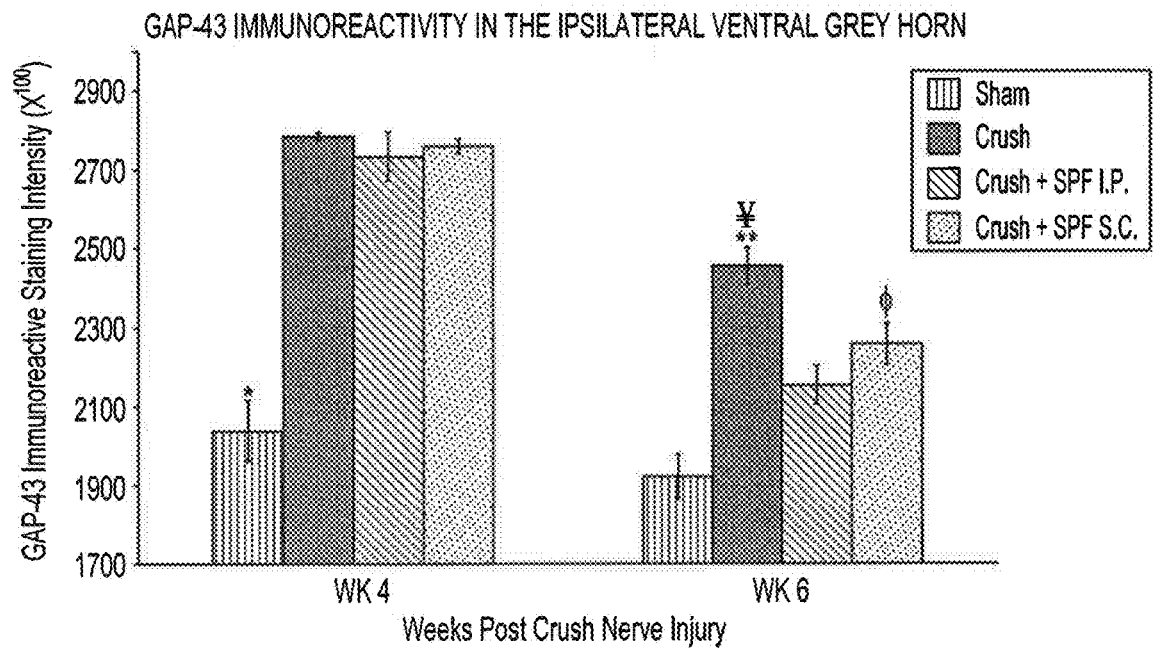
FIG. 20A is a bar graph showing the GAP-43 immunoreactive intensity in the ipsilateral ventral grey horn at week 4 and week 6 post-injury.
Figure 20B:
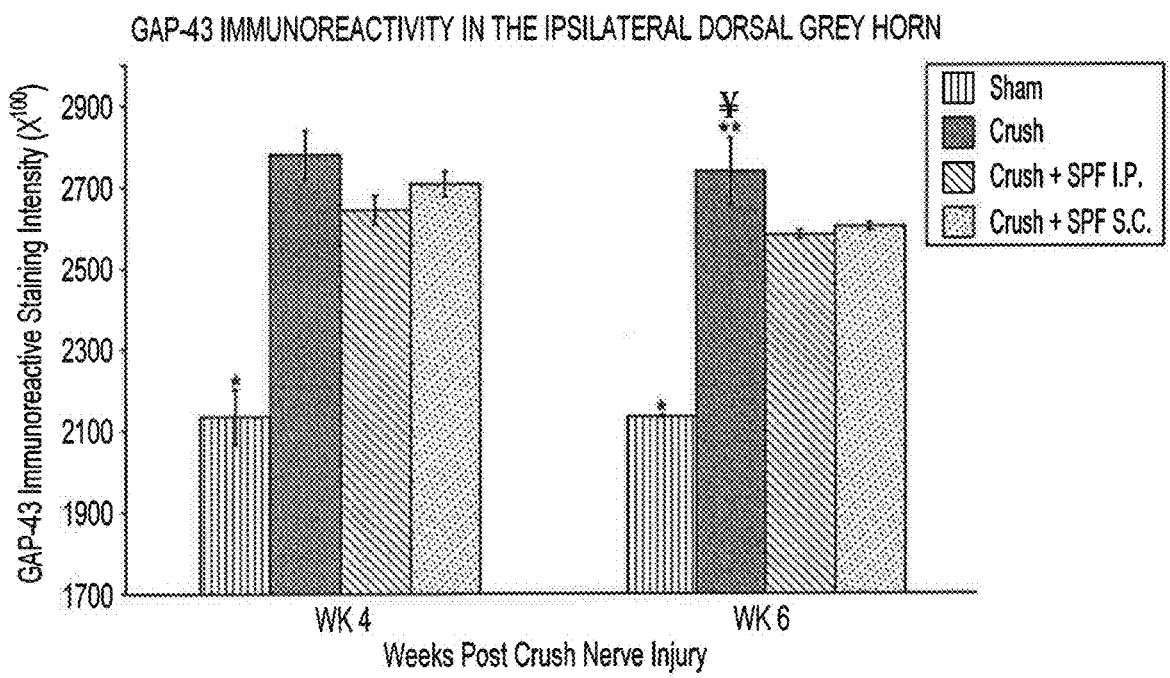
FIG. 20B is a bar graph showing the intensity of the GAP-43 immunoreactivity in the ipsilateral dorsal grey horn at week 4 and week 6 post-injury.
Figure 21A:
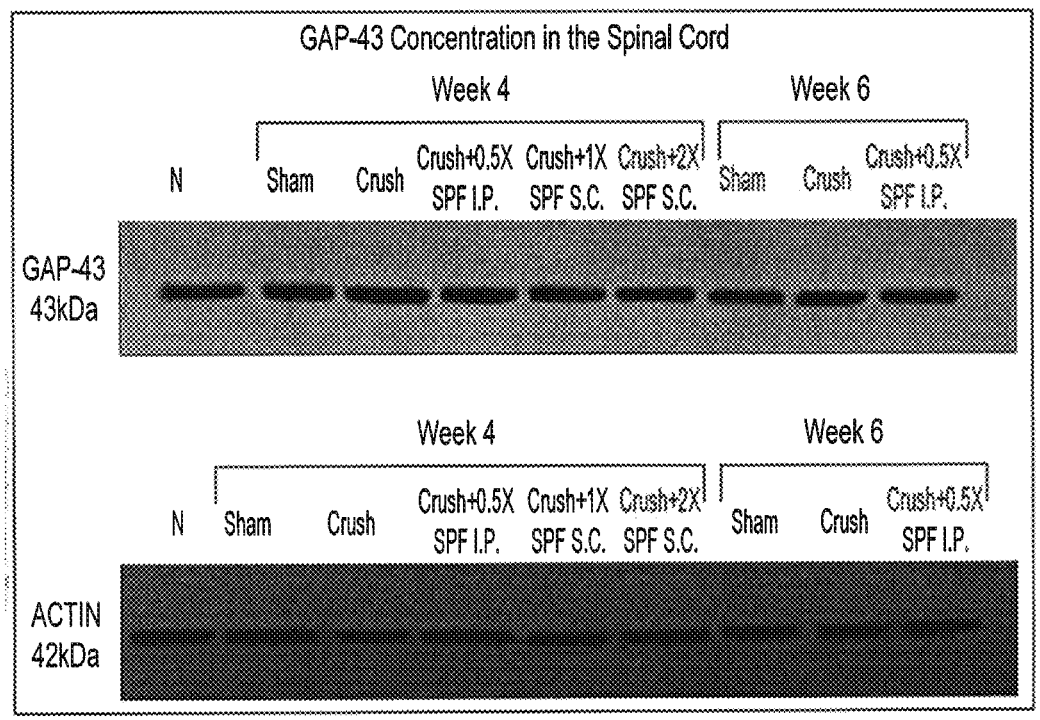
FIG. 21A shows a Western blot analysis of growth associated protein-43 (GAP-43) in the spinal cord from all the experimental groups at Week 4 and Week 6 following nerve injury.
Figure 21B:
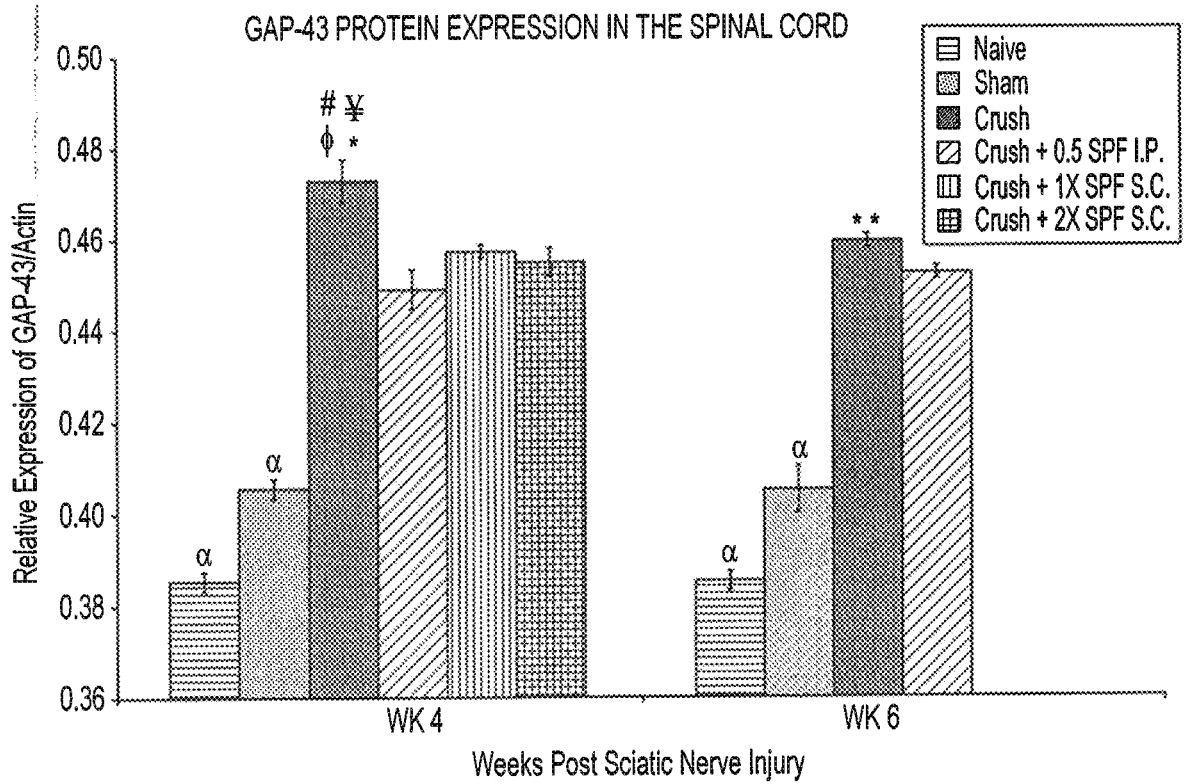
FIG. 21B is a bar graph showing the GAP-43 density in spinal cord samples (n=3 rats/group) normalized with densities of actin band (Molecular weight-42).

Likewise, the GAP immunostaining in the dorsal grey horn was remarkably lower in the CRUSH SPF (I,P.)-treated group at Week 6 compared to CRUSH group. Staining intensity analysis of the ipsilateral ventral grey horn showed significant (p<0.001) increase in the GAP-43-immunostaining in the CRUSH and I.P. and S.C. SPF-treated groups compared to SHAM at Week 4 and Week 6 post-injury (FIG. 20A). The I.P. and S.C. SPF treatments decreased the GFAP immunoreactivity significantly (p<0.03) compared to CRUSH group at Week 6 post-injury. However, the GAP immunoreactivity decrease in the CRUSH SPF (S.C.)-treated group remained significantly (p<0.01) higher than the SHAM group at Week 6 post-injury. Likewise, analysis of the ipsilateral dorsal grey horn showed significant (p<0.000) increase in the intensity of the GAP-43-immunostaining in the CRUSH, CRUSH+0.5×SPF (loP.) and CRUSH+1×SPF (S.C.) compared to SHAM at Week 4 and Week 6 post-injury (FIG. 20B). loP. and S.C. SPF treatments significantly (p<0.02) decreased the GAP-43-immunostaining intensity only at Week 6 post-injury. Western blot analysis of GAP-43 of the lumbar spinal cords from all the experimental groups at Week 4 and Week 6 following nerve injury is demonstrated in FIG. 21A. In support of the GAP-43 immunohistochemical staining and immunostaining intensity analysis, protein density examination of the spinal cord revealed significant (p<0.000) increase in GAP-43 content in the CRUSH and SPF-treated groups at Week 4 and Week 6 following sciatic nerve injury compared to NAIvE and SHAM groups (FIG. 21B). However, the CRUSH+0.5×SPF (loP.), CRUSH+1×SPF (S.C.) and CRUSH+2×SPF (S.C.) groups showed significant (p<0.001, P<0.02 and p<0.009, respectively) reduction in the GAP-43 protein content compared to CRUSH animals at Week 4. At Week 6 post-injury, the GAP-43 protein concentrating in the CRUSH+0.5×SPF (loP.) group remained significantly p<0.048 lower compared to CRUSH group.

Several functional and biochemical parameters were investigated to address the effect of SPF treatment on the peripheral nerve regeneration, neural protection and functional recovery following peripheral nerve crush injury. Our data have shown that administration of SPF intraperitoneally or subcutaneously significantly improved the performance of different neurobehavioral functional tests in animals with nerve injury. SPF treatments also showed significant improvement in sensory and motor functions compared to saline treatment in injured nerves. The SPF treatments resulted in a significant recovery in foot position and toe-spread analyses following injury. Likewise, SPF-treated animals exhibited improvements in motor recovery as measured by the extensor postural thrust, hopping response and Rotarod. Also, the tactile allodynia and plantar mechanical hyperalgesia thresholds significantly decreased compared to the CRUSH group. Nerve crush injury produced severe nociception deficits in both heat withdrawal reflex and tail flick withdrawal latency tests which were markedly recuperated in SPF-treated animals. The neurobehavioral data were supported by significant histomorphological evidence of axonal regeneration following SPF treatments compared to controls at 4 and 6 weeks postoperatively. The CRUSH group displayed a significant increase in the total small and thinly myelinated axon number at week 4 and 6 post-injury that was significantly reduced following SPF treatment indicating constructive regeneration and axonal recovery. Likewise, SPF treatment increased the axon area, average axon perimeters and myelin thickness.

The electron microscopy revealed normal and healthy appearance regenerated sciatic nerve with normal thickness of myelin sheaths and axons in the SPF-treated group compared to the saline-treated group. The regenerated axons in the SPF-treated group also had normal Schmidt-Lantermann clefts associated with normal and healthy appearing myelin sheaths. SPF-treated animals displayed newly regenerated collagen fibers similar to normal collagen fibers with well-organized distribution and absence of disintegrated myelin figures in the extracellular matrix.

Further, the SPF treatments remarkably ameliorated the neurodegenerative changes seen in Cresyl violet stained ventral and dorsal grey horn regions of the spinal cord sections ipsilateral to the nerve injury and significantly prevented the decrease in the number of the NeuN-immunoreactive spinal neurons with a concomitant reduction in the GFAP immunoreactive astrocytes and the GAP-43immunoreactivity.

Peripheral nerve injuries (PNI) are common conditions with broad-ranging groups of symptoms depending on the severity and nerves involved. When the nerve's connective tissues are preserved, but the nerve axon and the surrounding myelin is completely interrupted, axonotmesis occurs. In this type, axon and myelin degeneration occur distal to the site of injury, resulting in complete denervation. The crush injuries (axonotmesis) occur from an acute traumatic compression of the nerve leading to various degrees of neural damage.

Sciatic nerve crush injury is the most commonly studied nerve injury and has been used as a model to test the mechanisms controlling peripheral nerve regeneration. Although sciatic nerve injuries in humans are rare due to the deep anatomical location within the lower extremity, the animal model provides information regarding recoveries of particular nerve types and their potential for improvement as they struggle to reach endoneurial tubules. Also, nerve crush model represents the mild forms of nerve compression damages or neuropathy resulting from diabetes and myelin-related neurodegenerative diseases. In crush injuries, axonal regeneration is mostly successful, and renovation of the function may be complete due to the preservation of the structure. Before the process of regeneration can occur in the damaged nerve, a sequence of degenerative processes must occur depending on the type and severity of the injury, whether motor or sensory neurons and myelinated or unmyelinated fibers are injured, and on consequences such as deficits in axonal transport or demyelination. Axonal degeneration is most likely to be triggered distal to the crush injury site in combination with certain histological change at the injury site or proximal to it. In an anterograde manner, axon and surrounding myelin breakdown until it reaches the distal part of the nerve segment. Both the neurotubules and neurofilaments become disarrayed as a result of axonal swelling leading to fragmentation of the axon. Within 24 hours of injury, Schwann cells (SCs) become active and divide rapidly to give differentiated daughter cells that downregulate myelin-specific proteins as well as upregulate several glial growth factors. With the help of the invading macrophages, SCs start removing the degenerated axonal and myelin debris. Meanwhile, endoneurial mast cells release histamine and serotonin to increase capillary permeability and expedite the migration of macrophages through it. The primary role of axonal degeneration is to remove axon and myelin-derived material to pave the way for the axons to regenerate within 5 to 8 weeks. Consequently, the first two weeks are the most crucial period of the neurodegeneration process, where the inflammation, degeneration of myelinated axons, removing of the dead myelin, and neuronal Schwann cells damage processes are occurring. Thus, it is imperative to intervene within this time frame to influence these processes and protect Schwann cells in the sciatic nerve and the neurons of the spinal cord from the apoptotic process.

For the present studies, SPF treatments started immediately after the induction of the nerve injury and lasted for almost two weeks to lessen the effect of secondary inflammation and degenerative processes while boosting the process of regeneration which starts at the end of the second week following the crush injury. Examination of sciatic nerve sections from SPF-treated animals revealed a remarkable axonal and myelin regeneration. Compared with CRUSH group, these sections contained a higher number of new and sizeable regenerated nerve fibers that were surrounded by much more myelin. Sciatic nerves of the SPF-treated group showed approximately similar normal morphology by the end of the 6th-week post-surgery in contrast to CRUSH sciatic nerve rats. Many small nerve fibers with a normal histomorphology, though still ensheathed with thin myelin, may be designated as regenerated nerve fibers that already began the myelination process. The healthy unmyelinated nerve fiber bundles found in the crushed nerve can be categorized as either regenerated unmyelinated fibers or regenerated nerve fibers that did not reach the full myelination processes. Further, the remyelination process was biochemically confirmed by the increased myelin basic protein (MBP) concentration in the SPF-treated injured sciatic nerves.

For the present studies, SPF neurobehavioral recovery, as well as the morphological improvements in the histological architecture of the crush-injured nerves were supported by the increased survival of neurons in the ventral and dorsal horns of spinal cords of SPF-treated rats. In this study, our histological examination of the Cresyl violet stained sections of the lumbar spinal cord ventral and dorsal grey horns at Week 4 and 6 after nerve injury showed that the CRUSH animals revealed fewer healthy ventral and dorsal horn neurons and a large number of degenerating neurons at Week 4 compared to SHAM. Meanwhile, the number of neurons (NeuNimmunostained) in the spinal cord ipsilateral horns was significantly more in SPF-treated groups compared to the CRUSH group at Week 4 and Week 6 after nerve crush injury. Apoptosis is distinguished by early chromatin condensation followed by internucleosomal DNA cleavage, cell shrinkage, reorganization of the cytoskeleton, organelle relocation and production of apoptotic bodies. Death occurs more frequently in proximal crush nerve injuries, and survival of the cell is not assured after severe nerve injury. However, activation of apoptosis involves increasing caspase-3 activity and different executioner caspases which are responsible for destroying normal cellular functions leading to cell death.

Anti-apoptotic proteins such as Bcl-2 family are involved in the protection of neuron from damage. Bcl-2 family proteins stabilize mitochondrial functions, which inhibit cytochrome c release, Apaf-1 oligomerization, and activation of caspase-9. This plays a crucial role in neuronal cell survival.

Considering apoptotic process taking place following crush nerve injury, the neuroprotection of ventral and dorsal horn neurons in the SPF-treated groups support the possibility that SPF has an anti-apoptotic role in the survival of the spinal cord neurons. The extrinsic apoptotic pathway, which is initiated by transmembrane receptor-mediated interaction, involving tumor necrosis factor (TN F) as death receptors cannot be ruled out. TNF possesses a wide range of proinflammatory actions produced chiefly by activated macrophages at the nerve injury site and neurons of the spinal cord.

Additionally, the immunohistochemical study of spinal cord sections revealed that SPF reduced the expression of the glial fibrillary acidic protein and growth associated protein 43, a marker of regenerating axons. GFAP is the main intermediary filament for astrocytes and is a marker for reactive gliosis, which is related to neuronal damage and aging. In the present study, GFAP immunostaining for astrocytes showed a remarkable increase in the GFAP-immunoreactive astrocytes in the ventral and dorsal grey horns of the CRUSH animals at Week 4 and Week 6 compared to the SHAM group.

Meanwhile, the SPF treatments significantly decreased the GFAP immunoreactivity in the spinal cord segments corresponding to the sciatic nerve origin compared to the CRUSH group at Week 4 and Week 6. The GFAP immunohistochemical staining and morphometric analysis data were further supported by the protein density analysis of the spinal cord. Western blot analysis of GFAP in the lumbar spinal cords from SPF-treated group displayed a significant decrease in the GFAP protein concentration at Week 4 and Week 6 compared to CRUSH group, indicating a neuroprotective effect of SPF after sciatic nerve injury. This neuroprotection is attained by deterring the process of gliosis and neuronal damage, thus promoting cellular regeneration. Normally, astrocytes play various roles in neuronal activity, including regulation of ion flux currents, energy production, neurotransmitter release and synaptogenesis. Astrocytes are critical for healthy CNS function, and alterations in their activity could contribute to neuronal damage. Reactive astrogliosis leads to increased production of various cytokines and chemokines such as TGF-a, IL-1 a, IL-6, ciliary neurotrophic factor (CNTF), adhesion/recognition molecules, and proteins such as COX2, inducible NO synthase, and calcium-binding protein S100a which drive the secondary neuronal damage. Further, astrogliosis can exert both beneficial and detrimental effects depending on signaling pathways activated and timing after crush nerve injury. Astrogliosis minimizes secondary tissue damage by limiting the damaged area, providing growth factors, restoring blood-spinal cord barrier and tissue structure, revascularization, and maintenance of homeostasis and removal of tissue debris from the injured area.

However, recent studies revealed the importance of timing in modulating various aspects of reactive astrocytes after neuronal injury. Therefore, the beneficial role of reactive astrocytes is mainly at the early stages of injury or secondary inflammation process. As time passes following injury, inhibitory properties of reactive astrocytes progress and overcome their constructive effects. This is mainly accredited to the up-regulation of inhibitory molecules that strongly obstruct neural repair and regeneration. In this regard, the results described herein showing an increase in the GFAP immunoreactive astrocytes following nerve crush injury agrees with their crucial initial role in containing the secondary damage and recruiting and manipulating the subsequent inflammatory response. It has been shown earlier that astrocytes increase in number and migrate to the site of injury. Further, the decrease in the reactive astrogliosis following the SPF treatment may indicate a tuning down of the inflammatory process and less recruitment of neutrophil and macrophages infiltration at the crush injury nerve site and the corresponding spinal cord segments leading to improved motor function, tissue sparing and neuroprotective effects. After the neural tissue injury, normal microglia function becomes abnormal and dysfunctional. The so-called "below-level" pain in mid-thoracic spinal cord injury compared to peripheral nerve injury results, though they have different mechanisms, they may have a common dysfunctional glial pathology. In this regard, allodynia correlated with the severity of "below level" chronic pain may result from continuous glial activation and production of inflammatory mediators produce and maintain sensitization of dorsal horn neurons in segments remote from the spinal injury site.

The term "gliopathy" proposed by Hulsebosch in 2008 to describe the dysfunctional and maladaptive response of astrocytes and microglial to neural injury, as one of the cellular sources for cytokine production following spinal cord injury occurs in regions near and remote from the spinal lesion in both an autocrine and paracrine manner, creating persistent glial inflammation. The genomic studies indicated that nerve stimulated microglia show fluctuations in the levels of neurotrophins, lysosomal enzymes, antioxidants, and NFKP, distinguishing their resting and activated states. Proteomics analyses identified lysosomal, antioxidant, and cytoskeletal proteins as being up-regulated in nerve-stimulated microglia. The upregulation of cathepsin and other lysosomal enzymes is critical for microglial clearance, and for the mobilization of adaptive immunity.

Inhibition of glial activation, both astrocytic and microglia improves chronic and persistent pain syndromes in remote segments below the level of the lesion after spinal cord injury. The present findings demonstrated significant GFAP protein increase in concurrence with the rise in pain threshold as measured by different hyperalgesia parameters in the crush injury animals. SPF treatments resulted in the reduction of central and peripheral neuropathic pain (allodynia, mechanical and thermal hyperalgesia) with a significant reduction of GFAP protein expression and "gliopathy."

The present inventors explored the effect of SPF on GAP-43 which is a membrane protein involved in neuronal development and plasticity. GAP-43 is a protein found in growth cones or actively remodeling terminals and is thus used as a neuronal marker of regions undergoing neurite outgrowth or capable of plasticity in adult animals. It is also considered an essential factor for proper neuronal regeneration. It has been established that GAP-43 expression increases (both centrally and peripherally) after peripheral neuronal injury and then it is transported peripherally, where it contributes to neuronal regeneration.

In the present studies, GAP-43 immunostaining intensity analysis of the ipsilateral ventral and dorsal grey horns showed a significant increase in the GAP-43-immunostaining in the CRUSH and I.P. and S.C. SPF-treated groups compared to SHAM at Week 4 and Week 6 post-injury. The I.P. and S.C. SPF treatments decreased the GFAP immunoreactivity significantly compared to CRUSH group at Week 6 post-injury. In support of the GAP-43 immunohistochemical staining and immunostaining intensity analysis, protein density examination of the spinal cord revealed a significant increase in GAP-43 content in the CRUSH and CRUSH SPF-treated groups at Week 4 and Week 6 following sciatic nerve injury compared to NAÏVE and SHAM groups. However, the SPF-treated animals showed a significant reduction in the GAP-43 protein content compared to CRUSH animals at Week 4.

At Week 6 post-injury, the GAP-43 protein concentrating in the CRUSH SPF (I.P. group) remained significantly lower compared to CRUSH group. The present findings agree with the role of the GAP-43 protein as an active remodeling factor in the regions undergoing neurite outgrowth for proper neuronal regeneration. The increase in GAP-43 in the CRUSH and CRUSH SPF-treated groups indicates that the process of axonal regeneration and neuronal outgrowth in the spinal cord is still going on at Week 4. The fact that the SPF treatment significantly reduced GAP-43 content, although not to control levels, indicates that the need for GAP-43 decreases as neuroregeneration proceeds for its completion which takes place approximately by Week 10 post nerve injury.

The results described herein demonstrate that no single component whether lipid or protein can perform all the regeneration and repair and reverse the damage caused by the CRUSH through IP or SC injection of SPF. For the repair and regeneration processes, it seems that some of the lipid components and proteins are needed together and act in synergism. The lipids in SPF aggregate to protect against oxidation. Some of the biologically active lipids such as cicosanoids, steroids and furan fatty acids, exist in minute amounts and can only be detected by GC-MS. As their separation into single components leads to their oxidation and changes in their structures, this will lead to loss of their activities. The proteins contain growth factors which have not been fully characterized. Their involvement in the sequence of the repair and regeneration events has yet to be established. These facts justify use of the mixture of lipids and proteins (SPF) as a natural fraction from CSP in our research activities, and repeatedly it proved effective in healing and regeneration of tissues.

The data obtained showed that IP injection of SPF was more effective than SC injection in recovery and regeneration of crushed sciatic nerves.

As set forth herein, SPF treatment alleviates neurobehavioral deficits and stimulates regeneration of the axons and histomorphological alterations following nerve injury. Further, SPF protects spinal neurons and enhances subcellular recovery after peripheral nerve injury and thus improves nerve regeneration. Based on these findings, SPF can be used for treatment of nerve injury and other neurological deficits in humans. The present findings also demonstrate the potential for using SPF for treatment of neuropathy and neurodegenerative diseases such as Alzheimer's, Parkinson's, Multiple Sclerosis and Glaucoma.

It is to be understood that the method for treating nerve damage using epidermal gel secretion of catfish is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating nerve damage resulting from nerve crush, comprising:
providing a therapeutic composition, the therapeutic composition including a soluble protein fraction prepared by fractionating epidermal gel secretions of catfish, the soluble protein fraction including about 87% soluble proteins and about 13% lipids; and
administering a therapeutically effective amount of the therapeutic composition to a patient suffering from nerve damage resulting from nerve crush,
wherein the composition is administered by subcutaneous or intraperitoneal injection.

2. The method according to claim 1, wherein the fractionating comprises:
mixing the epidermal gel secretions with an extraction buffer to provide an extract; homogenizing the extract with a homogenizer to provide a homogenate; and
centrifuging the homogenate to provide the soluble protein fraction and an insoluble protein fraction.

3. The method according to claim 2, wherein the extraction buffer comprises phosphate buffered saline.

4. The method according to claim 2, wherein the fractionating further comprises:

fractionating the insoluble protein fraction to provide an additional soluble protein fraction and an additional insoluble protein fraction; and adding the additional soluble protein fraction to the soluble protein fraction obtained by fractionating the epidermal gel secretions.

5. The method according to claim 2, further comprising determining whether the soluble protein fraction includes about 87% soluble proteins and about 13% lipids.

6. The method according to claim 5, further comprising adding at least one additional lipid fraction to the soluble protein fraction.

7. The method according to claim 1, wherein the catfish is Arabian Gulf catfish.

8. The method according to claim 1, wherein the therapeutic composition is administered by subcutaneous injection.

9. The method according to claim 1, wherein the therapeutic composition is administered by intraperitoneal injection.

10. The method according to claim 1, wherein the therapeutically effective amount includes about 3 mg to about 3.5 mg of the soluble protein fraction per 100 gm of body weight of the patient.

* * * * *